United States Patent [19]

Gaynor et al.

[11] Patent Number: 5,677,143

[45] Date of Patent: Oct. 14, 1997

[54] CELLULAR NUCLEIC ACID BINDING PROTEIN AND USES THEREOF IN REGULATING GENE EXPRESSION AND IN THE TREATMENT OF AIDS

[75] Inventors: Richard B. Gaynor, Dallas; Foon K. Wu, Carrollton, both of Tex.

[73] Assignee: Board of Regents, University of TX System, Austin, Tex.

[21] Appl. No.: 242,677

[22] Filed: May 10, 1994

Related U.S. Application Data

[63] Continuation-in-part of Ser. No. 788,266, Nov. 5, 1991, Pat. No. 5,350,835.

[51] Int. Cl.$^6$ ............... C12P 21/06; C12N 1/08; C12N 15/00; C07H 21/04
[52] U.S. Cl. ............... 435/69.1; 435/6; 435/240.2; 435/320.1; 435/183; 435/270; 536/23.5; 935/1; 935/16; 935/22; 935/76; 935/77
[58] Field of Search ............... 435/6, 91.1, 91.2, 435/69.1, 240.2, 320.1, 183, 270, 272; 536/23.5; 935/1, 16, 22, 76, 77, 89

[56] References Cited

U.S. PATENT DOCUMENTS 4,683,202  7/1987  Mullis ............... 435/91

OTHER PUBLICATIONS

Dialog Search Report (1991).
Garcia et al. (1989), *The EMBO Journal*, 8(3):765–778.
Marciniak et al. (1990), *Cell*, 63:791–802.
Berkhout et al. (1989), *Cell*, 59:273–282.
Laspia et al. (1990), *Genes & Development*, 4:2397–2408.
Marciniak et al. (1990), *Proc. Natl. Acad. Sci. USA*, 87:3624–3628.
Garcia et al. (1987), *The EMBO Journal*, 6(12):3761–3770.
Gaynor et al. (1989), *Proc. Natl. Acad. Sci. USA*, 86:4858–4862.
Harrich et al. (1990), *The EMBO Journal*, 9(13):4417–4423.
Roy et al. (1990), *Genes & Development*, 4:1365–1373.
Pearson et al. (1990), *Proc. Natl. Acad. Sci. USA*, 87:5079–5083.
Wu et al. (1988), *The EMBO Journal*, 7(7):2117–2129.
Dignam et al. (1983), *Nucleic Acids Research*, 11(5):1475–1488.
Field et al. (1988), *Molecular and Cellular Biology*, 8(5):2159–2165.
Gatignol et al. (1989), *Proc. Natl. Acad. Sci. USA*, 86:7828–7832.
Goody et al. (1991), *FEBS Letters* (pp. 1–5).
Calnan et al. (1991), *Genes & Development*, 5:201–210.
Wu et al. (1991), *Genes & Development*, 5(11):2128–2140.
Gaynor, R. (1991), Role of the TAR Element in Regulating HIV Gene Expression, In: Advances in Molecular Biology and Targeted Treatment of AIDS, pp. 79–90.

Gaynor, R. (1991), Cellular Factors Involved in Regulating HIV Gene Expression, In: Genetic Structure and Regulation of HIV, Haseltine and Wong–Staal, editors, pp. 107–134.
Waterman et al. (1991), Nuclear Proteins Implicated in HIV–1 Transcriptional Control, In: Genetic Structure and Regulation of HIV, Haseltine and Wong–Staal, editors, pp. 391–403.
Sheline et al. (1991) *Genes Develop.*, 5(12b):2508–2520.
Gaynor, R., (1992), *AIDS*, 6(4):347–363.
International Search Report, No. 92/09546.
Calvert et al., "Cloning and characerization of a novel sequence–specific DNA–binding protein recognizing the negative regulatory element (NRE) region of the HIV–1 long terminal repeat," *Gene*, 101:171–176, 1991.
Du et al., "Human transcription factor USF stimulates transcription through the initiator elements of the HIV–1 and the Ad–ML promoters," *The EMBO Journal*, 12(2):501–511, 1993.
Morgenstern and Land, "Advanced mammalian gene transfer: high titre retroviral vectors with multiple drug selection markers and a complementary helper–free packaging cell line," *Nucleic Acids Research*, 18(12):3587–3596, 1990.
Olsen et al., "Interaction of Cellular Factors with Intragenic Cis–Acting Repressive Sequences within the HIV Genome," *Virology*, 191:709–715, 1992.
Reddy, "Regulation of HIV–1 Gene Expression by Cellular Transcription Factors," *Pathobiology*, 60:219–224, 1992.
West et al., "Characterization and Purification of a Novel Transcriptional Repressor from HeLa Cell Nuclear Extracts Recognizing the Negative Regulatory Element Region of Human Immnodeficiency Virus–1 Long Terminal Repeat," *The Journal of Biological Chemistry*, 267(35):24948–24952, 1992.

*Primary Examiner*—Bradley L. Sisson
*Attorney, Agent, or Firm*—Denise L. Mayfield

[57] ABSTRACT

The invention relates to a cellular protein which is specific and has high affinity for nucleic acid sequences characteristic of an intact TAR RNA loop sequence of the HIV LTR TAR region. The invention also relates to a protein preparation having a protein of about 185 kD that is isolated from a mammalian cell nuclear extract preparation, most specifically a HeLa cell extract that is purified between 1,000–10,000 fold. The protein of about 185 kD is shown to regulate HIV viral gene expression by binding a TAR RNA region of an HIV LTR template, in the presence of a cofactor fraction (including at least a –100 kD cofactor), and a tat protein. A route for the development of immunodiagnostics for AIDS and related disorders may also be provided given the specific and high affinity of TRP-185 for HIV RNA. The 185 kD protein and related encoding amino acid and DNA sequences are provided and may be used in therapeutic agents for AIDS and related disorders and, for the generation of specific antibodies for use in the diagnosis and study of the epidemiology of AIDS.

31 Claims, 19 Drawing Sheets

CELLULAR NUCLEIC ACID BINDING PROTEIN AND USES THEREOF IN REGULATING GENE EXPRESSION AND IN THE TREATMENT OF AIDS

This application is a continuation-in-part of U.S. Ser. No. 07/788,266, filed Nov. 5, 1991, since issued as U.S. Pat. No. 5,350,835 to which priority is claimed.

The government may own rights in the present invention as research relevant to the development thereof was supported by grants from the U.S. government, NIH Grant AI25288.

BACKGROUND OF THE INVENTION

1. Field of the Invention

The invention relates to the field of cellular proteins, most particularly cellular proteins capable of binding nucleic acids and regulating gene expression, including their cloning and characterization. The invention also relates to the field of reagents useful in the characterization of viral and cellular gene expression. In addition, the invention relates to the field of therapeutic methods and reagents for the treatment of viral diseases, such as AIDS and HIV-related pathologies. Methods and reagents (including monoclonal antibodies) for screening/testing biological samples for viral infection are also within the field of the present invention.

2. Background of the Related Art

Gene expression of the human immunodeficiency virus (HIV) is regulated by a variety of mechanisms. The long terminal repeat (LTR) is the site of multiple regulatory regions involved in both general and tissue specific gene expression.[1-16] Two regions, including the NFAT[17,18] and NF-kappa B motifs[4,19,20] are involved in the regulation of the HIV LTR in activated T-lymphocytes. Other elements such as Sp1[2,11] and TATA[3,7,10] are involved in regulating gene expression in a variety of both lymphoid and nonlymphoid cell lines.

HIV contains an additional regulatory element known as the transactivating region, TAR, which extends from −17 to +80 in the HIV LTR.[1,3,5-7]

The TAR element is required for activation of gene expression by the viral transactivator protein, tat.[9,12,20-25] The structural integrity of TAR RNA is a key element for tat activation.[5,6,9,12] TAR RNA is capable of forming a stable stem-loop structure. Disruption of this stem base pairing results in a marked decrease in tat activation. However, compensatory mutations which restore stem base pairing result in nearly wild-type levels of tat activation.[5,6,15] The loop and bulge regions in TAR are also required for high level activation by tat.[5,13,27] Substitution of a single base pair in the loop will decrease tat activation, while substitution of multiple base pairs in this region has been reported to result in even further decreases in tat activation.[9,10,15] Deletion of the bulge region, or substitution for a single "U" residue at +23 in the bulge region, has also been reported to severely decrease tat activation.[15,16,27] These three major determinants, including the stem, loop, and bulge, are thus each required for wild-type activation of the TAR element and the ultimate gene expression of HIV.

The tat protein has been reported to be capable of binding via its basic domain to the bulge region in TAR RNA.[16,27,29] Other nuclear proteins have also been reported to be capable of binding to TAR RNA.[30-32] However, the role or importance of these "binding" proteins, particularly in the regulation of gene expression, has not been fully characterized.

UV-crosslinking assays have been used to identify a 68 kDa cellular protein that binds specifically to the TAR loop region.[26] The present inventors have used modified UV-crosslinking assays to identify cellular proteins that bind to TAR RNA. The detection of this protein was dependent on the use of heparin and ribonuclease following the binding reactions. However, when nonspecific RNA or poly (I)-poly (C) was used in gel retardation assays without ribonuclease, this species was no longer detected (unpublished results). Another RNA binding protein, TRP-140, that binds with high affinity to a variety of double-stranded RNAs, may also potentially have functional significance in regulating HIV gene expression.

Several viruses, such as those of the HIV and the HTLV (human leukemia/lymphoma virus) type, have within their gene structure a downstream regulatory region, to which a cellular protein binds, that is required for transactivation (a protein that acts in conjunction with a viral protein as a transactivating factor), this downstream regulatory region is known as the pX region49. A more complete understanding of the mechanisms which govern viral gene expression, and more particularly the role of binding proteins for the TAR region in gene expression, would provide methods for selectively "turning on" and "turning off" viral genes. Therapeutic agents that selectively "turned off" viral expression, of such as HIV and HTLV expression in an animal, would also be developed using this selective mechanism.

HIV is recognized as the causative agent of Acquired Immunodeficiency Syndrome (AIDS). Therapeutic agents which have been used in the treatment of AIDS include AZT (azidothymidine) and DDI (dideoxyinosine).[33] Both of these agents are nucleotide analogs that target the viral enzyme, reverse transcriptase. While these agents have been used with varying degrees of success, they are also unfortunately associated with a variety of severe side effects. Some of these side effects include peripheral neuropathy (DDI), pancreatitis, granulocytopenia, anemia, severe headache, nausea, insomnia, neurotoxicity, and seizure. These agents have also been associated with a potential carcinogenicity and teratogenicity.[33]

Other molecular targets under investigation as anti-viral targets include an HIV-gene encoded protease. The protease is encoded on the polygene of HIV-1. The polygene encodes three proteins—a reverse transcriptase, a self-cleaving protease (that is required for processing the reverse transcriptase) and a nuclease that is essential for integration of viral DNA into the genome of a host cell. Inhibitors of the HIV protease have been developed using the crystal structure of the protein.

Other potential molecular targets for affecting viral gene expression include the glycosylated envelope protein of HIV and the receptor protein CD4. CD4 is a T cell co-receptor glycoprotein on the surface of lymphocytes to which the virus binds. A soluble form of CD4 can bind to the viral envelope protein and prevent the virus from entering cells. Alternatively, a conjugate of CD4 and a toxin might be used to attack HIV-infected cells, since such cells express the envelope protein on their surfaces. Another drug, dextran sulfate, has also been used in the treatment of AIDS. This drug blocks the binding of HIV to target cells.

None of these molecular targets for anti-viral therapy relates to an agent of cellular origin capable of specifically affecting viral gene expression. An enhanced understanding of the particular role of cellular proteins in the molecular events of both cellular and viral (HIV) gene expression would provide a new avenue for the development of effective anti-viral agents. Such information would further provide for the development of a new genus of drugs based on the regulation of host proteins for the treatment of diseases such as AIDS and AIDS-related diseases.

The present inventors have characterized a particular cellular protein designated "TRP-185" This protein possesses both high affinity and marked specificity of binding to a viral TAR RNA region in a manner that correlates with in vivo genetic data. Specifically, the TRP-185 cellular protein has been characterized by the present inventors to bind templates that are activated by the transactivating protein.

Thus, a solution to providing for the specific inhibition of viruses, such as HIV and HTLV is disclosed. It is an object of the invention to provide a tool which is useful in the characterization of viral and cellular gene expression. It is still another object of the invention to provide a reagent which is useful in the study of vital gene regulation.

It is still a further object of this invention to provide a better, more reliable and convenient procedure for testing human serum and plasma for presence of the AIDS virus.

It is another object of the invention to provide a method for monitoring HIV-disease progression and treating HIV-disease. How these and other objects of this invention are achieved will become apparent in light of the accompanying disclosure.

SUMMARY OF THE INVENTION

The present invention addresses one or more of the problems in the art relating to the characterization and control of gene expression, particularly viral HIV gene expression. The present invention also addresses the need for highly specific alternative AIDS and AIDS-related disease therapeutic agents. These agents target particular molecular events of HIV gene expression by controlling for the activity of a specific cellular protein, designated herein as a "TRP-185" protein.

The invention provides for the preparation and use of specific cellular protein antigens, particularly those antigens associated with the activation of HIV expression, that are useful in themselves and in the development of diagnostic methods for HIV infection. The invention involves the identification of the above designated cellular protein, which has been found to be an important regulatory protein of viral gene expression. The invention also identifies and provides for the isolation of cellular proteins and particular cellular "cofactors" important in facilitating vital gene binding and HIV gene expression.

The nucleic acid sequence and amino acid sequence of the cellular protein TRP-185 has also been determined by the present inventors. Knowledge of the sequences that encode the TRP-185 protein and proteins having the biological activity similar to the TRP-185 protein, are useful in the preparation of expression vectors for transforming whole cells to produce recombinant cellular protein antigenic polypeptides. These recombinant proteins may be employed as reagents in the molecular characterization of gene expression. It is further proposed that the cellular proteins demonstrated to be important in HIV gene expression herein will be useful in the preparation of immunodiagnostic agents and therapeutic agents (i.e. inhibitors) for the treatment of HIV-related diseases (i.e. AIDS, ARC, ALT (adult T-cell leukemia/lymphoma)).

The present invention, more specifically, provides a particularly defined nucleic acid binding element comprising a cellular protein capable of binding with specificity and high affinity to a TAR region of nucleic acid. Even more particularly, the inventors demonstrate that the disclosed nucleic acid binding element will bind to an TAR region of the HIV RNA in the presence of a cofactor fraction.

For purposes of describing the present invention, the nucleic acid binding element has been designated "TRP-185". This particular designation was derived from characterization of the TRP-185 cellular protein as having a molecular weight of between about 175 to about 190 kD, as determined by sucrose gradient sedimentation analysis. Even more specifically, the molecular weight of the TRP-185 is about 185 kD (silver stained gel—see FIG. 10). The TRP-185 binding protein identified in these analysis has been determined to be in a monomer form. Binding of the TRP-185 protein provides for the activation of the trans-activating region of the viral RNA, and gene expression of the viral tat trans-activator protein occurs. The nucleic acid binding element TRP-185 may be useful alone as a tool for elucidating mechanisms of HIV and cellular gene expression. The inventors demonstrate that TRP-185 requires the presence of elements in a "cofactor" fraction for most enhanced binding to the TAR region of HIV RNA. The cofactor fraction is defined, for purposes of describing the present invention, as a composition including at least one cofactor, the fraction having a molecular weight of between about 85–100 kD. The elements present in the cofactor fraction do not themselves bind to the TAR RNA binding site. The cofactor fraction has been characterized by the inventors as containing individual 36, 41, 42, 43, 45, 47, 53, 55, 58, 60 and 85 kD molecular weight proteins.

In the presence of the cofactor fraction, the TRP-185 binds with specificity and high affinity to a particular region of the HIV RNA, designated the TAR region of the long terminal repeat (LTR) of mRNA. Even more particularly defined, the TRP-185 cellular protein binds to a TAR (transactivating) region of the HIV mRNA with an affinity of about $3\times10^{10}$M.

Binding of the TRP-185 to the TAR region of HIV RNA is shown to increase transcription of wild-type HIV LTR, thus increasing the replication of the virus by about 4-fold. As used in the description of the present invention, the term "TAR region" is defined as a transactivating region of a nucleic acid sequence, most specifically a TAR region of the HIV mRNA LTR. The TAR region to which the nucleic acid binding element (i.e. TRP-185) binds comprises an at least 12 base-pair segment of the TAR mRNA region. Defined in terms of the particular base pairs of the TAR mRNA, the TRP-185 cellular protein may be described as binding a nucleic acid segment between bases 23–34 of the TAR mRNA. The sequence of the TAR region of HIV RNA is provided in FIG. 3.

The present invention also provides a highly efficient method for isolating and preparing the cellular protein found to bind a TAR mRNA sequence or region of HIV. In one particularly preferred embodiment, the nucleic acid binding element of the present invention may be prepared by a process comprising the steps of obtaining a volume of mammalian cells, preparing a nuclear extract from the mammalian cells, fractionating the nuclear extract, selecting fractions having TAR binding activity and isolating an element having a molecular weight of between 175–190 kD from the selected fractions to provide a nucleic acid binding element.

Even more particularly, fractionating the nuclear extract to obtain the TRP-185 nucleic acid binding element includes the steps of chromatographing a nuclear extract on a heparin binding column, such as heparin agarose, eluting the chromatographed nuclear extract with potassium chloride or other suitable buffer to obtain TAR active binding fractions, selecting TAR active binding fractions and obtaining a dialysate thereof, chromatographing the dialysate on an anionic separation gel, such as an HTP Bio gel, precipitating TAR active binding fractions from the anionic separation gel with ammonium sulfate or other precipitating buffers or salts, applying the TAR active binding fractions to molecular weight separation gel, such as a Superdex 200 FPLC column, collecting TAR active binding fractions and applying a dialysate of selected fractions therefrom to a second molecular weight separation gel, for example a Bio Rex column, collecting active HIV binding fractions and applying a dialysate thereof to an anionic separation gel or matrix, such as a Dextran Blue-Sepharose column, collecting active TAR binding fractions and applying a dialysate thereof to another anionic separation gel, for example a Mono Q FPLC column, collecting TAR active binding fractions and applying a dialysate of selected washed fractions to a continuous sucrose gradient, and isolating a nucleic acid binding element having a molecular weight of between about 175 kD to about 190 kD as determined by a continuous sucrose gradient, said element having TAR region binding activity.

The term "TAR active binding" as used in the description of the present invention relates to the ability or the demonstration of the ability of a particular sample or elements within a sample or column fraction to bind the TAR region of a nucleic acid, such as DNA or RNA, and is even more specifically described as a fraction having binding activity for the bulge and loop TAR region of the HIV mRNA LTR. As described herein this binding is most enhanced by adding a cofactor fraction.

Any of a variety of mammalian cells may be used as a source to prepare a nuclear cell extract. Preferably, mammalian or animal cells used to prepare the nuclear extract are cells that are susceptible to HIV infection or related viruses. By way of example, particularly useful mammalian cell lines include VERO (ATCC CCL 81), HeLa cells (ATCC CCL 2.1, ATCC CCL 2.2), W138, COS, jurkat, CEM, 293 (human embryonic kidney cell line ATCC CRL 1573) and MDCK cell lines. Most preferably, the mammalian cell line employed to prepare a mammalian cell nuclear extract for purposes of isolating the herein described binding protein, TRP-185, are HeLa cells or HeLa cell lines.

Employing the above described process or method, a TRP-185 TAR binding protein preparation having a purity of about 3,000 fold, and a high yield of about 10–15% is provided from a HeLa cell nuclear extract. The high yield provided by the preparation as described herein presents a significant advantage of the present invention over the art, as using other preparation schemes (which include an S-300 column), results in up to a 95% loss of protein (inventors unpublished observations).

In still another aspect of the invention, a method for preparing a cellular protein having binding affinity for an HIV TAR region is provided. This method comprises the steps of preparing a nuclear extract having HIV TAR RNA binding activity from mammalian cells, fractionating the nuclear extract to select for HIV TAR binding activity, and isolating an HIV TAR binding element to provide the cellular protein, wherein said protein has a molecular weight of about 185 kD.

In a particularly preferred embodiment of the present invention processes and methods for isolating a TAR binding protein comprises, fractionating the nuclear extract by chromatographing the nuclear extract on immobilized heparin, such as heparin agarose, eluting the chromatographed nuclear extract by potassium chloride, or other buffer, to obtain TAR active binding fractions, selecting and dialyzing TAR active binding fractions, chromatographing the active fractions on an anionic separation gel, for example an HTP Biogel, precipitating with increasing concentrations of ammonium sulfate, or other precipitating buffer, and selecting active TAR-binding fractions, applying the active TAR-binding fractions on molecular weight separation gel, such as a Superdex 200 FPLC column, collecting active TAR-binding fractions and applying a dialyzate of the active fractions to another molecular weight separation matrix or gel, for example a Bio Rex column, collecting active TAR-binding fractions and applying a dialyzate of the active fractions to an anionic separation gel, such as Dextran Blue Sepharose column, collecting active TAR-binding fractions and applying a dialyzate thereof to another anionic separation gel, such as a Mono Q FPLC column, collecting active TAR-binding fractions and applying a dialyzate of selected washed fractions to a continuous sucrose gradient, and isolating a nucleic acid binding element having a molecular weight of between about 175 to about 190 kD as determined by a continuous sucrose gradient having TAR region binding activity.

A number of methods for isolating nuclear extracts may be used with the present invention. A particularly prefered method includes the preparation of a nuclear extract according to the steps of lysing a cell pellet of mammalian cells susceptible to infection by HIV, such as HeLa cells, such as with a Dounce homogenizer, isolating nuclei from the cells, lysing the nuclei, centrifuging the lysate to obtain a supernatant, and dialyzing the supernatant to obtain a nuclear extract having a binding activity for a TAR region of nucleic acid.

Nucleic Acids

A preferred embodiment of the present invention is a purified nucleic acid segment that encodes a nucleic acid binding protein TRP-185 having an amino acid sequence in accordance with SEQ ID NO:2. As used herein, the terms "nucleic acid segment" and "DNA segment" are used interchangeably and refer to a DNA molecule which has been isolated free of total genomic DNA of a particular species. Therefore, a "purified" DNA or nucleic acid segment as used herein, refers to a DNA segment which contains an TRP-185 coding sequence yet is isolated away from, or purified free from, total genomic DNA, for example, total human genomic DNA. Included within the term "DNA segment", are DNA segments and smaller fragments of such segments, and also recombinant vectors, including, for example, plasmids, cosmids, phage, viruses, and the like.

Another embodiment of the present invention is a purified nucleic acid segment, further defined as including a nucleotide sequence in accordance with SEQ ID NO:1. In a more preferred embodiment the purified nucleic acid segment consists essentially of the nucleotide sequence of SEQ ID NO:1. Such nucleotide sequences are more particularly defined as being substantially free of nucleic acids not encoding the TRP-185 protein.

Similarly, a DNA segment comprising an isolated or purified TRP-185 gene refers to a DNA segment including TRP-185 coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences, cDNA sequences or combinations thereof. "Isolated substantially away from other coding sequences" means that the gene of interest, in this case the TRP-185 encoding gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences which encode an TRP-185 gene, that includes within its amino acid sequence an amino acid sequence in accordance with SEQ ID NO:2. Moreover, in other particular embodiments, the invention concerns isolated DNA segments and recombinant vectors incorporating DNA sequences which encode a gene that includes within its amino acid sequence the amino acid sequence of an TRP-185 gene corresponding to human TRP-185.

Another preferred embodiment of the present invention is a purified nucleic acid segment that encodes a protein in accordance with SEQ ID NO:2, further defined as a recombinant vector. As used herein the term, "recombinant vector" refers to a vector that has been modified to contain a nucleic acid segment that encodes an TRP-185 protein, or fragment thereof. The recombinant vector may be further defined as an expression vector comprising a promoter operatively linked to said TRP-185 encoding nucleic acid segment. In a most preferred embodiment the recombinant vector comprises a nucleic acid sequence in accordance with SEQ ID NO:1.

A further preferred embodiment of the present invention is a host cell, made recombinant with a recombinant vector comprising a TRP-185 gene. The recombinant host cell may be a prokaryotic or a eukaryotic cell. In a more preferred embodiment, the recombinant host cell is a eukaryotic cell. As used herein, the term "engineered" or "recombinant" cell is intended to refer to a cell into which a recombinant gene, such as a gene encoding TRP-185, has been introduced. Therefore, engineered cells are distinguishable from naturally occurring cells which do not contain a recombinantly introduced gene. Thus, engineered cells are cells having a gene or genes introduced through the hand of man. Recombinantly introduced genes will either be in the form of a cDNA gene (i.e., they will not contain introns), a copy of a genomic gene, or will include genes positioned adjacent to a promoter not naturally associated with the particular introduced gene, or combinations thereof. In a related embodiment the present invention also includes recombinant hosts or vectors, that may be further defined as a *Saccharomyces cerevisiae*, or *Escherichia coli* host; or a *Baculovirus*, or *Vaccinia* virus vector.

Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventors do not exclude the possibility of employing a genomic version of a particular gene where desired.

In certain embodiments, the invention concerns isolated DNA segments and recombinant vectors which encode a protein or peptide that includes within its amino acid sequence an amino acid sequence essentially as set forth in SEQ ID NO:2. Naturally, where the DNA segment or vector encodes a full length TRP-185 protein, or is intended for use in expressing the TRP-185 protein, the most preferred sequences are those which are essentially as set forth in SEQ ID NO:2.

The term "a sequence essentially as set forth in SEQ ID NO:2" means that the sequence substantially corresponds to a portion of SEQ ID NO:2 and has relatively few amino acids which are not identical to, or a biologically functional equivalent of, the amino acids of SEQ ID NO:2. The term "biologically functional equivalent" is well understood in the art and is further defined in detail herein, as a gene having a sequence essentially as set forth in SEQ ID NO:2, and that is associated with binding to the viral TAR RNA region of HIV. Accordingly, sequences which have between about 70% and about 80%; or more preferably, between about 81% and about 90%; or even more preferably, between about 91% and about 99%; of amino acids which are identical or functionally equivalent to the amino acids of SEQ ID NO:2 will be sequences which are "essentially as set forth in SEQ ID NO:2".

In certain other embodiments, the invention concerns isolated DNA segments and recombinant vectors that include within their sequence a nucleic acid sequence essentially as set forth in SEQ ID NO:1. The term "essentially as set forth in SEQ ID NO:1", is used in the same sense as described above and means that the nucleic acid sequence substantially corresponds to a portion of SEQ ID NO:1, and has relatively few codons which are not identical, or functionally equivalent, to the codons of SEQ ID NO:1. The term "functionally equivalent codon" is used herein to refer to codons that encode the same amino acid, such as the six codons for arginine or serine, as set forth in Table 1, and also refers to codons that encode biologically equivalent amino acids.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences which have between about 70% and about 80%; or more preferably, between about 80% and about 90%; or even more preferably, between about 90% and about 99%; of nucleotides which are identical to the nucleotides of SEQ ID NO:1 will be sequences which are "essentially as set forth in SEQ ID NO:1" Sequences which are essentially the same as those set forth in SEQ ID NO:1 may also be functionally defined as sequences which are capable of hybridizing to a nucleic acid segment containing the complement of SEQ ID NO:1 under relatively stringent conditions. Suitable relatively stringent hybridization conditions will be well known to those of skill in the art and are clearly set forth herein, for example conditions for use with northern blot analysis, and as described in the preferred embodiments and in Examples 1, 4 and 12, and, specifically those, conditions used to generate the data in FIG. 15.

TABLE 1

CODON DEGENERACY

| Amino Acids | | | | | | | |
|---|---|---|---|---|---|---|---|
| Alanine | Ala | A | GCA | GCC | GCG | GCU | |
| Cysteine | Cys | C | UGC | UGU | | | |
| Aspartic acid | Asp | D | GAC | GAU | | | |
| Glutamic acid | Glu | E | GAA | GAG | | | |
| Phenylalanine | Phe | F | UUC | UUU | | | |
| Glycine | Gly | G | GGA | GGC | GGG | GGU | |
| Histidine | His | H | CAC | CAU | | | |
| Isoleucine | Ile | I | AUA | AUC | AUU | | |
| Lysine | Lys | K | AAA | AAG | | | |
| Leucine | Leu | L | UUA | UUG | CUA | CUC | CUG CUU |
| Methionine | Met | M | AUG | | | | |
| Asparagine | Asn | N | AAC | AAU | | | |
| Proline | Pro | P | CCA | CCC | CCG | CCU | |
| Glutamine | Gln | Q | CAA | CAG | | | |
| Arginine | Arg | R | AGA | AGG | CGA | CGC | CGG CGU |
| Serine | Ser | S | AGC | AGU | UCA | UCC | UCG UCU |
| Threonine | Thr | T | ACA | ACC | ACG | ACU | |
| Valine | Val | V | GUA | GUC | GUG | GUU | |
| Tryptophan | Trp | W | UGG | | | | |
| Tyrosine | Tyr | Y | UAC | UAU | | | |

Naturally, the present invention also encompasses DNA segments which are complementary, or essentially complementary, to the sequence set forth in SEQ ID NO:1. Nucleic acid sequences which are "complementary" are those which are capable of base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment of SEQ ID NO:1 under relatively stringent conditions such as those described herein in the detailed description of the preferred embodiments and in EXAMPLES 9 and 12.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared which include a short stretch complementary to SEQ ID NO:1, such as about 10 to 15 or 20, 30, or 40 or so nucleotides, and which are up to 10,000 or 5,000 base pairs in length, with segments of 3,000 being preferred in certain cases. DNA segments with total lengths of about 5,000, 1,000, 500, 200, 100 and about 50 base pairs in length are also contemplated to be useful.

A preferred embodiment of the present invention is a nucleic acid segment which comprises at least a 14–20 nucleotide long stretch which corresponds to, or is complementary to, the nucleic acid sequence of SEQ ID NO:1. In a more preferred embodiment the nucleic acid is further defined as comprising at least a 25 nucleotide long stretch, a 30 nucleotide long stretch, 50 nucleotide long stretch, 100 nucleotide long stretch, a 200 nucleotide long stretch, a 500 nucleotide long stretch, a 1,000 nucleotide long stretch, a 3,000 nucleotide long stretch, or at least a full length (5173 nucleotides) cDNA in accordance with SEQ ID NO:1 which corresponds to, or is complementary to, the nucleic acid sequence of SEQ ID NO:1. The nucleic acid segment may be further defined as having the nucleic acid sequence of SEQ ID NO:1.

A related embodiment of the present invention is a nucleic acid segment which comprises at least a 14–20 nucleotide long stretch which corresponds to, or is complementary to, the nucleic acid sequence of SEQ ID NO:1, further defined as comprising a nucleic acid fragment of up to 10,000 basepairs in length. A more preferred embodiment is a nucleic acid fragment comprising from 14–20 nucleotides of SEQ ID NO:1 up to 5,000 basepairs in length, 3,000 basepairs in length, 1,000 basepairs in length, 500 basepairs in length, or 100 basepairs in length. Naturally, it will also be understood that this invention is not limited to the particular nucleic acid and amino acid sequences of SEQ ID NOS:1 and 2. Recombinant vectors and isolated DNA segments may therefore variously include the TRP-185 coding regions themselves, coding regions bearing selected alterations or modifications in the basic coding region, or they may encode larger polypeptides which nevertheless include TRP-185-coding regions or may encode biologically functional equivalent proteins or peptides which have variant amino acids sequences.

The DNA segments of the present invention encompass biologically functional equivalent TRP-185 proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the TRP-185 protein or to test TRP-185 mutants in order to examine viral TAR RNA region binding promoting activity and potential at the molecular level.

Another preferred embodiment of the present invention is a purified composition comprising a polypeptide having an amino acid sequence in accordance with SEQ ID NO:2. The term "purified" as used herein, is intended to refer to an TRP-185 protein composition, wherein the TRP-185 protein is purified to any degree relative to its naturally-obtainable state, i.e., in this case, relative to its purity within a eukaryotic cell nuclear extract. A preferred cell for the isolation of TRP-185 protein is a HeLa cell, however, TRP-185 protein may also be isolated from recombinant cells, tissues, isolated subpopulation of tissues, and the like, as will be known to those of skill in the art, in light of the present disclosure. A purified TRP-185 protein composition therefore also refers to a polypeptide having the amino acid sequence of SEQ ID NO:2, free from the environment in which it may naturally occur.

If desired, one may also prepare fusion proteins and peptides, e.g., where the TRP-185 coding regions are aligned within the same expression unit with other proteins or peptides having desired functions, such as for purification or immunodetection purposes (e.g., proteins which may be purified by affinity chromatography and enzyme label coding regions, respectively).

Turning to the expression of the TRP-185 gene whether from cDNA based or genomic DNA, one may proceed to prepare an expression system for the recombinant preparation of TRP-185 protein. The engineering of DNA segment (s) for expression in a prokaryotic or eukaryotic system may be performed by techniques generally known to those of skill in recombinant expression. For example, a TRP-185-GST (glutathione-S-transferase) fusion protein provides a convenient means of bacterial expression. However, it is believed that virtually any expression system may be employed in the expression of TRP-185.

TRP-185 may be successfully expressed in eukaryotic expression systems, however, the inventors aver that bacterial expression systems can be used for the preparation of TRP-185 for all purposes. The cDNA for TRP-185 may be separately expressed in bacterial systems, with the encoded proteins being expressed as fusions with β-galactosidase, avidin, ubiquitin, Schistosoma japonicum glutathione β-transferase, epitope-tags and the like. It is believed that bacterial expression will ultimately have advantages over eukaryotic expression in terms of ease of use and quantity of materials obtained thereby.

It is proposed that transformation of host cells with DNA segments encoding the TRP-185 will provide a convenient means for obtaining an TRP-185 protein. It is also proposed that cDNA, genomic sequences, and combinations thereof, are suitable for eukaryotic expression, as the host cell will, of course, process the genomic transcripts to yield functional mRNA for translation into protein.

Another embodiment is a method of preparing a TRP-185 protein composition comprising growing recombinant host cell comprising a vector that encodes a protein which includes an amino acid sequence in accordance with SEQ ID NO:2, under conditions permitting nucleic acid expression and protein production followed by recovering the protein so produced. The host cell, conditions permitting nucleic acid expression, protein production and recovery, will be known to those of skill in the art, in light of the present disclosure of the TRP-185 gene.

It is similarly believed that almost any eukaryotic expression system may be utilized for the expression of TRP-185, e.g., baculovirus-based, glutamine synthase-based, dihydrofolate reductase-based systems, or the like, could be employed. For expression in this manner, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter.

Where eukaryotic expression is contemplated, one will also typically desire to incorporate into the transcriptional unit 5 which includes the TRP-185 gene, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

It is contemplated that virtually any of the commonly employed host cells can be used in connection with the expression of TRP-185 in accordance herewith. Examples include cell lines typically employed for eukaryotic expression such as 239, AtT-20, HepG2, VERO, HeLa, Jurkat, CHO, WI 38, BHK, COS-7, RIN and MDCK cell lines.

In yet another preferred embodiment the present invention also provides for a method of detecting a nucleic acid species that is capable of hybridizing to a nucleic acid segment in accordance with SEQ ID NO:1. The method for detecting the nucleic acid species comprises the steps of obtaining a nucleic acid sample and contacting the sample with a nucleic acid segment in accordance with SEQ ID NO:1 under conditions effective to allow hybridization to form a complex. As used herein the phrase "obtaining a nucleic acid sample" is used to describe nucleic acid samples located both within intact cells, for example, a cell sample for in situ hybridization, and of nucleic acids that have been isolated away from cells. Naturally, it is understood that nucleic acids encompass the multiple forms of RNA as well as DNA samples, and are isolateable as described above, and as known to those of skill in the art in light of the present disclosure. In a most preferred embodiment the nucleic acid segment comprises a detectable label that is enzymatic-, fluorescent-, or radio-, or chemiluminescent-labelled.

Those of skill in the art will, in light of the present disclosure, be able to label TRP-185 coding nucleic acids, or fragments thereof, for detection. Techniques for use in the detection of nucleic acids, such as, in situ hybridization, southern and northern blotting, pulse-field gel electrophoresis, nuclease protection assays, unblots, and the like, will be known to those of skill in the art, in light of the present disclosure. The "conditions effective to allow" nucleic acid hybridization, will also be known to those of skill in the art, and as disclosed herein in preferred embodiments, and as described in Sambrook et al.[58]. Also disclosed herein, are the means for detecting and quantitating increases in TRP-185 gene expression levels from clonal and mixed cell populations, such as cell lines and tissues, as disclosed for the generation of FIG. 15.

A target nucleic acid for use in a method of detecting the TRP-185 of the present invention, are target nucleic acids that contacted when located within a cell. The detection of nucleic acids found within cells is accomplished by in situ hybridization. The cells for use with in situ hybridization may be isolated from a solid tumor, a dispersed tumor, or from cells grown in tissue culture. As will be known to those of skill in the art, the cells are prepared for hybridization by fixation, e.g. chemical fixation, and placed in conditions that allow for the hybridization of a detectable probe with nucleic acids located within the fixed cell.

In an alternative embodiment the target nucleic acids are separated from the cell prior to contact. A wide variety of methods for isolating target nucleic acids are contemplated, such as cesium chloride gradient centrifugation, chromatography (ion, affinity, magnetic), phenol extraction, and the like. Furthermore, the isolated target nucleic acids can be detected following electrophoretic separation and immobilization onto a solid matrix, as is the case with southern, northern, and pulse-field electrophoresis, or directly in gel as in the case of unblots. The nucleic acids may also be contacted prior to electrophoretic separation as in the case of nuclease protection assays, and detected using the sequence in accordance with SEQ ID NO:1, or fragments thereof.

Antibodies

In another aspect, the present invention contemplates an antibody that is immunoreactive with a polypeptide of the invention. An antibody can be a polyclonal or a monoclonal antibody. In a preferred embodiment, an antibody is a monoclonal antibody. Means for preparing and characterizing antibodies are well known in the art (See, e.g., Antibodies "A Laboratory Manual, E. Howell and D. Lane, Cold Spring Harbor Laboratory, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

Antibodies, both polyclonal and monoclonal, specific for the TRP-185 of the present invention may be prepared using conventional immunization techniques, as will be generally known to those of skill in the art. A composition containing antigenic epitopes of the TRP-185 sequences, isolated TRP-185, or fragments thereof can be used to immunize one or more experimental animals, such as a rabbit or mouse, which will then proceed to produce specific antibodies against TRP-185. Polyclonal antisera may be obtained, after allowing time for antibody generation, simply by bleeding the animal and preparing serum samples from the whole blood.

To obtain monoclonal antibodies, one would also initially immunize an experimental animal, often preferably a mouse, with a purified TRP-185 composition. One would then, after a period of time sufficient to allow antibody generation, obtain a population of spleen or lymph cells from the animal. The spleen or lymph cells can then be fused with cell lines, such as human or mouse myeloma strains, to produce antibody-secreting hybridomas. These hybridomas may be isolated to obtain individual clones which can then be screened for production of antibody to the desired TRP-185 protein.

Following immunization, spleen cells are removed and fused, using a standard fusion protocol (see, e.g., The Cold Spring Harbor Manual for Hybridoma Development, incorporated herein by reference) with plasmacytoma cells to produce hybridomas secreting monoclonal antibodies against TRP-185. Hybridomas which produce monoclonal antibodies to the selected antigens are identified using standard techniques, such as ELISA and Western blot methods.

Hybridoma clones can then be cultured in liquid media and the culture supernatants purified to provide the TRP-185-specific monoclonal antibodies. In general, monoclonal antibodies to the TRP-185 antigen can be used in both the diagnosis and treatment of HIV infections. It is proposed that the monoclonal antibodies of the present invention will find useful application in standard immunochemical procedures, such as ELISA and Western blot methods, as well as other procedures which may utilize antibody specific to common or allelically distinct TRP-185 epitopes. These TRP-185-specific monoclonal antibodies are anticipated to be useful in various ways for the treatment of TRP-185 infections through, for example, their application in immunodetection procedures.

Additionally, it is proposed that monoclonal antibodies specific to the particular TRP-185 may be utilized in other useful applications. For example, their use in immunoabsorbent protocols may be useful in purifying native or recombinant TRP-185 species or variants thereof.

In general, both poly- and monoclonal antibodies against TRP-185 may be used in a variety of embodiments. For example, they may be employed in antibody cloning protocols to obtain cDNAs or genes encoding related proteins. They may also be used in inhibition studies to analyse the effects of TRP-185 in cells or animals. Anti-TRP-185 antibodies will also be useful in immunolocalization studies to analyse the distribution of TRP-185 during various cellular events, for example, to determine the intracellular localization and distribution of TRP-185 during the presence or absence of HIV infection, as well as during disease progression. A particularly useful application of such antibodies is in purifying native or recombinant TRP-185, for example, using an antibody affinity column. The operation of all such immunological techniques will be known to those of skill in the art in light of the present disclosure.

Immunoassay

The present invention in still another aspect defines an immunoassay for the detection of an antibody specific for a nucleic acid binding element TRP-185 in a biological sample. In one particular embodiment of the immunoassay, the immunoassay comprises; preparing a cellular binding protein specific for TAR RNA and which regulates HIV gene expression to provide a TRP-185 antigen, incubating the TRP-185 antigen with the biological sample for a sufficient time to permit binding between antigen and antibody present in said biological sample, and determining the presence of bound antibody by contacting the incubate of the antigen and antibody with a detectably labeled antibody specific for the anti-TRP-185 antibody, wherein the presence of anti-TRP-185 antibody in the biological sample is detectable as the measure of the detectably labeled antibody from the biological sample.

By way of example, the antibody may be labeled with any of a variety of detectable molecular labeling tags. Such include, an enzyme-linked antibody, a fluorescent-tagged antibody, or a radio-labelled antibody. In one particular embodiment of the described immunoassay, the TRP-185 is prepared from mammalian cell nuclei or a recombinant host expressing said TRP-185 antigen. In the described immunoassay, the presence of anti-TRP-185 antibody is diagnostic of an HIV viral infection in the animal. Use of a cofactor-exposed TRP-185 antigen and a cofactor unexposed TRP-185 antigen in the immunoassay may also provide a method for monitoring the progression of an HIV infection in an animal, as it is postulated that the infected state of the animal will be reflected in the type of reactive antibody in the animal to each of these different TRP-185 preparations as antigen.

In still another aspect of the present invention, a nucleic acid sequence or fragment thereof encoding a cellular protein TRP-185 which binds an HIV TAR RNA is provided. The nucleic acid segment or fragment thereof is isolatable from most preferably human chromosomal DNA. The nucleic acid segment or fragment thereof is even more specifically defined as encoding an antigenic protein capable of producing an in vivo immunogenic response to the TRP-185 cellular protein. The nucleic acid segment or fragment thereof may also be defined as a cDNA sequence complementary to a TRP-185 mRNA.

The present invention also includes a recombinant DNA vector which includes a DNA sequence encoding a nucleic acid binding element capable of binding with high affinity to a TAR RNA region in the presence of at least one cofactor. The nucleic acid binding element is of cellular origin and has a molecular weight of between about 175 to about 190 kD. The recombinant DNA vector may also be described as including a DNA sequence which is a cDNA sequence complementary to a TRP-185 mRNA or a fragment thereof. The recombinant DNA vector of the present invention will also be capable of replication in a host. A recombinant host bearing a recombinant DNA vector may also be prepared. The DNA sequence of the recombinant DNA vector may be defined further as a cDNA sequence which is complementary to a TRP-185 mRNA. The recombinant host should also be capable of expressing the DNA segment to produce a TRP-185 cellular protein. By way of example, the recombinant host of the present invention may be *Saccharomyces cerevisiae, Escherichia coli, Baculovirus* or a *Vaccinia* Virus host.

Recombinant methods may also be utilized in obtaining the cellular protein having the binding affinity for nucleic acid sequences characteristic of the TAR RNA region of the HIV long terminal repeat. One particular embodiment for preparing a recombinant TRP-185 cellular protein comprises preparing a recombinant host bearing a recombinant DNA segment encoding a cellular TRP-185 protein capable of binding a TAR sequence; said recombinant host being capable of expressing the protein, culturing the recombinant host to produce TRP-185, and separating the TRP-185 from the recombinant host.

Still another aspect of the invention includes an antibody specific for a TRP-185 cellular protein having binding affinity for a TAR RNA region. The antibody may be either a monoclonal antibody (such as that produced by a hybridoma cell line) or a polyclonal antibody. Where the antibody is a monoclonal antibody, it may be defined further as having an IgG or IgM isotype.

The antibody of the present invention may be prepared by employing the TRP-185 cellular protein described herein together with a standard immunization protocols known to those in the art (see Example 3).

In still another embodiment of the invention, a hybridoma cell line which produces a monoclonal antibody which specifically binds a TRP-185 cellular protein is provided. Most particularly, the hybridoma cell line is a murine hybridoma cell line produced by immunizing a mouse or a rat with a cellular protein TRP-185 which binds an HIV TAR mRNA, isolating anti-TRP-185 antibody producing cells from the immunized mouse, and fusing the antibody producing cells with a neo-plastic murine cell line to obtain a murine hybridoma cell line.

Another aspect of the present invention provides a therapeutic agent for the treatment of HIV or HTLV infection in an animal. The therapeutic agent comprises an admixture of an inhibitor of a TRP-185 cellular protein in a pharmaceutically acceptable excipient. Most preferably, the therapeutic agent will be formulated so as to be suitable for administration as a parental formulation or as a capsule (for oral administration).

The active compounds may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus by additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral prophylaxis the polypeptide may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

In still another aspect of the present invention, an RNA binding complex is provided. The RNA binding complex may be particularly useful in characterizing the molecular events of gene expression. In one particular embodiment, the RNA binding complex comprises a TRP-185 cellular protein capable of binding a TAR RNA region of HIV, at least one cofactor capable of facilitating the binding of the TRP-185 to a TAR RNA, and a volume of TAR RNA sufficient to bind the TRP-185. Most preferably, the cofactor is an about 100 kD protein isolatable from a mammalian cell extract. Most preferably, the colactor and the TRP-185 cellular protein are isolated from a HeLa cell nuclear cell extract as previously described hereinabove. It is anticipated that the described RNA binding complex may be used as a laboratory and candidate substance screening reagent, most particularly in the characterization of vital and cellular gene expression, and inhibitors thereof.

In an alternative embodiment the RNA binding complex may be used to screen compounds that are able to inhibit the TRP-185 to TAR RNA interaction. It is also envisioned that compounds that alter the effect of the co-factors described herein may be useful for inhibiting the TRP-185 to TAR RNA interaction.

Assays for Candidate Substances

In still further embodiments, the present invention concerns a method for identifying new TRP-185-TAR RNA inhibitory compounds, which may be termed as "candidate substances." It is contemplated that this screening technique will prove useful in the general identification of any compound that will serve the purpose of inhibiting the interaction of TRP-185 with the TAR region of HIV, HTLV and other Lentivirus family members. It is further contemplated that useful compounds in this regard will in no way be limited to proteinaceous or peptidyl compounds, since the candidate substances may also affect the role of the co-factors described herein. In fact, it may prove to be the case that the most useful pharmacological compounds for identification through application of the screening assay will be non-peptidyl in nature and serve to inactivate the TRP-185 to TAR interaction through a tight binding or other chemical interaction.

Accordingly, in screening assays to identify pharmaceutical agents which disrupt RNA complex formation, it is proposed that compounds isolated from natural sources such as plants, animals or even sources such as marine, forest or soil samples, may be assayed for the presence of potentially useful pharmaceutical agents. It will be understood that the pharmaceutical agents to be screened could also be derived from chemical compositions or man-made compounds. In important aspects, the candidate substances may be anti-TRP-185 antibodies, including polyclonal and monoclonal antibodies. The suspected agents could also include proteins and peptides, such as those derived from recombinant DNA technology or by other means, including peptide synthesis. The active compounds may include fragments or parts of naturally-occurring compounds or may be only found as active combinations of known compounds which are otherwise inactive.

In these embodiments, the present invention is directed to a method for determining the ability of a candidate substance to inhibit the TRP-185-TAR sequence interaction, the method including generally the steps of:

(a) obtaining a RNA binding complex comprising a TRP-185 protein and co-factors capable of binding to TAR nucleic acid sequences;

(b) admixing a candidate substance with the RNA binding complex in the presence of target TAR sequences; and (c) determining the ability of the RNA binding complex to bind TAR nucleic acid sequences in the presence of the candidate substance.

An important aspect of the candidate substance screening assay of the present invention is the ability to prepare a native or recombinant TRP-185 enzyme composition in a relative purified form, for example, in a manner as discussed above. This is an important aspect of the candidate substance screening assay in that without at least a relatively purified preparation, one will not be able to assay specifically for inhibition of TAR sequence binding by TRP-185, as opposed to the effects of the inhibition upon other substances in the extract which then might affect the binding. In any event, the successful isolation of the TRP-185 protein now allows for the first time the ability to identify new compounds which can be used for inhibiting this HIV TAR region directed activation of HIV.

The candidate screening assay is quite simple to set up and perform, and is related in many ways to the assay discussed above for determining enzyme activity. Thus, after obtaining a relatively purified preparation of the TRP-185, either from native or recombinant sources, one will desire to simply admix a candidate substance with the TRP-185 TAR RNA or DNA sequence containing preparation, preferably under conditions which would allow the TRP-185 to perform its binding function but for inclusion of a inhibitory substance. Thus, for example, one will typically desire to include within the admixture an amount of the known co-factor. In this fashion, one can measure the ability of the candidate substance to reduce TRP-185 TAR binding activity relatively in the presence of the candidate substance.

Any method may generally be employed to determine TRP-185 protein binding to TAR nucleic acid sequences. Preferred methods will be those in which the target TAR coding nucleic acids incorporates, or is conjugated to, a label, such as an enzymatic, chemical or radiolabel, or incorporates one of the ligands of a two ligand-based detection system such as the avidin/biotin system. For ease and safety, the use of enzymatic labels, such as, for example, horse radish peroxidase, urease or alkaline phosphatase is preferred. In such cases, a colorimetric indicator substrate would be employed to provide a means visible to the human eye, or spectrophotometrically, to identify specific hybridization with labelled target sequences.

In still further embodiments, the present invention is concerned with a method of inhibiting TRP-185 TAR sequence binding which includes subjecting a RNA binding complex to an effective concentration of a candidate inhibitor such as one of the family of protein or non-proteinaceous compounds discussed above, or with a candidate substance identified in accordance with the candidate screening assay embodiments. This is, of course, an important aspect of the invention in that it is believed that by inhibiting the binding of TRP-185 to TAR nucleic acid sequences, one will be enabled to treat various aspects of retrovital infection, including the HIV virus and related members of the *Lentivirus* family. It is believed that the use of such inhibitors to block TAR region activation will serve to treat cells that can be, or have already been infected with a retrovirus, such as HIV, and may be useful by themselves or in conjunction with other therapies, including the use of nucleic acid homologs and the like.

Test Pack

In still another embodiment, a diagnostic test pack for the detection of anti-TRP-185 antibody in a biological sample is provided. In one preferred embodiment, the diagnostic test pack comprises in packaged combination a carrier means adapted to receive at least three container means in close confinement therewith, a first container means including a TRP-185 cellular protein capable of binding a TAR RNA and having molecular weight of about 185 kD, a second container means including a quantity of an unlabeled antibody having specific binding affinity for the TRP-185 cellular protein, a third container means including a quantity of a detectably labeled antibody specific for binding with the anti-TRP-185 antibody, and at least one microtiter plate.

More specifically, the detectably labeled antibody of the described test-pack is an enzyme-linked antibody, a fluorescent tagged antibody or a radio-labeled antibody. By way of example, radiolabels such as $^{125}I$, $^{3}H$ and others may be used to label the antibody.

The test pack in still another embodiment may include a fourth container means having a quantity of a substrate for the enzyme sufficient to produce a visually detectable product, where the antibody of choice is an enzyme-linked antibody. Even more preferably, the antibodies of the diagnostic text pack are monoclonal antibodies specific for the TRP-185 cellular protein. Alternatively, both the unlabeled antibody and the detectably labeled antibody are polyclonal antibodies specific for the TRP-185 cellular protein.

The particular TRP-185 cellular protein of the present invention is expected to be important in the regulation of cellular genes as well as HIV and HTLV genes. Highly purified fractions of the TRP-185 cellular protein have been shown by the inventors to bind strongly to elements of cellular promoters downstream of important "initiation elements" (such as in the adenovirus). This activity demonstrates that the herein isolated TRP-185 cellular protein may have the ability to also regulate other gene promoters.

In particular embodiments of the described therapeutic agents, "inhibitors" of TRP-185 may, in addition to the aforedescribed specific antibodies for TRP-185, include anti-sense DNA, an RNA fragment that preferentially binds the TRP-185 protein, a competitive binding protein for the TAR-RNA binding site, or a protein or a peptide which acts to modify a TRP-185 protein, such as to dephosphorylate the TRP-185 protein to thereby potentially prevent the binding of the TRP-185 to its specific TAR RNA binding site.

In that the present inventors have disclosed the ability of a cellular protein to bind to both upstream and downstream of important promotor elements to a highly conserved region of, for example, the HIV gene, the inventors postulate the particular TRP-185 cellular protein may also bind other "conserved" nucleic acid regions which become activated upon association with a cellular protein, to affect gene expression. These results indicate that TRP-185 binds to conserved regions of DNA known as "initiator sequences".[57] These elements are critical for gene expression of both vital and cellular genes. Thus, TRP-185 may regulate the expression of various cellular genes.

In the aforedescribed method for obtaining the TRP-185 binding protein, preparing a nuclear extract from mammalian cells may be more generically described as disrupting the integrity of these cells and obtaining the nuclei and then disrupting the integrity of the nuclei and using the soluble proteins which bind to TAR RNA in the following steps. Similarly, the steps for fractionating the nuclear extract as described as part of the claimed methods may be more generically described as binding the nuclear extracts to an ion exchange column (i.e., heparin agarose) and eluting with specific concentrations of KCL, dialyzing the proteins contained in the different column fractions eluted from the heparin agarose column (ion exchange column), identifying column fractions which contain protein that binds to TAR RNA using gel retardation analysis, repeating the procedure of binding to different columns containing either CAT ionic or anionic resins, followed by elution, an assaying the fractions using TAR RNA gel retardation (the columns which are used sequentially after the heparin agarose column include hydroxylipitie Biogel, Superdex 20 fast phase liquid chromatography (FPLC), Bio-Rex, Dextran Blue Sepharose, and a mono Q FPLC. The ultimate step in the aforedescribed process as part of steps for fractionating the nuclear extract include centrifuging active protein fractions containing TRP-185 by sucrose gradient sedimentation. Finally, fractions are isolated from the sucrose gradient that have a molecular weight of 175–190 kDa and bind to TAR RNA loop sequences.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

Fractions from chromatography that were active for binding to TAR RNA in gel retardation (FIG. 1A) or UV crosslinking assays (FIG. 1B) are shown. Lanes 1=probe alone; Lane 2=heparin agarose; Lane 3=Sephacryl S-300; Lane 4=mono S FPLC; Lane 5=hydroxylapatite; Lane 6=sucrose gradient TRP 140 pool; Lane 7=Sucrose gradient TRP 185 Pool; Lane 8=Sucrose gradient TRP 185 pool and cofactor (CF) fraction; and Lane 9=cofactor (CF) fraction alone. FIG. 1C: Lane 2 and Lane 3 show UV crosslinking of TRP-185 from the sucrose gradient TRP 185 fraction in the absence (lane 2), or presence (lane 3) of RNase.

FIG. 2A=TRP-185 binding was assayed by gel retardation with fractions 5–19 obtained by analytical sucrose gradient centrifugation. FIG. 2B=These same fractions were also assayed in the presence of cofactors fractions. The positions of the migration of molecule mass markers in the sucrose gradient are shown.

Figure 3E:
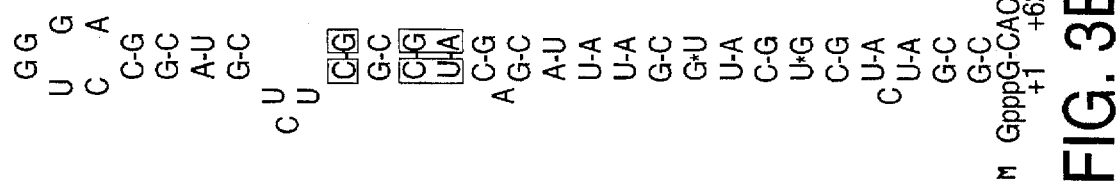
FIG. 3A–FIG. 3J Mutations in the HIV TAR region.
Figure 3D:
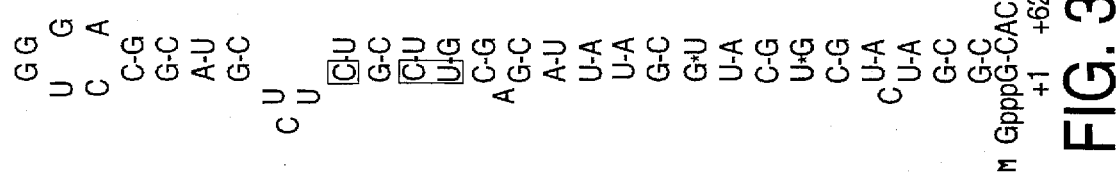
Figure 3C:
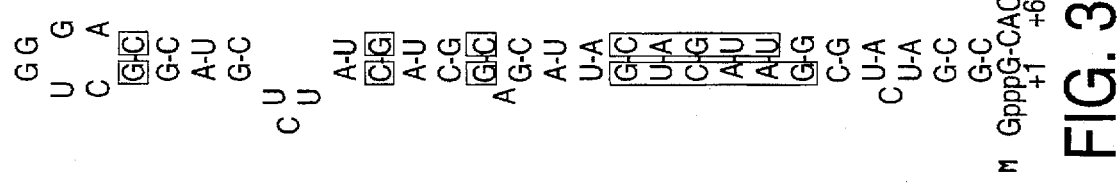
Figure 3B:
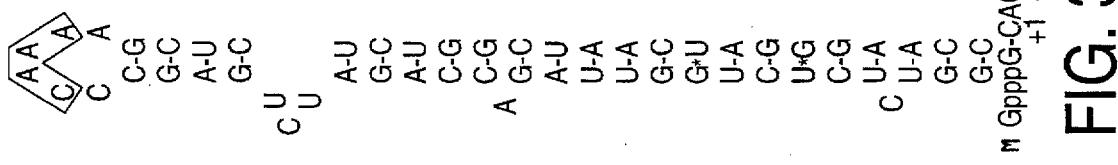
Figure 3A:
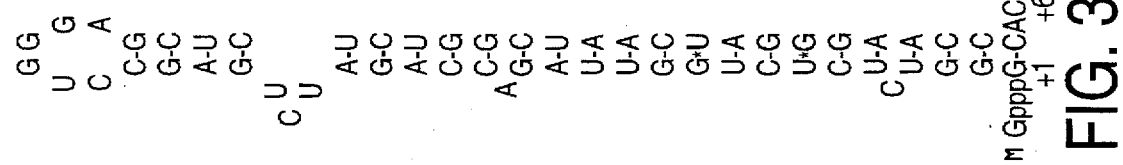
Figure 3J:
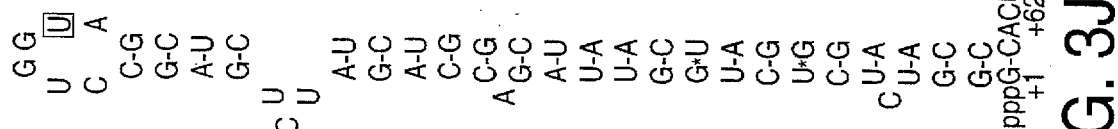
Figure 3I:
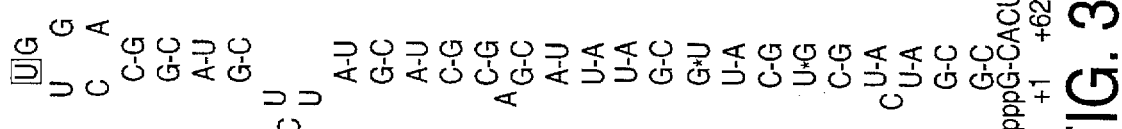
Figure 3H:
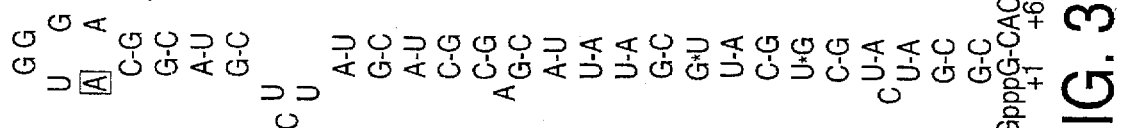
Figure 3G:
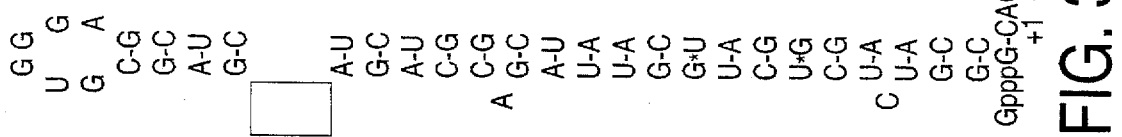
Figure 3F:
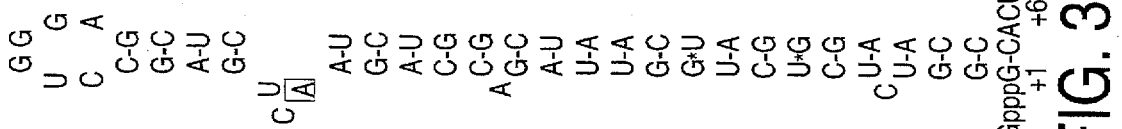

The stem-loop structure of the HIV LTR extending from +1 to 62 is shown for a series of constructs which extend to +80 (Hind III) in the LTR. The (+1/+80) TAR DNA fragments were ligated to a linker encoding the T7 RNA polymerase promoter, the linker-TAR fragments were cloned into pUC19, and RNA transcription from these constructs was performed in vitro with T7 polymerase. The shaded areas indicate the nucleotides substituted and/or deleted in each construct. The constructs include FIG. 3A wild-type, FIG. 3B (+31/+34), FIG. 3C (TAR-sense), FIG. 3D (+19/+22, FIG. 3E (+19/+22)/(+40/+43), FIG. 3E (+23), FIG. 3G Δ(+23/+25), FIG. 3H +30, FIG. 3I 32 , and FIG. 3J +34.

Figure 4A:
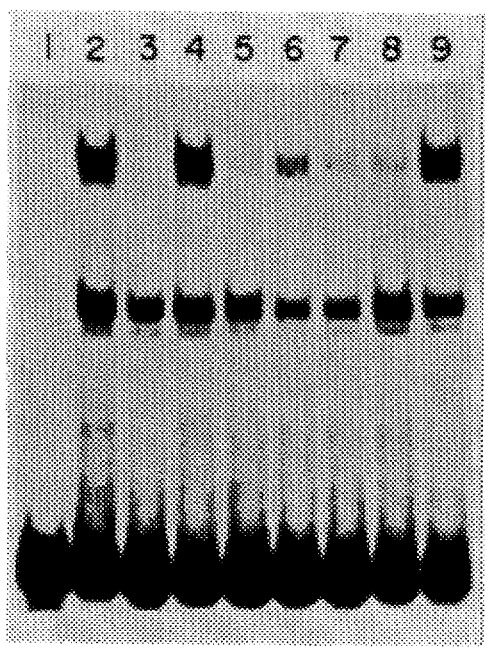
Figure 4B:
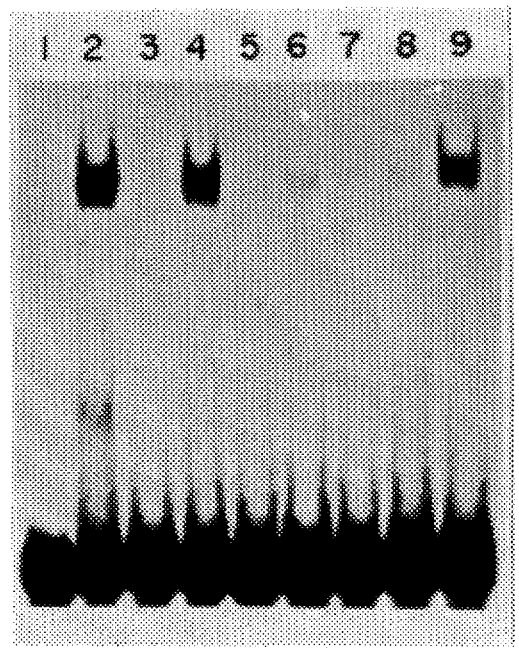
Figure 4C:
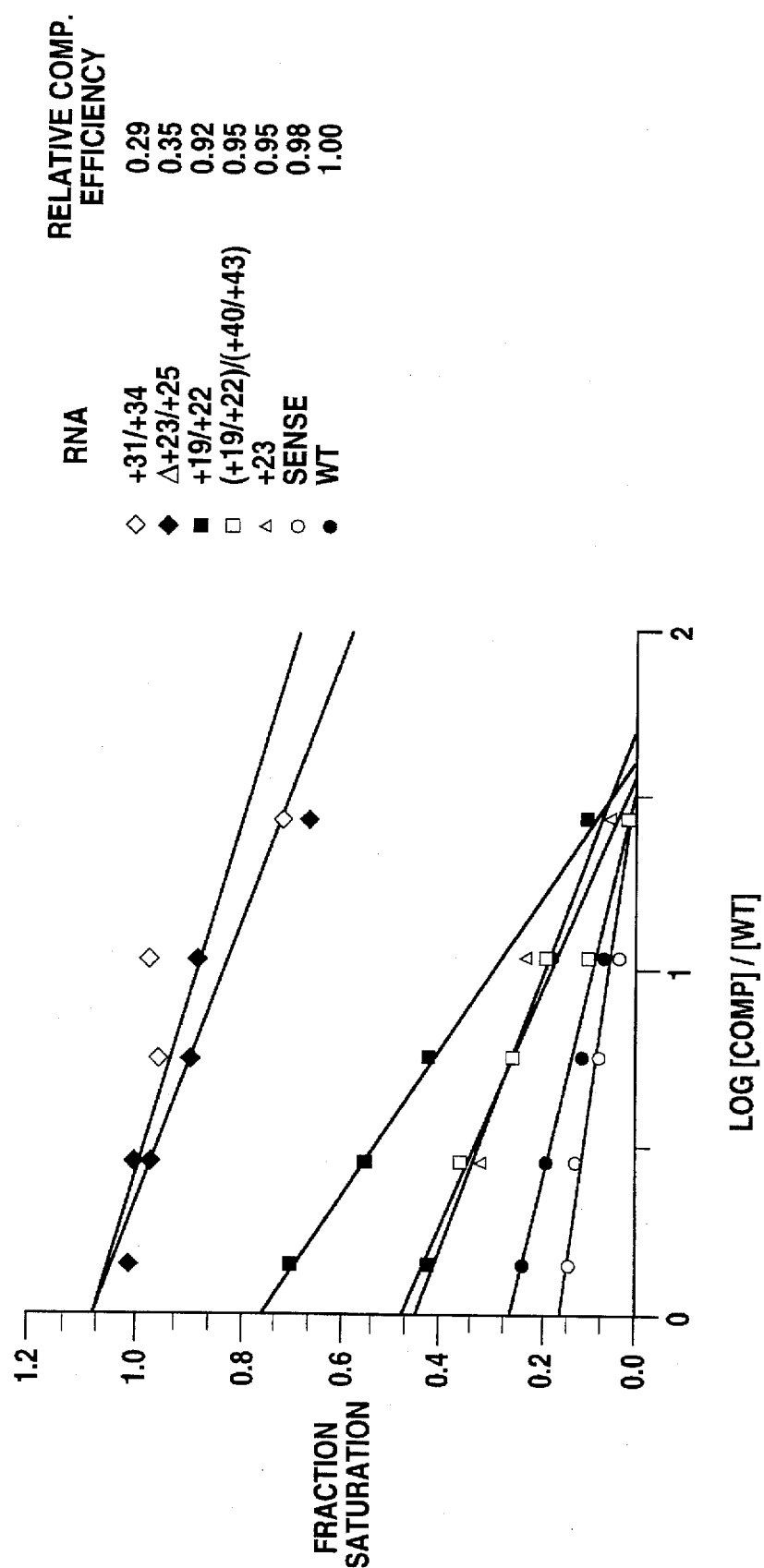

FIGS. 4A, 4B and 4C Competition analysis of TRP-185 and TRP-140 with mutant TAR RNA Gel retardation analysis was performed with internally labeled wild-type TAR RNA and either hydroxylapatite (FIG. 4A or analytical sucrose gradient (FIG. 4B) purified TRP-185 with added cofactors. Lanes include probe alone (lane 1), extract (lane 2), or competition with a 30-fold excess of unlabeled RNA for wild-type (Lane 3); +31/+34 (Lane 4); TAR-sense (Lane 5); 19/+22, (Lane 6); (19/+22) /(+40/+43) (Lane 7); +23 (Lane 8); and Δ(+23/+25) (Lane 9). Binding reactions were performed by mixing various amounts of competitor RNA (0–50 ng) with 1.5 ng of wild-type RNA probe and the added extract. FIG. 4C=data were plotted, and competition curves and relative competition efficiencies were determined.

| RNA | RELATIVE COMP. EFFICIENCY |
|---|---|
| ◊ +31/+34 | 0.29 |
| ♦ _+23/+25 | 0.35 |
| ■ +19/+22 | 0.92 |
| □ (+19/+22)/(+40/+43) | 0.95 |
| _ +23 | 0.95 |
| ° SENSE | 0.98 |
| • WT | 1.00 |

Figures 5A, 5B:
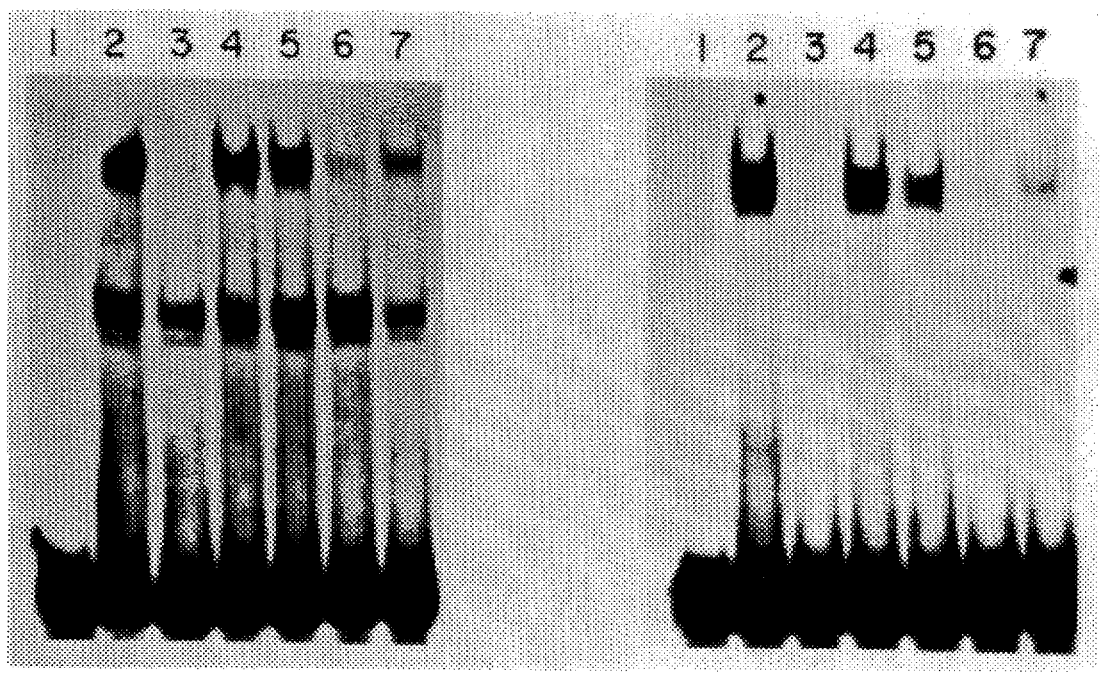
Figure 5C:
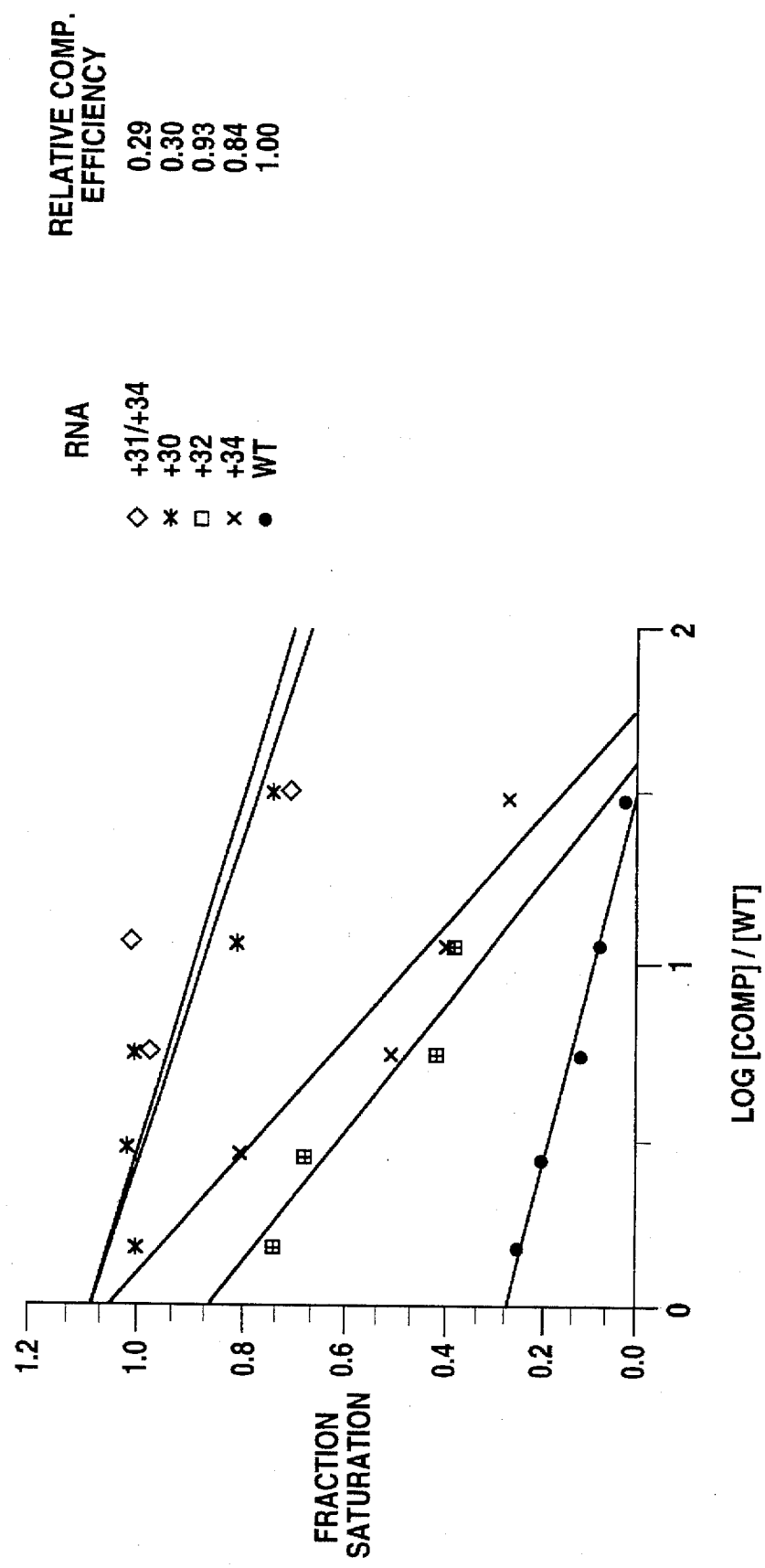

FIGS. 5A, 5B and 5C Competition analysis of TRP-185 and TRP-140 with TAR loop mutants Gel retardation analysis was performed with internally-labeled wild-type TAR RNA using either hydroxylapatite (FIG. 5A) or analytical sucrose gradient (FIG. 5B) purified TRP-185 with added cofactor. Lanes included probe alone (lane 1), with extract (lane 2), or competition with a 30-fold excess of unlabeled RNA for the wild-type (Lane 3), +31/+34 (Lane 4); +30 (Lane 5); +32 (Lane 6); and +34 (Lane 7). FIG. 5C=data were plotted, and competition curves and relative competition efficiencies were determined.

| RNA | RELATIVE COMP. EFFICIENCY |
|---|---|
| ◊ +31/+34 | 0.29 |
| _ +30 | 0.30 |
| _ +32 | 0.93 |
| x +34 | 0.84 |
| • WT | 1.00 |

FIGS. 6A, 6B, 6C, and 6D Binding of tat proteins to wild-type and mutant HIV TAR RNA Both bacterially produced and purified wild-type tat (lanes 1–5) and a mutant tat protein, tat 52/57 (lanes 6–10), were used in gel retardation assays with labeled TAR RNAs corresponding to the wild-type (A), loop substitution mutant +31/+34 (B) , bulge point mutant +23 (C), and bulge deletion mutant +23/+25 (D). The amount of tat protein added to each reaction was as follows: 0 (lanes 1, 6), 1.8 ng (lanes 2, 7), 3.6 ng (lanes 3, 8), 7.2 ng (lanes 4, 9), and 14.4 ng (lanes 5, 10).

Figures 7A, 7B, 7C:
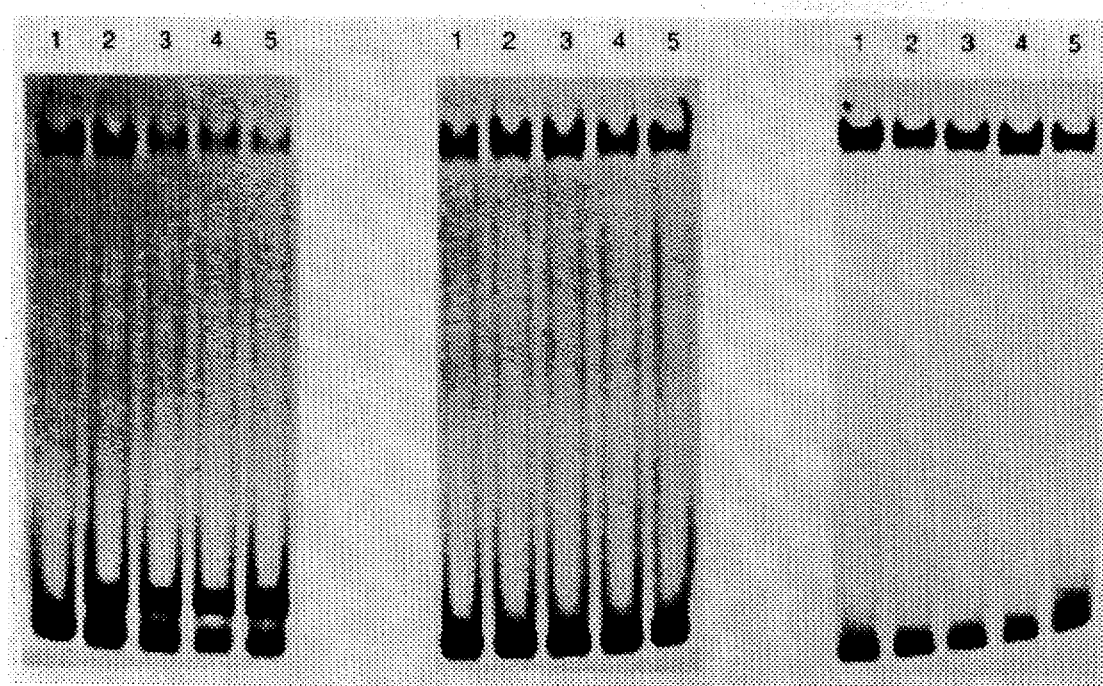

FIGS. 7A, 7B and 7C Tat competes with TRP-185 for binding to TAR RNA

TRP-185 and cofactor fractions were used in gel retardation assays with wild-type TAR RNA in the presence of increasing amounts of wild-type tat (A), mutant tat 52/57 (B), or glutathione-S-transferase (GST) (C). In each panel, the amount of added tat or tat 52/57 was 0 (lane 1), 50 ng (lane 2), 200 ng (lane 3), 1000 ng (lane 4) and 3000 ng (lane 5). The amount of GST used (C) was in 20-fold molar excess over corresponding lanes with tat (A) and tat 52/57(B).

FIG. 8

A wild-type HIV LTR CAT construct (lanes 1–4) or a similar construct containing a deletion of the TAR bulge region (+23/+25) (lanes 5–8) was restricted with Nco I. HeLa nuclear extract alone (lanes 1 and 5), with the addition of cofactor (lanes 2 and 6), sucrose gradient purified TRP-185 (lanes 3 and 7), or both cofactor and TRP-185 (lanes 4 and 8) were added to each reaction.

FIGS. 9A, 9B, 9C, 9D, and 9E

Column chromatography of the purification of TRP-185. (A) Superdex 200 FPLC, (B) Bio Rex 70, (C) Dextran Blue Sepharose, (D) Mono Q FPLC, (E) sucrose gradients. (B) to (E) column fractions were assayed with the presence of the cofactors fraction. (Activity assay gels are not shown for the first two columns, Heparin agarose and HTP Bio Gel.)

FIG. 10

Figure 11:
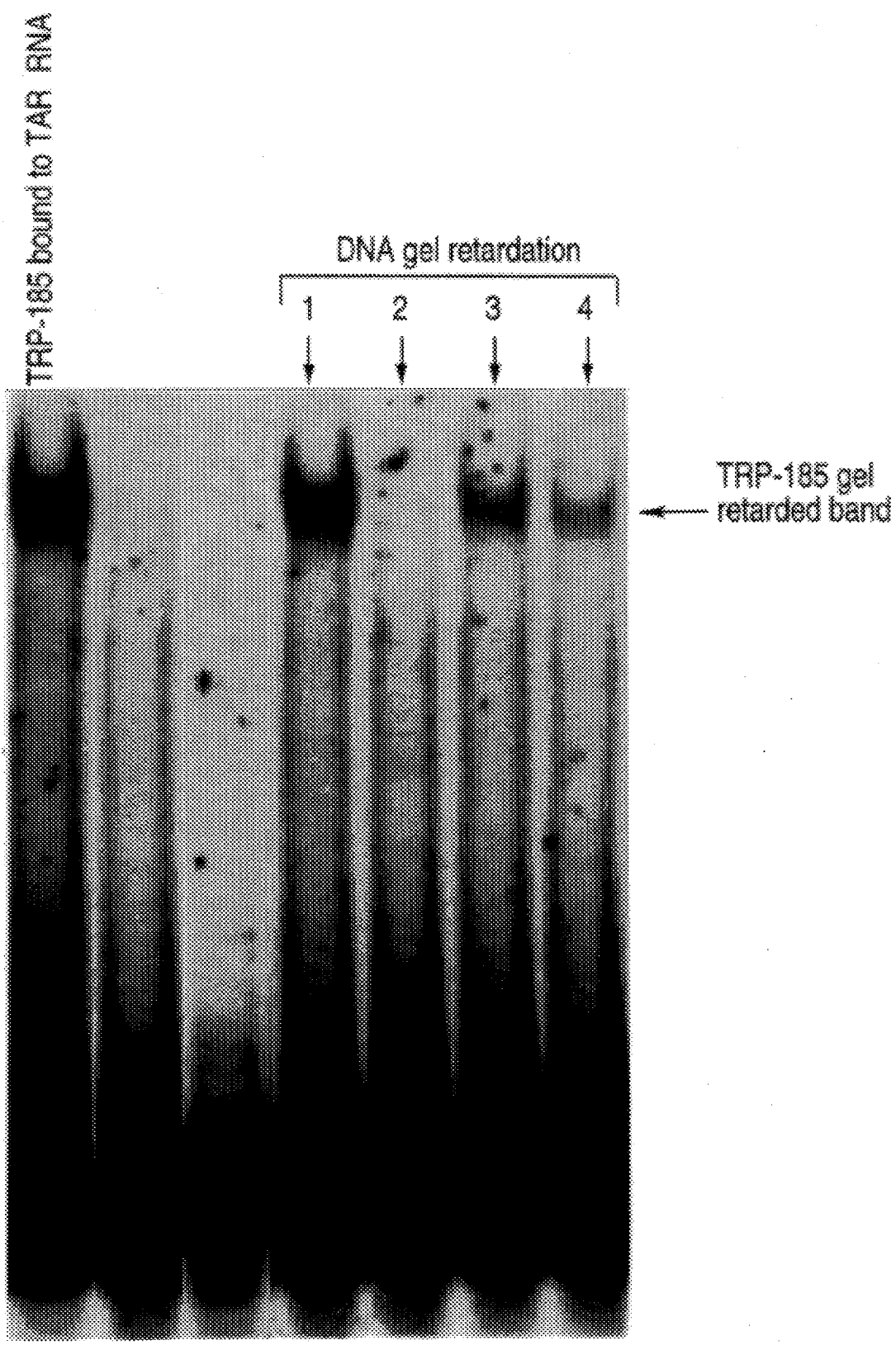
Figure 12:
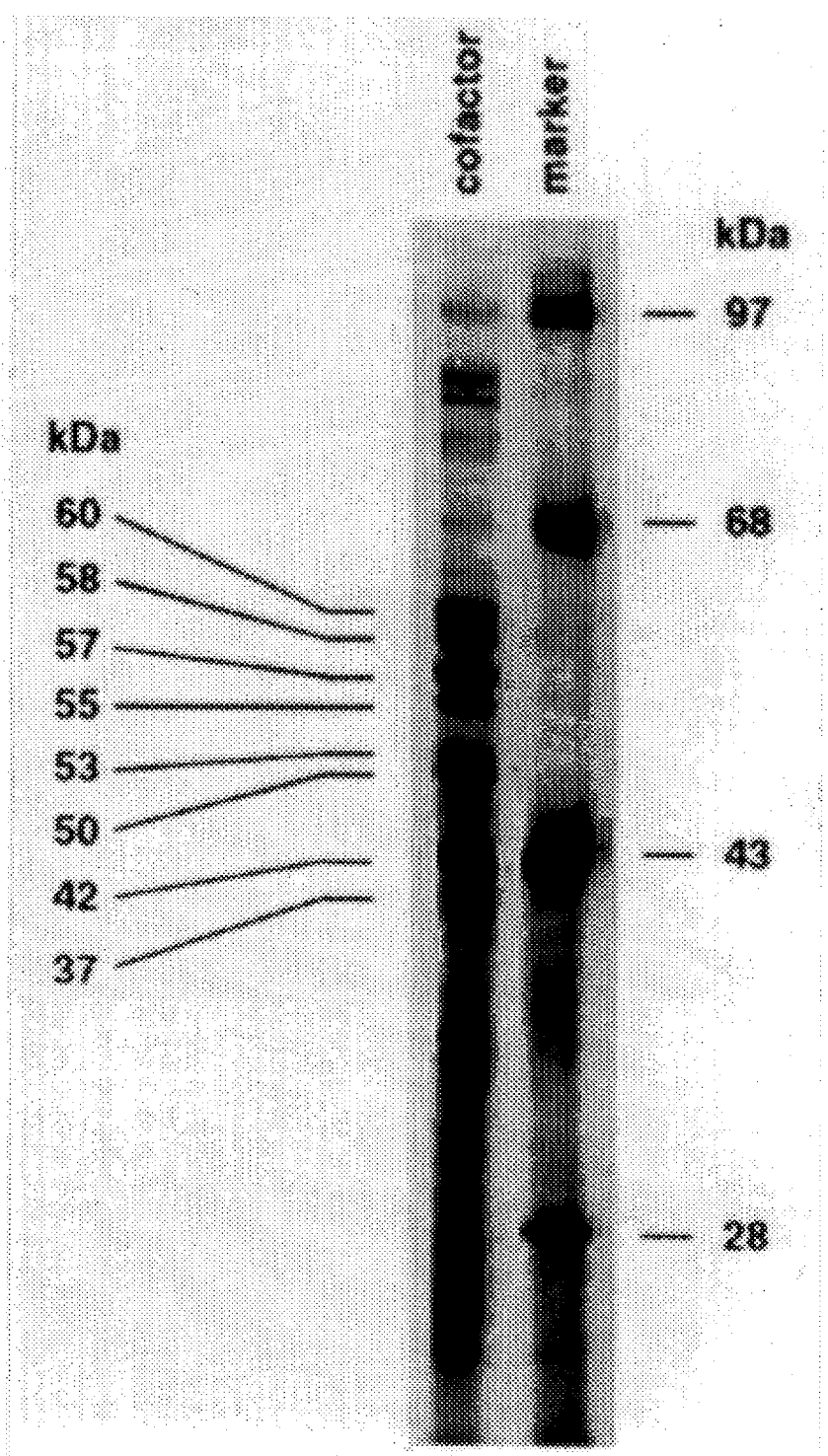

Silver stain gel of TRP-185 from sucrose gradient fractions. FIG. 11

Autoradiogram with DNA gel retardation analysis with HIV labeled DNA and competition analysis with cold HIV and adenovirus DNA. The darkest band (lane 1) represents HIV DNA without competition. The next lane (lane 2) represents cold DNA of HIV. Lane 3 represents a mutated HIV DNA. Lane 4 represents the adenovirus DNA.

FIG. 12

Silver stained gel of active co-factor fraction for TRP-185.

Figure 13:
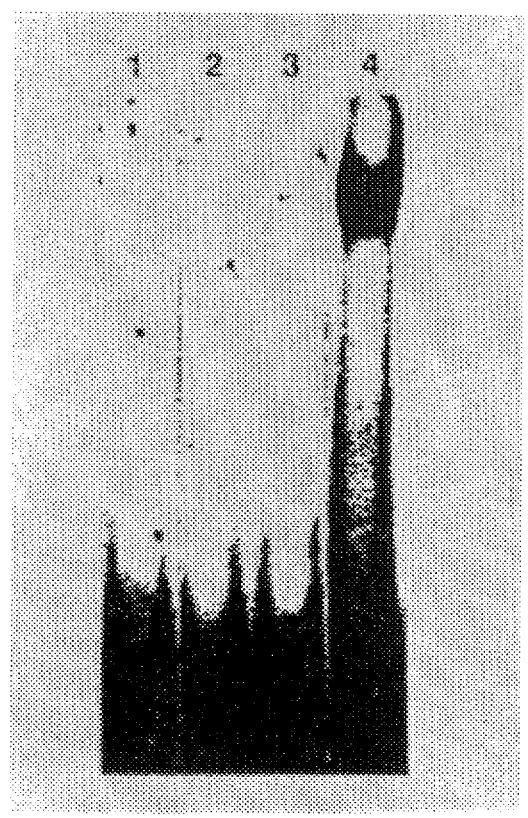

FIG. 13 Assay of TRP-185 co-factor fractions.

Highly purified fractions of TRP-185 were assayed by RNA gel retardation assay with TAR RNA in either the absence of presence of co-factor (lane 1), in the presence of the co-factor fraction which eluted from a biorex 70 column (lane 2), in the presence of the co-factor which bound to the Biorex 70 column (lane 3), or in the presence of both bound and eluted co-factor fractions (lane 4).

FIG. 14

Partial amino acid and nucleic acid sequence of degenerate oligonucleotides used to derive a PCR probe for TRP-185. The oligonucleotides: 1A, 1B, 4A and 4B; are identified by SEQ ID NOS:6–9, respectively.

FIG. 15

Northern Analysis of TRP-185. Total RNA from HeLa cells and Jurkat cells were analyzed for TRP-185 message binding.

DETAILED DESCRIPTION OF THE PREFERRED EMBODIMENTS

In its broadest embodiment, the invention provides a cellular protein with nucleic acid binding activity, particularly and most unusually to a viral RNA segment of HIV.

More specifically, the binding protein, designated herein as TRP-185 binds to HIV RNA at a region defined as the TAR region. This TRP-185 cellular protein binds viral RNA. The inventors have observed that the binding activity of the protein for viral RNA for example, may be enhanced in the presence of what is described herein as a "cofactor" fraction.

The cofactor fraction includes several peptides. One important peptide in the cofactor fraction is an ~100 kD cofactor. Because the cofactor(s) itself does not bind the RNA, it is believed that the capacity of TRP-185 to bind results from a post-translational modification (i.e., chemical modification) of the TRP-185 (present in the normal cellular environment) by other substances (such as in the "cofactor fraction"). This "modification" may facilitate the binding of TRP-185 to a particular nucleic acid segment binding site on DNA or RNA. For example, with HIV RNA, the substances present in the "cofactor fraction" may act to phosphorylate the TRP-185 protein, thereby facilitating attachment of the "phosphorylated" form of TRP-185 to the TAR region of the HIV RNA. Thus, the binding protein TRP-185 may be employed to regulate the level of gene transcription, and therefore the level of vital activity.

In addition, the present invention also encompasses inhibitors to this protein, (or to the cofactors which are shown to be important to the binding of TRP-185), which may be used to prevent the binding of the TRP-185 protein, to, for example, HIV RNA, and thereby also effect a "turning off" of the HIV virus. By way of example, such an "inhibitor" of TRP-185 could constitute an antibody specific for TRP-185, an antisense DNA, an RNA that preferentially binds the TRP-185 protein or other inhibitors of TRP-185 protein (TAR) binding activity.

The binding protein of the invention may also be regulating cellular genes. While the specific mechanism/function of the protein (TRP-185) in normal cellular gene function is not exactly known, the fact that the protein is cellular and is known to regulate other gene expression (i.e. binding to viral RNA and regulating vital genes) makes probable its role in regulation of cellular genes. The TRP-185 protein may be (in its nonactivated state) bound to an RNA but be able to move and attach to a variety of DNAs or RNAs. The TRP-185 protein may thus constitute a critical factor in cellular growth control. Thus, the TRP-185 binding element of the present invention may constitute a reagent useful in the study of nucleic acid binding activity and gene expression, such as HIV regulation and expression, and for identifying potential substances that inhibit this activation events, thereby regulating TAR region activation.

Nucleic Acid Hybridization

The DNA sequences disclosed herein will also find utility as probes or primers in nucleic acid hybridization embodiments. As such, it is contemplated that oligonucleotide fragments corresponding to the sequence of SEQ ID NO:1 for stretches of between about 10 nucleotides to about 20 or to about 30 nucleotides will find particular utility, with even longer sequences, e.g., 40, 50, 100, even up to full length, being more preferred for certain embodiments. The ability of such nucleic acid probes to specifically hybridize to TRP-185-encoding sequences will enable them to be of use in a variety of embodiments. For example, the probes can be used in a variety of assays for detecting the presence of complementary sequences in a given sample. However, other uses are envisioned, including the use of the sequence information for the preparation of mutant species primers, or primers for use in preparing other genetic constructions.

Nucleic acid molecules having stretches of 10, 20, 30, 50, or even of 100 nucleotides or so, complementary to SEQ ID NO:1 will have utility as hybridization probes. These probes will be useful in a variety of hybridization embodiments, such as Southern and Northern blotting in connection with analyzing the role of TRP-185 in HIV activation. The total size of fragment, as well as the size of the complementary stretch(es), will ultimately depend on the intended use or application of the particular nucleic acid segment. Smaller fragments will generally find use in hybridization embodiments, wherein the length of the complementary region may be varied, such as between about 10 and about 100 nucleotides, or even up to the full length of the cDNA as shown in SEQ ID NO:1 according to the complementary sequences one wishes to detect.

The use of a hybridization probe of about 10 nucleotides in length allows the formation of a duplex molecule that is both stable and selective. Molecules having complementary sequences over stretches greater than 10 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 nucleotides, or even longer where desired. Such fragments may be readily prepared by, for example, directly synthesizing the fragment by chemical means, by application of nucleic acid reproduction technology, such as the PCR technology of U.S. Pat. No. 4,603,102 (herein incorporated by reference) or by introducing selected sequences into recombinant vectors for recombinant production.

Accordingly, the nucleotide sequences of the invention may be used for their ability to selectively form duplex molecules with complementary stretches of TRP-185 genes or cDNAs. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and or high temperature conditions, such as provided by 0.02M–0.15M NaCl at temperatures of 50° C. to 70° C. Such selective conditions tolerate little, if any, mismatch between the probe and the template or target strand, and would be particularly suitable for isolating TRP-185, and TRP-185-like genes.

Of course, for some applications, for example, where one desires to prepare mutants employing a mutant primer strand hybridized to an underlying template or where one seeks to isolate TRP-185-encoding sequences from related species, functional equivalents, or the like, less stringent hybridization conditions will typically be needed in order to allow formation of the heteroduplex. In these circumstances, one may desire to employ conditions such as 0.15M–0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, colorimetric indicator substrates are known which can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

Longer DNA segments will often find particular utility in the recombinant production of peptides or proteins. DNA segments which encode peptide antigens from about 15 to about 50 amino acids in length, or more preferably, from about 15 to about 30 amino acids in length are contemplated to be particularly useful, as are DNA segments encoding the entire TRP-185 protein. DNA segments encoding peptides will generally have a minimum coding length in the order of about 45 to about 150, or to about 90 nucleotides. DNA segments encoding full length proteins may have a minimum coding length in the order of about 4863 nucleotides for a protein in accordance with SEQ ID NO:2.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is contemplated that a nucleic acid fragment of almost any length may be employed, with the total length preferably being limited by the ease of preparation and use in the intended recombinant DNA protocol. For example, nucleic acid fragments may be prepared in accordance with the present invention which are up to 10,000 base pairs in length, with segments of 5,000 or 3,000 being preferred and segments of about 1,000 base pairs in length being particularly preferred.

It will be understood that this invention is not limited to the particular nucleic acid and amino acid sequences of SEQ ID NO:1 and SEQ ID NO:2, respectively. Therefore, DNA segments prepared in accordance with the present invention may also encode biologically functional equivalent proteins or peptides which have variant amino acids sequences. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged.

DNA segments encoding a TRP-185 gene may be introduced into recombinant host cells and employed for expressing a TRP-185 structural or related protein. Alternatively, through the application of genetic engineering techniques, subportions or derivatives of the TRP-185 gene may be employed. Equally, through the application of site-directed mutagenesis techniques, one may re-engineer DNA segments of the present invention to alter the coding sequence, e.g., to introduce improvements to the antigenicity of the protein or to test TRP-185 mutants in order to examine TAR binding activity at the molecular level. Where desired, one may also prepare fusion peptides, e.g., where the TRP-185 coding regions are aligned within the same expression unit with other proteins or peptides having desired functions, such as for immunodetection purposes (e.g., enzyme label coding regions).

Pharmaceutical Preparations

Aqueous compositions (inocula) identified as candidate substance during the screen provided by the present invention may comprise an effective amount of the decorin family agent dissolved or dispersed in a pharmaceutically acceptable aqueous medium. Such compositions are also referred to as inocula. The phrase "pharmaceutically acceptable", as used herein, refers to molecular entities and compositions that do not produce an allergic or similar untoward reaction when administered to a human.

The preparation of an aqueous composition that contains a protein or proteoglycan as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

A proteoglycan can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and the scope of the invention be embraced by the defined claims.

The following examples are presented to describe preferred embodiments and utilities and to satisfy "best mode" requirements of the present invention, but should not be construed as limiting the claims thereof. The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

ISOLATION AND PURIFICATION OF NUCLEIC ACID BINDING PROTEIN TRP-185

The present example is provided to demonstrate the most preferred method for isolating a bioactive TRP-185 protein from a mammalian nuclear cell extract. However, it is contemplated that upon further sequence analysis of the protein and subsequent cloning and expression of the gene, the TRP-185 binding protein may also be obtained in an even more pure preparation from an expression system (outlined in Example 9 and 12). The purification scheme is shown in a flow diagram in Table 2 and is described in detail in this example.

Preparation of Mammalian Nuclear Cell Extract

Virtually any mammalian cell type may be used to prepare the initial nuclear cell extract. By way of example, cell lines which may be used include VERO, Jurkat, CEM, W138, BHK, COS, 293, MDCK, and HeLa cells. Most preferably, the HeLa cell line is the cell line of choice for preparation of the nuclear cell extract.

About 60 liters of HeLa cells were obtained and nuclear extract prepared therefrom. The procedure used was basically that described by Digham et al. (1983).[35]

Buffers—Buffers used for extract preparation are designated as follows: Buffer W contains 10 mM HEPES (pH 7.9 at 4° C.), 1.5 mM $MgCl_2$, 10 mM KCl and 0.5 mM DTT; Buffer X contains 0.3M HEPES (pH 7.9), 1.4M KCl and 0.03M $MgCl_2$; Buffer Y contains 20 mM HEPES (pH 7.9), 25% (v/v) glycerol, 0.42M NaCl, 1.5 mM $MgCl_2$, 0.2 mM EDTA, 0.5 mM phenylmethylsulfonyl fluoride (PMSF) and 0.5 mM DTT; buffer Z contains 20 mM HEPES (pH 7.9), 20% (v/v) glycerol, 0.1M KCl, 0.2 mM EDTA, 0.5 mM PMSF, and 0.5 mM DTT. DTT and PMSF were added fresh to the buffers just before use.

Cells—HeLa cells (obtainable from C. Attardi, California Institute of Technology) were grown in spinner flasks at 37° in Joklik's MEM (minimal essential media) containing 5% calf serum. HeLa cells were grown to 4 to $6 \times 10^5$ cells per ml prior to harvesting for extract preparation.

Standard Procedure for Extract Preparation—HeLa cells were harvested from cell culture media by centrifugation (at room temperature) for 10 min at 2000 rpm in a Sorvall HG4L rotor. Palette cells were then suspended in five volumes of 4° C. phosphate buffered saline and collected by centrifugation as detailed above; subsequent steps were performed at 4° C. The cells were suspended in five packed cell pellet volumes of buffer W and allowed to stand for 10 min. The cells were collected by centrifugation as before and suspended in two packed cell pellet volumes (volume prior to the initial wash with buffer W) of buffer W and lysed by 10 strokes of a Kontes all glass Dounce homogenizer (B type pestle). The homogenate was checked microscopically for cell lysis and centrifuged for 10 min at 2000 rpm in a Sorvall HG4L rotor pellet nuclei. The supernatant was carefully decanted, mixed with 0.11 volumes of buffer X, and centrifuged for 60 min at 100,000 $g_{av}$ (Beckman Type 42 rotor). The high speed supernatant from this step was dialyzed five to eight hours against 20 volumes of buffer Z and is designated the S-100 fraction.

The nuclear extract was prepared as follows. The pellet obtained from the low speed centrifugation of the homogenate was subjected to a second centrifugation for 20 min at 25,000 $g_{av}$ (Sorvall SS34 rotor), to remove residual cytoplasmic material and this pellet was designated as crude nuclei. These crude nuclei were resuspended in 3 ml of buffer Y per $10^9$ cells with a Kontes all glass Dounce homogenizer (10 strokes with a type B pestle). The resulting suspension was stirred gently with a magnetic stirring bar for 30 min and then centrifuged for 30 min at 25,000 $g_{av}$ (Sorvall SS34 rotor). The resulting clear supernatant was dialyzed against 50 volumes of buffer Z for five hours. The dialysate was centrifuged at 25,000 $g_{av}$ (Sorvall SS34 rotor) for 20 min and the resulting precipitate discarded. The supernatant, designated the nuclear extract, was frozen as aliquots in liquid nitrogen and stored at −80°. The protein concentration was usually 6 to 8 mg per ml and 15 to 20 mg of protein were obtained from $10^9$ cells.

Purification of HIV TAR RNA binding protein (TRP-185)

Nuclear extracts were prepared as described above.[35] All procedures were performed at 4° C. Nuclear extract prepared from 60 liters of Hela cells was applied to a heparin-agarose column (2.5×9 cm) and equilibrated with buffer A (20 mM Tris, pH 7.9, 20% glycerol (v/v), 0.2 mM EDTA) containing 0.1M KCl, 0.5 mM DTT and 0.5 mM PMSF. The column was washed with the same buffer until the A280 was almost zero, and then bound proteins were eluted with buffer A with 0.4M KCl, 0.5 mM PMSF and 0.5 mM DTT. The 0.4M KCl buffer a fractions were pooled and dialyzed vs. buffer A with 0.1M KCl, 0.5 mM PMSF and 0.5 mM DTT. The dialyzed fraction was then applied to HTP Bio Gel, which is an anionic separation gel (2.5×5 cm) equilibrated with the same buffer. The column was washed and eluted with buffer A containing 0.1M potassium phosphate. The active fractions were pooled and precipitated with 70% ammonium sulfate and then applied to a molecular weight separation column, specifically a Superdex 200 FPLC column equilibrated with buffer A containing 0.1M KCL and 1 mM DTT. The active fractions were pooled and applied to another molecular weight separation column, in this case a Bio Rex 70 (1.5×3 cm) column in the same buffer. The active flow-through fractions were pooled and applied to an anionic separation column, Dextran Blue Sepharose (1.5×2 cm) equilibrated in the same buffer. The column was washed and eluted with buffer A containing 0.4M KCL and 1 mM DTT. The active fractions were pooled and dialyzed rs. Buffer A with 0.1M KCL and 1 mM DTT. The pooled and dialyzed fraction was then applied to Mono Q FPLC, an anionic separation column, and 1 ml column equilibrated in the same buffer. The column was washed and eluted with buffer A with 0.4M KCL. The active fractions were dialyzed rs. 20 mM Tris, pH 7.9, 5% glycerol and 0.2 mM EDTA, 0.1M KCL and 1 mM DTT. These fractions were then loaded onto tubes (1.4×8.9 cm) containing 10 ml of a 5% to 20% continuous sucrose gradient. A preparative sucrose gradient was then performed using Beckman SW 41 Ti rotor at 28,000 rpm for 40 hours at 4° C. The sucrose gradients were fractionated from the bottom of each tube, assayed, and stored at 4° C. At this stage the degree of purification of the TRP-185 protein was approximately 3000-fold. The dissociation constant $K_d$ was determined, and Scatchard analysis for TRP-185 was obtained as described.[41]

A protocol which included less steps in the purification of the nuclear extract and column chromatography over Sephacryl S-300 resulted in poor yield and a less pure preparation of the nucleic acid binding protein. Using that protocol, the partial purification of TRP-185 binding protein obtained was about a 72-fold purified preparation, (see Table 3, final specific activity of 252 ng/mg/+initial activity of 3.5 ng/mg).

The mammalian cell nuclear extract processing protocol outlined in Table 2 is therefor submitted for "best mode" purposes (providing a 1,000–10,000 fold purified TRP-185 protein preparation). However, the TRP-185 nucleic acid binding protein preparations should be equally effacious in, for example, stimulation of HIV gene expression, in analysis by gel retardation and UV cross-linking for binding to TAR RNA, and in the interaction of TRP-185 with TAR RNA in the presence or absence of a "cofactor" fraction. The differences observed between the two preparations, therefore, would only relate to the potency of the TRP-185 preparation.

Prepared according to the above described method, the cellular binding protein TRP-185 may remain stable for between 3–6 months stored at between 0°–4° C.

TABLE 2

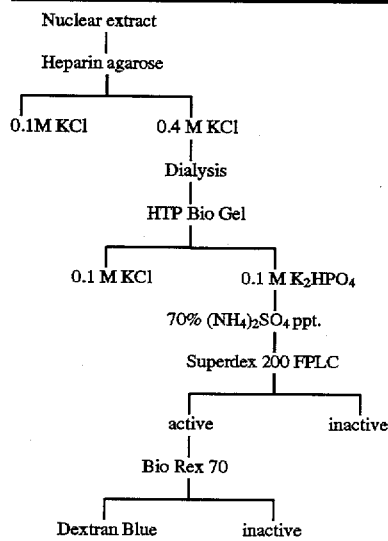

TABLE 2-continued

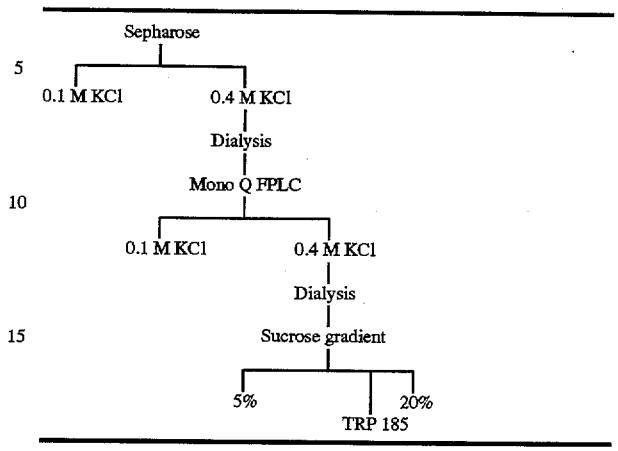

TABLE 3

Partial Purification of TRP-185

| Procedure | Volume (ml) | Total Protein (mg) | Total binding activity (ng) | Sp. act* (ng/mg) | Yield (%) |
|---|---|---|---|---|---|
| HeLa Cells (60 g) | 60 | 3000 | | | |
| Nuclear extract | 60 | 590 | | | |
| Heparin-agarose | 66 | 300 | 1050 | 3.5 | 100 |
| Ammonium Sulfate (ppt.) | 4.9 | 252 | 932 | 3.7 | 89 |
| Sephacryl S-300 | 40 | 33 | 370 | 11.2 | 35 |
| FPLC Mono S | 35 | 14 | 342 | 24.4 | 33 |
| HTP Bio gel | 5.6 | 3.6 | 168 | 46.8 | 16 |
| Sucrose gradient | 10 | 0.61 | 154 | 252 | 15 |

Maximal binding conditions at each step were determined and then binding was performed at optimal conditions. Appropriate bands were cut out and counted by liquid scintillation.
*Specific activity is defined as the ng of labelled (+1/+80) HIV wt RNA bound per mg of protein in the binding reaction.

While an about 72% fold purified preparation of TRP-185 cellular protein from a HeLa cell extract was obtained using the procedure outlined in Table 3, the modified protocol described herein, which most notably excludes the Sephacryl S-300 column, provided a preparation of about 3,000-fold purity from the HeLa cell nuclear extract.

Gel Retardation Assay for TRP and Tat Binding

The probe for binding assay was prepared by in vitro transcription of a plasmid directing the synthesis of nucleotides 1 to +80 from the ARV-2 HIV LTR using T7 polymerase and alpha$^{32}$P-GTP (3000 Ci/mmol). The transcribed RNA was gel-isolated, eluted and used for binding. Approximately 1.5 ng of TAR RNA probe was mixed with extract (0.6 μg–10 μg), poly (I)-poly (C)(0.5 μg–4 μg), and final concentration of 10 mM Tris (pH 7.4), 0.1 mM EDTA, 50 mM KCL, 1 mM 2-mercaptoethanol and 10% glycerol in 50μl total volume. Protein samples from the heparin-agarose column (10 μg), S 300 column (4 μg), Mono S column (3.9 μg), HTP Bio gel column (2.6 μg) and sucrose gradient pool (0.6 μg) were used. The binding was performed at room temperature for 30 minutes and then the samples were loaded onto a 4% polyacrylamide gel containing 1×TBE and 2% glycerol, and electrophoresed at 180 V in 1×TBE and 2% glycerol at room temperature. The gel was dried and exposed overnight with an intensity screen at 70° C. For sucrose gradient fractions, 10μl of the cofactor fraction was added to restore activity. For competition analysis, 0–50 ng of each of the unlabeled in vitro transcribed competitor RNAs was mixed with probe and then binding was performed. Binding assays to labeled TAR RNA probes (1.5 ng) were performed in a 50 μl total volume as described (Roy et al., 1990b). Competition studies with TRP-185 (0.6 μg), cofactor fraction (10 μl) and tat protein (0 to 60 ng) were performed under the same conditions.

UV Crosslinking of TRP-185 to TAR RNA

Figures 1A, 1B, 1C:
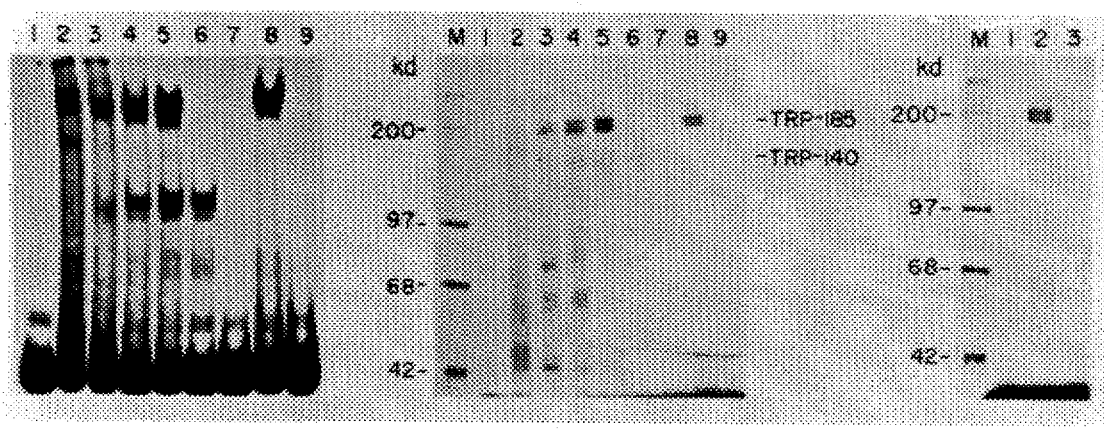
FIGS. 1A, 1B and 1C Assay of TRP-185 and TRP-140 fractionation.

UV crosslinking of TRP-185 TAR RNA was performed under similar binding conditions. Briefly, the binding reaction of TRP-185 was first done as described above. After 30 minutes at room temperature, the reactions were irradiated under Fotodyne U.V. lamp (maximum emission wavelength 7000 uW/cm2) at a distance of 4.5 cm from the UV source for 30 minutes. 50 U of RNase T1 was added, incubated at room temperature for 10 minutes, loading dye added, heated for 5 minutes at 95° C., and the samples electrophoresed on 8% SDS-polyacrylamide gel. Gels were dried and subject to autoradiography TRP-185 and TRP-140 bind to TAR RNA The purification table for HeLa cell nuclear extracts containing proteins that bound to TAR RNA is indicated in Table 3. Gel retardation analysis was performed to assay different column fractions for their ability to bind TAR RNA. As shown in FIG. 1A, lane 2, one major gel-retarded species was detected following fractionation on heparin agarose. Gel-retardation analysis with unfractionated nuclear extract yielded a number of additional retarded species, but competition analysis indicated that they bound to a variety of nonspecific RNA templates (data not shown). Further chromatography on Sephacryl S-300, Mono S fast protein liquid chromatography (FPLC), and hydroxyapatite columns revealed two major gel-retarded species (FIG. 1A lanes 3–5). These two species could be separated following preparative sucrose gradient centrifugation (FIG. 1A, lanes 6–8).

UV cross-linking in the absence of RNase with each of the column fractions shown in FIG. 1A was also performed (FIG. 1B). The results were consistent with the slower-mobility gel-retarded species migrating on SDS-polyacrylamide gels at 200 kD and the faster-mobility gel-retarded species migrating at 155 kD (FIG. 1B). Treatment of each of these species with RNase T1 following UV cross-linking revealed a decrease in their molecular masses to 185 kD (TRP-185)(FIG. 1C) and 140 kD (TRP-140)(data not shown), respectively. UV cross-linking, gel electrophoresis, and autoradiography of the gel slice containing these gel-retarded species also revealed the presence of either the 185-kD or the 140-kD species (data not shown). It was noted that in the absence of RNase T1, UV cross-linking of wild-type TAR RNA and TRP-185 resulted in two species, whereas in the presence of Ease, only one species was detected (FIG. 1C). It is thus possible that TRP-185 was capable of binding more than one TAR RNA molecule.

Figure 10:
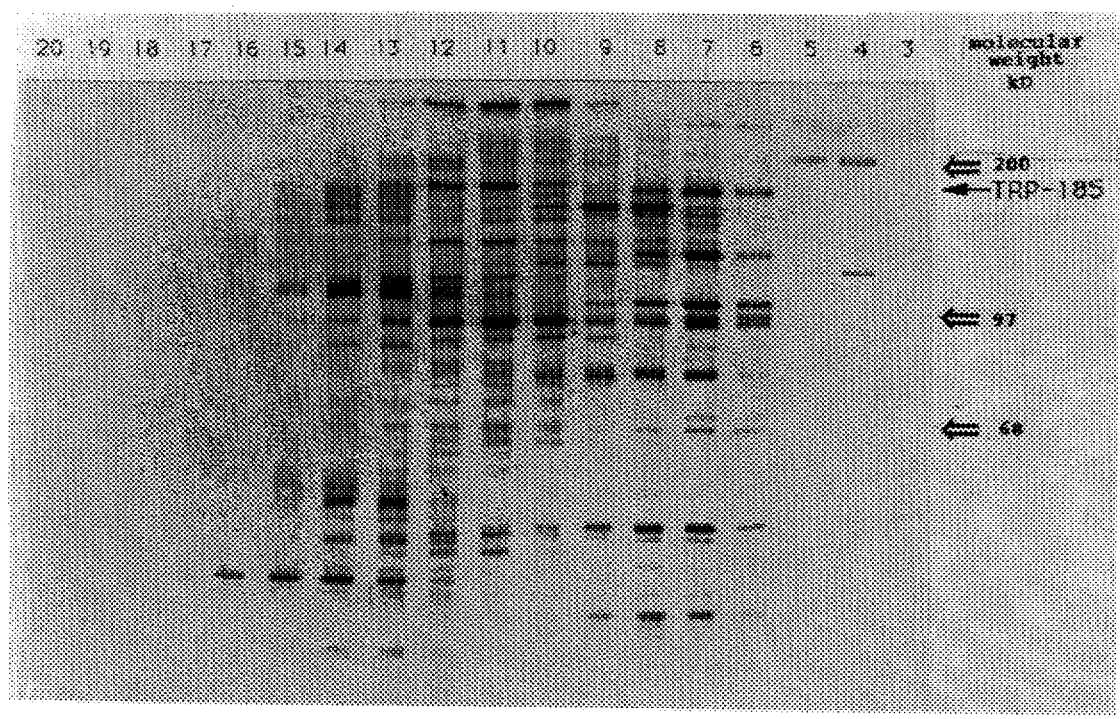

FIG. 9 shows autoradiograms of the last five purification steps in the improved isolation of TRP-185 (Table 2) and FIG. 10 demonstrates a silver stained gel of the TRP-185 sucrose gradient fractions. Fractions 6, 7 and 8 in FIG. 9E correspond to lanes 6, 7 and 8 of the silver stained gel in FIG. 10.

EXAMPLE 2

PREPARATION AND CHARACTERIZATION OF A COFACTOR FRACTION

The present example is provided to teach the method by which the cofactor faction used in the present invention was prepared. The cofactor fraction has been characterized to include several individual cofactors, including cofactors of about 100 kD, 64 kD, and 46 kD cofactor. The addition of a volume of the entire cofactor fraction must be present to observe binding of TRP-185 to TAR RNA in vitro. Isolated individual cofactors have not been observed to bind to the TAR region of HIV RNA.

PREPARATION OF COFACTOR FRACTION

Cofactor proteins modulate TRP-185 binding to TAR RNA

Figure 2A:
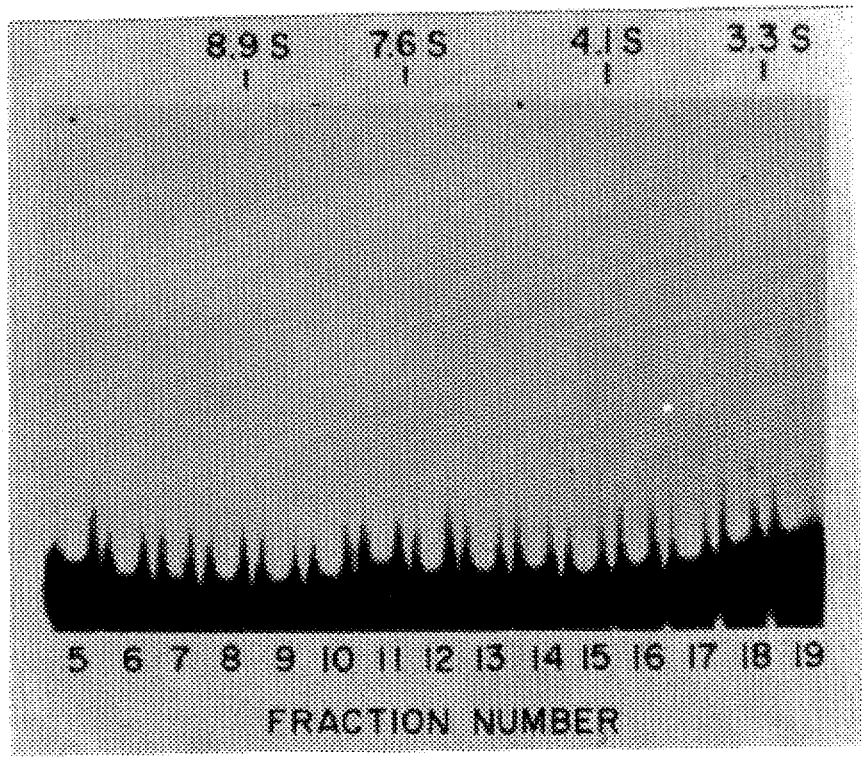
FIGS. 2A and 2B Analytical sucrose gradient analysis of TRP-185.
Figure 2B:
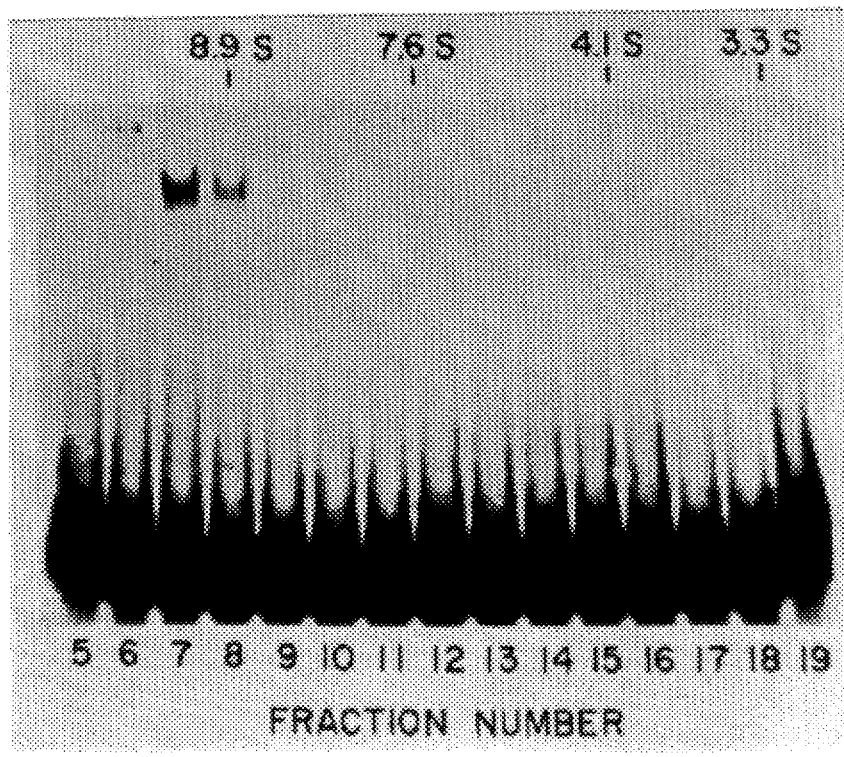

To determine the binding properties and the native size of TRP-185, preparative sucrose gradient fractions containing TRP-185 were further characterized by analytical sucrose gradient centrifugation (FIG. 2). Molecular weight markers were included in parallel gradients to determine the position of TRP-185 in the gradient. None of the fractions from the analytical sucrose gradient including fractions that contained proteins migrating between 180–200 kDa gave rise to gel-retarded species (FIG. 2A). Prolonged exposures of this autoradiogram did not result in detectable gel-retarded species (data not shown). This suggested that TRP-185 may require several components for binding to TAR RNA as previously suggested (FIG. 1A, lines 7–9). Individual fractions from the original preparative sucrose gradient (see Example 1) were added to fractions from the analytical sucrose gradient. The combined fractions were then analyzed by gel retardation analysis (FIG. 2B). Fractions from the analytical sucrose gradient which comigrated at 9.5S (near the 200 kDa molecular weight marker) were active in gel-retardation only when combined with an additional fraction which sedimented at about 100 kDa in the preparative sucrose gradient (FIG. 2B). This 100 kDa cofactor (CF) fraction did not result in UV crosslinked or gel retarded species either alone (FIG. 1A and 1B, lane 9) or when combined with other sucrose gradient fractions. Heat lability, trypsin sensitivity, and further fractionation were consistent with the fact that this cofactor fraction contained proteins. These results were consistent with a model in which the binding activity of TRP-185 is modulated by cofactors which were themselves not capable of binding TAR RNA directly.

It is possible that these cofactors may be a class of cellular kinases which alter the phosphorylation of TRP-185, with resultant changes in its binding affinity. The observation that protein kinase C expression vectors activate tat-mediated expression via the TAR element is consistent with this possibility.[36] However, it cannot definitively be ruled out that TRP-185 may weakly interact with these cofactor species. Similar interactions occur with the multisubunit factor, CstF, which is required for mRNA polyadenylation.[39] A 64 kDa species is seen upon UV crosslinking of CstF to RNA, but other components of the complex must be present to reconstitute the binding of this species. Both UV crosslinking and sucrose gradient analysis indicate the TRP has a molecular weight of approximately 185 kDa which makes the presence of a multi-component complex unlikely.

EXAMPLE 3

PREPARATION OF ANTIBODIES TO TRP-185 ANTIGEN

Monoclonal and polyclonal antibodies raised against TRP-185 exposed and unexposed to cofactor fraction are obtained as described in this example. These antibodies are useful for (1) screening a cDNA expression library in the process of cloning the gene that encodes TRP-185 (for example, the SUPERSCREEN® immunoscreening system from AMERSHAM®ss), (2) facilitating the purification of TRP-185 by using column chromatography to which the monoclonal antibody is bound, and (3) providing reagents necessary for a diagnostic immunoassay for screening biological samples.

Monoclonal antibodies are obtained using the following procedure:[51]

Immunization Schedule for Raising Monoclonal Antibodies

1. For each mouse, mix 250μl of antigen solution containing 10 μg of TRP-185 with 250μl of complete Freund's adjuvant. Inject six BALB/c female mice ip (intraperitoneal injection).
2. After 14 days, repeat the injections of TRP-185 and incomplete Freund's adjuvant.
3. Collect tail bleeds from immunized mice on day 24. Do 1 in 5 dilutions in phosphate buffered saline (PBS) and test all samples by comparison with similar dilutions of normal mouse serum in a dot blot.
4. On day 35, inject all animals ip with TRP-185 and incomplete Freund's.
5. Day 45, do tail bleeds and test by dot blot. All serum samples checked by immunoprecipitation against in vivo radiolabeled antigen preparation.
6. Day 56, inject best responder, 100 μl iv and 100 μl ip. All others get ip injection with incomplete Freund's.
7. Day 59, fuse splenocytes from best responder.

The resultant hybridoma tissue culture supernatants are screened for monoclonal antibodies as follows:

1. A protein solution of at least 1 μg/ml of TRP-185 is added to a nitrocellulose sheet at 0.1 ml/cm². Allow the protein to bind to the paper for 1 hr. Higher concentrations of proteins will increase the signal and make screening faster and easier. If the amount of protein is not limiting, concentrations of 10–50 μg/ml should be used. Nitrocellulose can bind approximately 100 μg of protein per cm².
2. Wash the nitrocellulose sheet three times in PBS.
3. Place the sheet in a solution of 3% BSA in PBS with 0.02% sodium azide for 2 hr to overnight. To store the sheet, wash twice in PBS and place at 4° C. with 0.02% sodium azide. For long-term storage, shake off excessive moisture from the sheet, cover in plastic wrap, and store at −70° C.
4. Place the wet sheet on a piece of parafilm, and rule with a soft lead pencil in 3-mm squares. Cut off enough paper for the number of assays.
5. Apply 1μl of the hybridoma tissue culture supernatant to each square. Incubate the nitrocellulose sheet on the parafilm at room temperature in a humid atmosphere for 30 min.

Along with dilutions of normal mouse serum, include dilutions of the mouse serum from the last test bleed as controls. Dilutions of the test sera are essential to control correctly for the strength of the positive signals. Mouse sera will often contain numerous antibodies to different regions of the antigen and therefore will give a stronger signal than a monoclonal antibody. Therefore, dilutions need to be used to lower the signal. Good monoclonal antibodies will appear 10-fold less potent than good polyclonal sera.

6. Quickly wash the sheet three times with PBS, then wash two times for 5 min each with PBS.
7. Add 50,000 cpm of $^{125}$I-labeled rabbit anti-mouse immunoglobulin per 3-mm square in 3% BSA/PBS with 0.02% sodium azide (about 2.0 ml/cm²).
8. After 30–60 min of incubation with shaking at room temperature, wash extensively with PBS until counts in the wash buffer approach background levels.
9. Cover in plastic wrap and expose to X-ray film with a screen at −70° C.

The hybridoma identified as producing antibody to TRP-185 exposed and unexposed to cofactor fraction is passaged as follows:

1. Inject 10⁷ (or less) cells into female mice that have been injected ip about 1 week earlier with 0.5 ml of pristane or incomplete Freund's adjuvant. These types of injections are also used to prime mice for ascites production, and this may serve as a convenient source of appropriate hosts. If no mice are available, inject mice with incomplete Freund's adjuvant and wait 4 hr to 1 day before injecting the hybridoma cells. The animals must be of the same genetic background as your cell line.
2. If an ascites develops, tap the fluid and transfer into a sterile centrifuge tube.
3. Spin the ascites at 400 g for 5 min at room temperature.
4. Remove the supernatant. Resuspend the cell pellet in 10 ml of medium supplemented with 10% fetal bovine serum and transfer to a tissue culture plate. The supernatant can be checked for the presence of the antibody and used for further work if needed.
5. Handle as for normal hybridomas, except keep the cells separate from the other cultures until there is little chance of the contamination reappearing.

EXAMPLE 4

SPECIFICITY OF TRP-185 BINDING FOR HIV TAR RNA

To determine whether TRP-140 and TRP-185 bound specifically to TAR RNA, RNA gel retardation and competition analysis were performed.

Plasmid Constructs and Labeling of mRNAs

Wild-type and mutant HIV mRNAs were constructed by fusing a synthetic linker containing a T7 RNA polymerase promoter to DNA fragments of the indicated TAR constructs from +1 to +80[10]. Transcription of these constructs was linearized with Hind III (+80) using T7 RNA polymerase resulting in transcripts consisting of nucleotides +1 to +80 of the HIV LTR. RNA synthesis, labeling, and purification were performed using the reagents and procedures of the Riboprobe System II (Promega).[32]

TRP-185 binding requires both the TAR RNA loop sequences and secondary structure Each of the TAR RNA species illustrated in FIG. 3A–FIG. 3J was placed downstream of the T7 promoter and transcribed in vitro in either the presence or absence of labeled nucleotides. These constructs include wild-type, a substitution of the loop sequences (+31/+34), a mutation of the TAR primary sequence (TAR-sense), a disruption of the stem structure (+19/+22), restoration of the stem structure/(+19/+22)/(+40/+43)/, a point mutation in the bulge region (+23), a deletion of the bulge region ▲(+23/+25), and mutations in the loop sequences at positions (+30), (+32), and (+34). Gel retardation with labeled wild-type TAR RNA and competition with unlabeled RNAs were performed with both TRP-140 and TRP-185 eluted from the hydroxylapatite column, and with TRP-185 plus a cofactor fraction obtained from sucrose gradient centrifugation FIGS. 4A–4C and FIG. 5A–5C. Table 4 reveals the relative activity of each of these constructs in the context of the HIV LTR when transfected into HeLa cells in the presence of a tat expression vector. Thus, the present inventors could correlate in vitro binding assays with the in vivo activity of these templates.

TABLE 4

Relative activity of TAR mutant constructs with tat

| Construct | Relative CAT activity |
|---|---|
| 1. wild-type | 1.0 |
| 2. (+31/+34) | 0.04 |
| 3. TAR sense | 0.41 |
| 4. (+19/+22) | 0.08 |
| 5. (+19/+22)/(+40/+43) | 0.96 |
| 6. (+23) | 0.22 |
| 7. Δ(+23/+25) | 0.25 |
| 8. (+30) | 0.16 |
| 9. (+32) | 0.18 |
| 10. (+34) | 0.22 |

Transfections of each of these constructs in the context of the HIV LTR (−170/+80) fused to CAT in the presence of a tat expression vector were performed and the percent CAT conversion determined.[43] The results were normalized to the percent CAT conversion of the wild-type construct and reflect the average of three independent determinations.

Gel retardation with the hydroxylapatite column fraction revealed two species corresponding to TRP-140 and TRP-185 (FIG. 4A, lane 2). TRP-185 was competed by a 30-fold excess of unlabeled wild-type TAR RNA while TRP-140 was not competed using a similar amount of competitor (FIG. 4A, lane 3). Larger quantities of wild-type competitor resulted in the loss of TRP-140 binding, but all other TAR RNAs tested also competed at similar concentrations, indicating minimal binding specificity for TRP-140 (data not shown). TAR RNA species containing substitutions of the loop sequences (+31/+34) resulted in only minor levels of competition of TRP-185, indicating a critical role for the loop sequences in TRP-185 binding (FIG. 4A, lane 4). Mutation of the TAR PaA primary sequence (TAR-sense) resulted in levels of competition of TRP-185 similar to that found with wild-type TAR RNA (FIG. 4A, lane 5). A disruption of the TAR stem structure (+19/+22) resulted in decreased competition of TRP-185 binding (FIG. 4A, lane 6), while restoration of the stem structure (+19/+22)/(+40/+43) resulted in near wild-type levels of competition (FIG. 4A, lane 7). A point mutation in the bulge (+23) resulted in near wild-type competition (FIG. 4A, lane 8), but a deletion of the entire bulge region Δ(+23/+25) resulted in minimal competition being nearly as defective as the loop mutant (+31/+34) (FIG. 4A, lane 9). A similar series of gel retardation and competition, assays for TRP-185 was performed using sucrose gradient isolated TRP-185 and cofactor containing fractions (FIG. 4B). The pattern of competition for TRP-185 was similar to that seen using fractions from the hydroxylapatite column (FIG. 4B). This indicated that TRP-140 was not required for the binding properties of TRP-185. Competition curves and relative competition efficiencies for each of these constructs are shown in FIG. 4C.

Since the loop sequences appeared critical for the binding of TRP-185, the inventors used both hydroxylapatite and sucrose gradient fractions containing TRP-185 in gel retardation and competition analyses with wild-type TAR RNA and several loop point mutants (FIG. 5A and FIG. 5B). With the hydroxylapatite column fractions, the wild-type TAR RNA again resulted in marked competition for TRP-185 binding (FIG. 5A, lane 3) while the loop substitution mutant (+31/+34) resulted in only minimal competition (FIG. 5A, lane 4). Mutation of nucleotide (+30) in the loop resulted in only slight competition of TRP-185 binding, similar to the results obtained with the (+31/+34) loop substitution mutant, indicating the importance of this nucleotide in the loop for TRP-185 binding (FIG. 5A, lane 5). Mutation of nucleotide (+32) in the loop resulted in significant levels of competition of TRP-185 binding (FIG. 5A, lane 6) though less than was seen with wild-type TAR RNA while mutation of nucleotide (+34) resulted in intermediate levels of competition for TRP-185 binding (FIG. 5A, lane 7). None of these RNAs containing point mutations in the loop region resulted in significant competition for TRP-140 at the concentrations tested (FIG. 5A). Similar results were seen with sucrose gradient purified TRP-185 (FIG. 5B). Competition curves and relative competition efficiencies for each of these constructs are shown in FIG. 5C.

The results indicated that individual nucleotides in the loop region were critical for TRP-185 binding, but different nucleotides had somewhat variable effects on its binding. Though a point mutation in the bulge did not greatly alter TRP-185 binding, a deletion of the bulge resulted in marked decreases in its binding. In addition to determining regions of TAR RNA required for efficient TRP-185 binding, the binding affinity of TRP-185 was also calculated. The binding affinity ($K_d$) of TRP-185 to TAR RNA was calculated to be $3.15 \times 10^{-10}$M while its affinity to nonspecific RNA was $2.11 \times 10^{-5}$M (data not shown). Thus TRP-185 bound to TAR RNA with both high affinity and marked specificity.

EXAMPLE 5

RNA GEL RETARDATION ANALYSIS AND COMPETITION ANALYSIS OF TRP-185 BINDING

The present example is provided to demonstrate the competition between tat and TRP-185 for binding to the TAR RNA loop sequence. The particular protocols employed to demonstrate this competitive binding are (1) RNA gel retardation, and (2) competition analysis with tat protein.

For tat bacterial expression, DNA fragments encoding either wild type tat or tat 52/57[45] which contains the amino acids Gly Gly Ala Gly Gly Gly (SEQ ID NO:3) in place of the native amino acids ArgArg Gln Arg Arg Arg (amino acids 52–57) (SEQ ID NO:4) were used. By changing the sequence GAAATG encompassing the initiating methionine to AGATCT, a BglIII/EcoRI fragment of a tat subclone containing the second exon of tat was cloned into pGEX-2T (Smith and Johnson, 1988). Following cleavage with thrombin at the recognition motif between the GST-tat junction, tat proteins were generated and purified which consisted of amino acids 2 to 72 of tat preceded by Arg-Ser contributed by the BglIII sequence.

Purification of Bacterial Synthesized Tat Protein

Overnight cultures of wild-type or mutant tat(52/57) in pGEX-2T were diluted 1/100 in 500ml of fresh medium and grown to an O.D. of 0.6 at 37° C. The tat fusion proteins were induced by the addition of IPTG to a final concentration of 0.1 mM. Cultures were grown for four additional hours, the pellets harvested, and resuspended in 5 ml of 1×PBS (150 mM NaCl, 16 mM $Na_2HPO_4$, 4 mM $NaH_2PO_4$, pH 7.3) plus 0.5 mM PMSF and 1 mM DTT. Cells were lysed on ice by sonication, spun at 12,000 rpm for 15 min., and loaded on a 1 ml glutathione-Sepharose affinity column (Smith and Johnson, 1988). The column was washed with the above buffer and eluted with buffer containing 50 mM Tris (pH 8.0), 1 mM DTT and 5 mM glutathione. Fractions containing the tat fusion proteins were pooled, extensively dialyzed against PBS with 1 mM DTT, and loaded for a second passage on a glutathione-sepharose column. The column was washed with five column volumes of PBS with 1 mM DTT, five column volumes of buffer containing 50 mM Tris (pH 8.0), 150 mM NaCl, 2.5 mM CaCl$_2$, and 1 mM DTT, and then incubated with the same buffer and 6 μg of human thrombin (Sigma) for 40 min at room temperature with mixing. The flow through fractions which contained thrombin-released tat were collected and extensively dialyzed against 20 mM Tris (pH 7.9), 0.2 mM EDTA, 100 mM KCl, 20% glycerol, 1 mM DTT and 0.5 mM PMSF, then stored at −70° C.

Following dialysis to remove the CaCl$_2$ and after the addition of PMSF, no residual thrombin activity in tat preparations was demonstrated as judged by assays with other proteins containing thrombin recognition motifs. The presence of tat was confirmed by Western analysis with tat antisera (Pearson et al, 1990) and Coomassie staining of polyacrylamide SDS gels. The dissociation constants ($K_d$) and Scatchard analysis for tat binding to the TAR RNA wild-type and loop mutants were determined as described (Baker et al., 1986).

Characterization of Wild-Type and Mutant Tat Protein Binding to TAR RNA Templates In the described studies, it was established that tat regulated the binding of TRP-185 to TAR RNA. The possibilities addressed were whether both tat and TRP-185 bound simultaneously to TAR RNA or whether these proteins competed for binding to the TAR RNA. Both wild-type tat and a tat mutant (tat 52/57), which substituted six neutral amino acids (glycine and alanine) in the basic domain of tat between amino acids 52 and 57,[45] were produced as fusion proteins with glutathione S-transferase using the procaryotic expression vector pGEX.[48] These tat fusion proteins were purified by multiple passages on glutathione agarose affinity columns. Authentic tat proteins were liberated by removal of the glutathione S-transferase moiety following cleavage with thrombin at a recognition site engineered into the fusion protein. Both wild-type tat and tat 52/57 were judged to be greater than 95% pure and each preparation yielded a single species of approximately 9 kDa following gel electrophoresis and Coomasie staining. The purification of wild-type tat protein under these conditions eliminated harsh solution and denaturation procedures used in several other purification schemes, resulting in both a higher binding affinity and binding activity for TAR RNA than previously reported.[16, 28]

To first characterize the binding properties of these tat proteins, gel retardation analysis was performed with labeled TAR RNA derived from either wild-type, a loop mutant (+31/+34), a bulge point mutant (+23), or a bulge deletion mutant (+23/+25) (FIG. 6). All TAR RNA probes were labeled to the same specific activity. The wild-type tat protein bound to wild-type TAR RNA with a $K_a$ of 6.4×10$^{-10}$M. Scatchard analysis indicated that one tat molecule bound to each TAR RNA molecule and that all the binding sites of tat were active (FIG. 6A, lanes 1–5). tat 52–57 bound poorly to wild-type TAR RNA due to the fact that the majority of basic amino acids in the basic domain were substituted with neutral amino acids (FIG. 6A, lanes 6–10). These results were consistent with previous results, implicating the basic domain in tat for binding to TAR RNA.[16, 30 49]

Figure 6A:
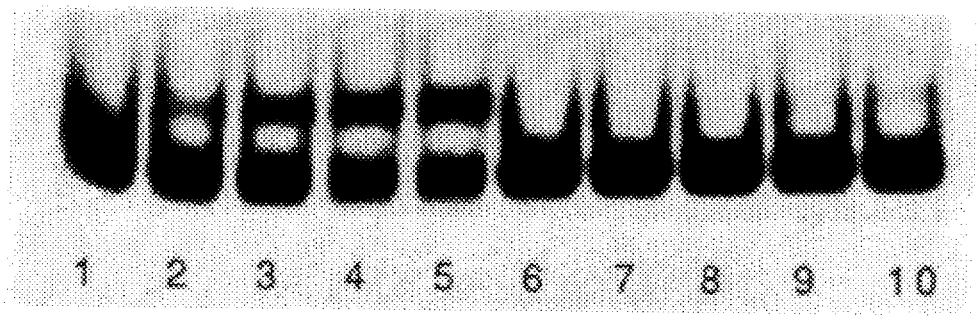
Figure 6B:
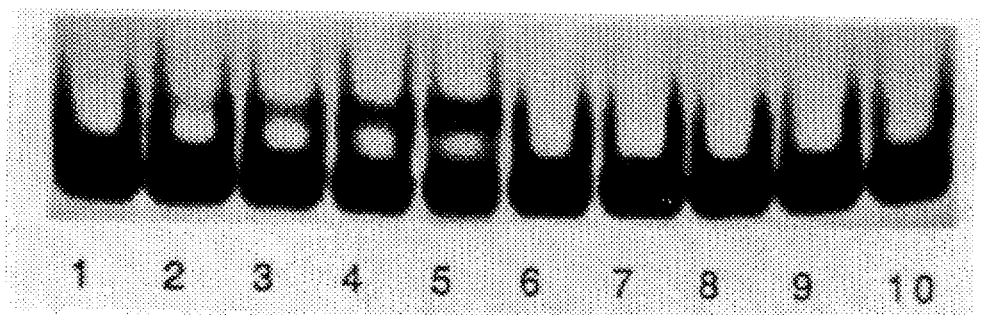
Figure 6C:
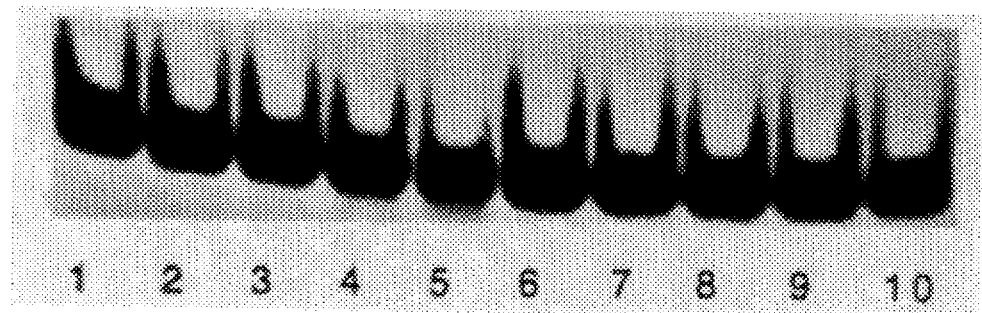
Figure 6D:

Next the inventors determined the binding of these tat proteins to the TAR RNA loop substitution mutant (+31/+34). The wild-type tat protein bound to this TAR RNA mutant with five-fold lower affinity than to wild-type TAR RNA (FIG. 6B, lanes 1–5). Similar results have previously been noted using tat peptides in gel retardation analysis with a similar TAR RNA loop mutant.[49] tat 52/57 did not bind to this template (FIG. 6B, lanes 6–10). TAR RNA containing either a point mutation in the bulge at (+23)(FIG. 6C, lanes 1–10) or a deletion of the bulge region (+23/+25) (FIG. 6D, lanes 1–10) did not result in detectable binding of either wild-type tat or tat 52/57. These results were consistent with previous studies which indicated a predominant role for the bulge region in tat binding,[16, 28, 30, 49] but also suggested that wild-type loop sequences influenced the affinity of tat binding to TAR RNA.

Tat Competes with TRP-185 for Binding to TAR RNA

TRP-185 was demonstrated to require an intact TAR RNA stem and bulge structure and wild-type loop sequences for efficient binding. The inventors also determined whether the addition of either wild-type tat or tat 52/57 influenced the binding of TRP-185 to TAR RNA. Gel retardation analysis was performed with a constant amount of TRP-185 and increasing amounts of wild-type tat protein added to labeled wild-type TAR RNA. As increasing amounts of tat bound to the TAR RNA, there was decreased binding of TRP-185 to the TAR RNA (FIG. 7A, lanes 1–5). No evidence for simultaneous binding of both tat and TRP-185 to TAR RNA was noted. This result suggested that tat was able to complete with TRP-185 for binding to TAR RNA. This result was further substantiated by gel retardation with wild-type TAR RNA using similar amounts of tat 52/57 and TRP-185. This tat mutant, which was unable to bind efficiently to TAR RNA, did not reduce the binding of TRP-185 to TAR RNA (FIG. 7B, lanes 1–5). The addition of purified glutathione S-transferase protein obtained during the tat purification also did not decrease the binding of TRP-185 to TAR RNA (FIG. 7C, lanes 1–5). Finally, the wild-type tat protein did not decrease the binding of TRP-185 when a TAR RNA bulge point mutant template (+23) was used in gel retardation analysis (data not shown). These results suggested that tat competed with TRP-185 for binding to TAR RNA. A direct interaction between TRP-185 and tat which is independent of TAR RNA is possible. Due to the proximity of the bulge and loop regions and the fact that the binding affinity for both of these proteins is similar (between 3×10$^{-10}$ and 6×10$^{-10}$), stearic effects may be responsible for the fact that only tat or TRP-185 can bind in vitro to each TAR RNA template. However, it cannot be ruled out that high affinity binding of tat to TAR RNA requires the loop sequences in addition to the bulge region and this binding of tat to the loop sequences could potentially inhibit TRP-185 binding. Mutations in the upper portion of TAR RNA including the loop or bulge regions may dramatically influence TAR RNA structure with subsequent effects on the ability of both cellular and vital proteins to bind to TAR RNA. Thus, the in vivo phenotype of the TAR RNA loop and bulge mutations may be due to decreased binding of either TRP-185 and/or tat.

EXAMPLE 6

TRP-185 STIMULATION OF HIV GENE EXPRESSION

The present example demonstrates that TRP-185 stimulates gene expression from a wild-type HIV-LTR template. However, no stimulation of gene expression from an HIV template containing mutations in TAR was shown. These results indicate TRP-185 is a cellular factor that is regulated by the tat protein and which is involved in modulating the level of HIV gene expression.

In Vitro Transcription of the HIV LTR

HIV constructs in pJGFCAT18 extending from −179 to +80 were restricted with NcoI to generate a 620bp run-off transcript. The TAR-antisense construct (Garcia et al. 1989) was restricted with EcoRI to generate a 290 bp run-off transcript. Transcription reactions were performed in 10 mM Hepes, pH 7.9, 10 mM Tris (pE 7.9), 10% glycerol, 50 mM KCl, 0.1 mM EDTA, 1 mM DTT, 5 mM $MgCl_2$, 10 mM creatine phosphate, 0.5 µg of poly (I)-poly (C), and 600 mM each of ATP, CTP, UTP, 40µM GTP, and 1 µ of $[\alpha^{32}P]$ GTP (3000 Ci/m mole). HeLa nuclear extract (Dignam et al., 1983)(100 µg) was included in each reaction and incubated at 30° C. for 1 hr. The final α-amanitin concentration was 2.0 µg/ml where indicated. Either 0.6 µg of TRP-185 fraction from a sucrose gradient preparation or 10µl of cofactor fractions was included to determine the effects of TRP-185 on activation of the HIV LTR. All reactions were stopped by the addition of 400µl of 7M urea, 0.35M NaCl, 0.01 mM EDTA, 0.1M Tris (pH 7.4), and 1% SDS. The supernatant was extracted with phenol-chloroform and ethanol precipitated in the presence of oyster glycogen. Reaction products were electrophoresed on a 5% polyacrylamide sequencing gel containing 8M urea in 1×TBE. Gels were exposed overnight at −70° C. with an intensifying screen.

TRP-18B Stimulates Gene Expression From the HIV LTR

The role of TRP-185 in stimulating in vitro transcription of the HIV LTR was next assayed. In vitro transcription assays were performed with a concentration of magnesium (5 mM) which favored the synthesis of full-length transcripts from the HIV LTR. A wild-type HIV LTR CAT template when restricted with NcoI generates a run-off transcript of 620 bp which is inhibited by 2 µg/ml final concentration of alpha amanitin.

Figure 8:
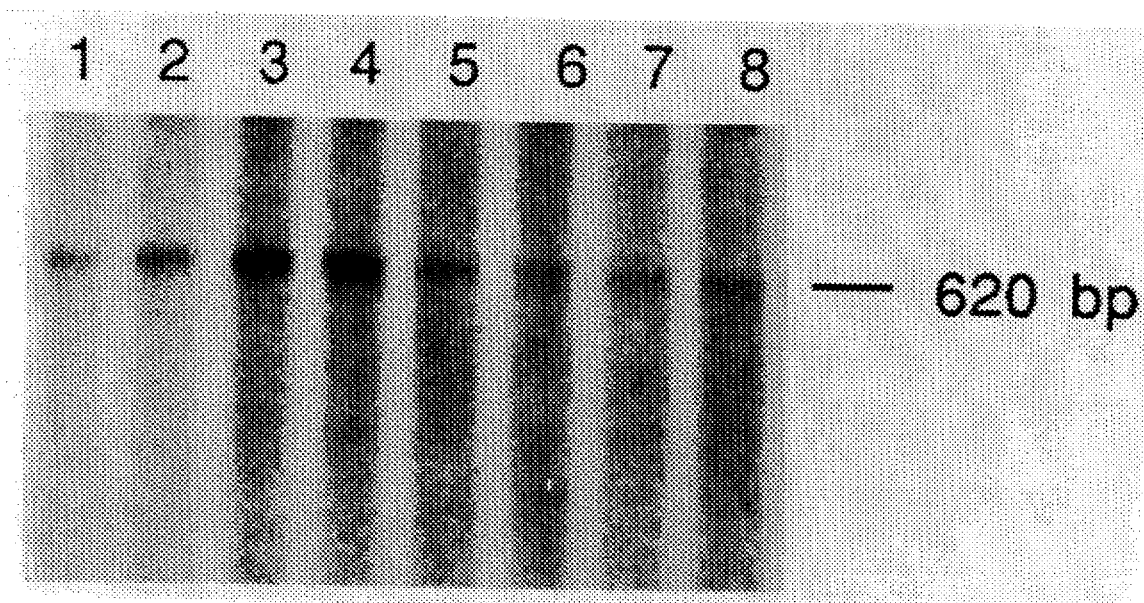
Figure 9A:
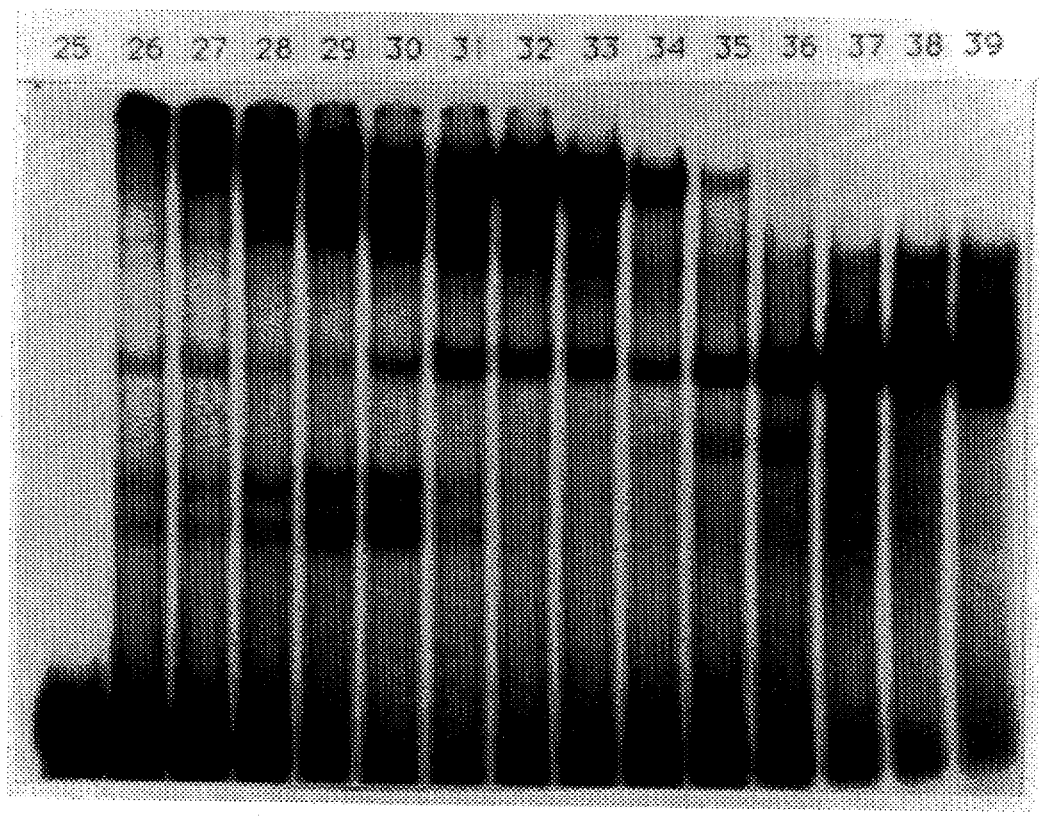
Figure 9B:
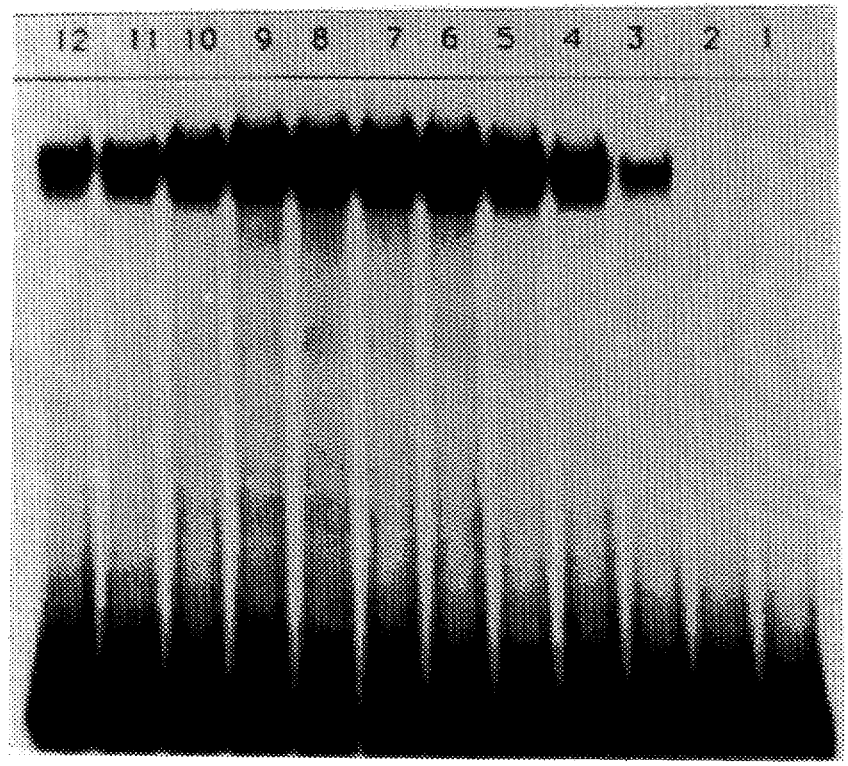
Figure 9C:
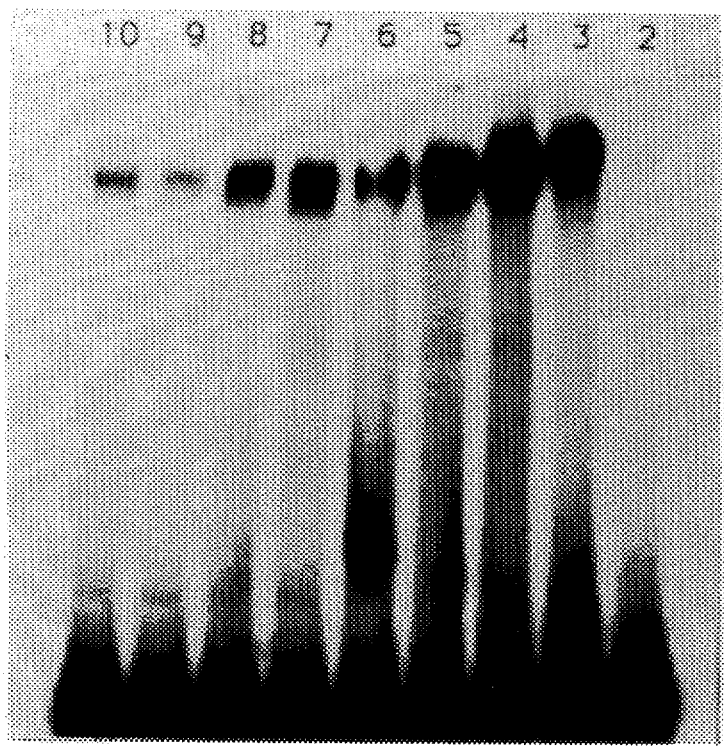
Figure 9D:
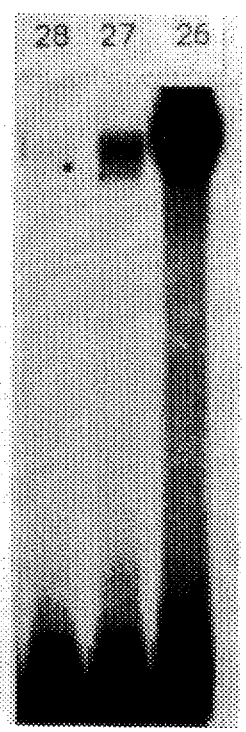
Figure 9E:
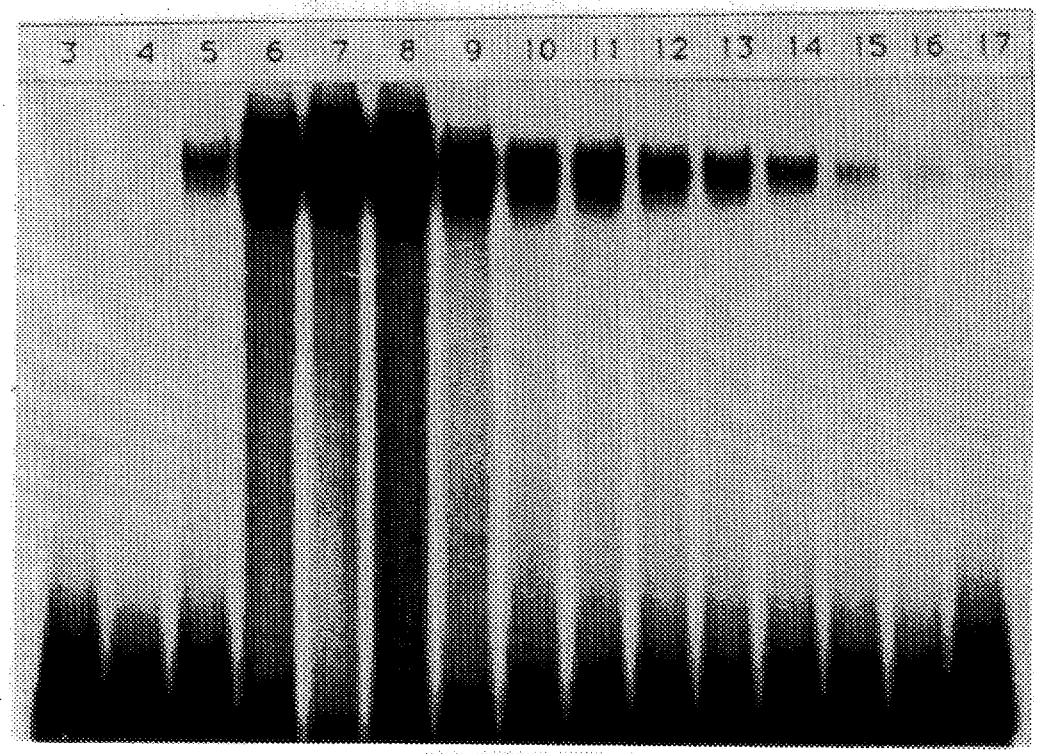

Both wild-type and a TAR mutant containing a deletion of the bulge (+23/+25) were restricted with NcoI. Addition of HeLa cell nuclear extract alone resulted in low level synthesis of the 620 bp RNA species from both the wild-type and (+23/+25) templates (FIG. 8, lanes 1 and 5). There was minimal stimulation of transcription with the addition of the cofactor fraction with the wild-type but not the (+23/+25) template (FIG. 8 lanes 2 and 6). However, the addition of either TRP-185 alone or TRP-185 and cofactor resulted in approximately a four-fold increase in in vitro transcription from the wild-type (FIG. 8, lanes 3 and 4) but not the (+23/+25) construct (FIG. 8, lanes 7 and 8).

Since tat is able to regulate the binding of TRP-185 to TAR RNA, it is critical to determine the function of TRP-185. Addition of TRP-185 to HeLa nuclear extract results in the stimulation of in vitro transcription from the HIV LTR. Though the level of activation is only four-fold, it must be noted that HeLa nuclear extract contains significant amounts of both cofactor and TRP-185. It is likely that a much greater level of transcriptional activation may be obtained with completely reconstituted extracts. In the present studies the inventors were unable to obtain significant additional stimulation by the addition of tat protein to in vitro transcription assays as previously described.[33] The conditions used in the in vitro transcription assays do not address whether TRP-185 is involved primarily in the stimulation of HIV LTR transcriptional initiation and/or elongation.[25] Furthermore, these studies do not address the role of tat in terms of its role on in vitro transcription of the HIV LTR.

A model consistent with the inventors data and previous studies would suggest that TRP-185 may be a crucial factor for the formation of or efficient processing of the cellular transcription complex assembled on the HIV promoter. In this model, TRP-185 would interact with the loop of the nascent TAR RNA transcribed from the HIV LTR to form a complex which can proceed slowly and as such becomes rate determining. Binding of tat to the bulge region as it arises during the formation of TAR RNA would then cause the release of TRP-185 from the loop region with subsequent catalytic effects on the transcriptional initiation and/or elongation process. The provided in vitro transcription analysis indicates that TRP-185 stimulates gene expression from a wild-type HIV LTR template but not an template containing mutations in TAR. Thus, TRP-185 is a likely candidate for a cellular factor which is regulated by the tat protein and is involved in modulating the level of HIV gene expression.

EXAMPLE 7

BINDING OF TRP-185 TO CELLULAR NUCLEIC ACID

The present example is provided to demonstrate the binding affinity which TRP-185 protein may have for cellular nucleic acid species. As TRP-185 is a cellular protein, and in light of the regulatory action the inventors have demonstrated it to have in viral gene expression/binding of viral RNA, it is contemplated by the present inventors that TRP-185 may also be binding a small class of conserved cellular nucleic acid sequences.

Evidence collected in support of this observation include the molecular "footprinting" of initiation regions of cellular DNA nucleic acid from adenovirus, as well as with HIV DNA, with TRP-185 cellular protein (see FIG. 11).

The inventors demonstrate in this example that highly purified fractions of TRP-185 bind strongly to elements of cellular promoters near the "initiation element". Thus, the TRP-185 cellular protein, already demonstrated to regulate viral promoters, may also regulate cellular promoters. Highly conserved regions of, for example, the adenovirus, located downstream of the promoter region, may also be activated by the binding of a cellular protein, in a manner similar to that of TRP-185, to affect gene expression. TRP-185 does in fact bind downstream of a promoter region to a nucleic acid region which is known to be of a highly conserved sequence. This or a similar mechanism may be acting to bind cellular genes and control cellular gene expression.

EXAMPLE 8

PROPOSED METHOD FOR PREPARING A THERAPEUTIC AGENT FOR THE TREATMENT OF AIDS

The present prophetic example is provided to outline a method which may be used to treat patients infected with the HIV or HTLV virus. The TRP-185 cellular protein is demonstrated to enhance HIV gene expression by binding a particular TAR region of the HIV RNA LTR. This binding downstream of the promoter region is critical to vital gene expression. Therefore, the use of specific inhibitors of TRP-185 would shut-off viral gene expression, thereby serving as a therapeutic agent for persons infected with the virus.

TRP-Inhibitors

A TRP-185 inhibitor as a therapeutic agent for AIDS and related diseases, such as during ARC, may be administered as a capsule, as a powder to be reconstituted for subcutaneous or intramuscular administration.

The inhibitor of TRP-185 cellular protein may take the form of an antibody specific for TRP-185 (as described in example 3), a competing protein or peptide which has specific binding affinity for the same TAR RNA binding site, a peptide or protein which dephosphorylates TRP-185 cellular protein, an antisense oligonucleotide specific for the TAR RNA binding site of TRP-185 cellular protein, a DNA or RNA fragment that preferentially binds the TRP-195 protein, a protein or peptide which acts to modify a TRP-185 protein so as to prevent the binding of the TRP-185 to its specific TAR RAN binding site, or a molecule that prevents TRP-185 binding and activation from the TAR region.

EXAMPLE 9

METHOD FOR ISOLATING AND CLONING THE GENE ENCODING TRP-185 PROTEIN

The purification and cloning of TRP-185 and its associated cofactor species will be required to address the potential roles of these proteins in mediating tat activation of the HIV LTR. Thus, the present example provides an outline of a procedure used to accomplish this task. In addition Example 12 demonstrates an alternative means of cloning a TRP-185 gene.

The methods and procedures outlined in the AMERSHAM®3 SUPERSCREEN® Immunoscreening protocol may be employed together with the monoclonal antibodies for TRP-185 described herein at example 3. More specifically, the referenced system may be used for screening λ-gt11 libraries with monoclonal antibodies raised to TRP-185 (outlined in Example 3).

Briefly, the human gene encoding the TRP-185 protein of the present invention may be obtained by first obtaining, for example, a human chromosomal cDNA library (Clonetech Laboratories Inc., 4030 Fabian Way, Palo Alto, Calif. 94303). Alternatively, one may prepare their own human chromosomal cDNA library employing those techniques available to those in the art.[54, 56] The gene which encodes TRP-185 will be detectable by employing a human chromosomal cDNA library as it is known by the work of the present inventors that TRP-185 is a cellular as opposed to vital protein.

The human chromosomal cDNA library will be screened by allowing the recombinant λ-gt11 phage to grow and to form plaques in top agar in a petri dish using *E. coli* as the host. The plaques will then be transferred to a, for example, nitrocellulose filter impregnated with IPTG to induce expression, as described in the AMERSHAM® kit.[53] The nitrocellulose filters will then be incubated in the presence of a nonspecific protein. By way of example, such a nonspecific protein would be borne serum albumin (BSA).

The nitrocellulose filters (which include the formed plaques) will then be exposed to the TRP-185 specific antibody prepared as described in Example 3. A second, detectably labeled antibody would also be exposed to the filters. The second antibody would be specific for the TRP-185 specific antibody (the "first" antibody). By way of example, such a second detectably labeled antibody may constitute a horseradish peroxidase labelled second antibody.

Addition of the substrate (for example, the substrate 3.3' diaminobenzidine tetrahydro-chloride (DBA) or hydrogen peroxide where horseradish peroxidase is the detectable label of the second antibody) for the second detectably labeled antibody will provide for the development of a "positive" signal of the TRP-185 plagues. The original plaques formed which correspond to the TRP-185 +plagues will then be selected for further purification and rescreening to check and isolate the TRP-185 +clones. The DNA sequences from the obtained TRP-185 +clones may then be excised and further characterized. Such further characterization may include the preparation of expression vectors containing the DNA from TRP-185 +clones. Upon preparation of the expression vectors with the TRP-185 DNA sequence, the protein products expressed may be isolated and tested against a monoclonal antibody specific for the TRP-185 protein (antibody preparation described in Example 3).

According to this method, one skilled in the art of gene cloning and isolation may obtain the human gene encoding the TRP-185 cellular protein which is capable of binding TAR RNA of HIV described in the present invention.

PROPHETIC EXAMPLE 10

IMMUNODIAGNOSTIC ASSAY FOR HIV INFECTION

The present example outlines a method which may be useful for the diagnosis and clinical monitoring of the progression of an HIV infection, such as AIDS, in a human. The method employs the monitoring of the levels of, for example, antibodies specific for the TRP-185 cellular protein. At least two forms of the TRP-185 as antigen will be used in the assay including TRP-185 as antigen without exposure/treatment with a cofactor fraction and with exposure to a cofactor fraction. The presence of antibody specific for each of these TRP-185 forms of antigen in a biological sample, such as blood will then be determined using standard immunoassay techniques.

By determining the presence of antibodies to TRP-185-cofactor exposed antigen and to TRP-185 antigert not exposed to cofactor, the assay may indicate the relative diseased state of the patient during the progression of the disease. In order to be used as a diagnostic tool for HIV or HTLV infection, a control value for antibody to TRP-185 as antigen in the system of a healthy, non-EIV infected population of samples will be established. TRP-185 is a cellular protein which is present in a normal healthy animal and which also is likely to have a function in the "turning off/turning on" of cellular genes of the animal (see Example 7), apart from its additional action in binding HIV TAR RNA and enhancing vital gene expression. As an immunodiagnostic assay, an animal sample to be tested would first be obtained and a volume thereof incubated with an amount of TRP-185 cofactor exposed antigen, as well as with an amount of TRP-185 antigen which had not been exposed to antigen.

Preparation of TRP-185 cofactor exposed binding protein as antigen

According to one proposed pretreatment of the TRP-185 as antigen, the preparation of TRP-185 defined in Example 1 may be incubated with cofactor fraction for about 5 minutes at room temperature.

The exposure of TRP-185 binding protein to a cofactor fraction (as defined in Example 2) is expected to chemically change the TRP-185, (perhaps phosphorylate), and therefore potentially change the tertiary structure of the TRP-185 so as to exposed different antigenic sites. Therefore, the exposed/modified TRP-185 could elicit antibodies with specificity that differs from those antibodies elicited by unmodified TRP-185.

Preparation of TRP-185 Binding Protein as Antigen

TRP-185 will be prepared from mammalian cells as described in Example 1. For this assay, two preparations of monoclonal antibodies would be prepared as described in Example 3, using the cofactor exposed-TRP-185 and cofactor unexposed TRP-185 as antigen. These separate antibody preparations could then be used, along with its corresponding antigen, in establishing the level of either antibody in an animal sample.

A standard curve for each of the TRP-185 antigens which includes an amount of the specific (i.e., antibody against exposed/not exposed) anti-TRP-185 antibody will be prepared.

It is expected that the relative amount of antibody specific for the cofactor exposed TRP-185 antigen will greater than the relative amount of the antibody specific for the TRP-185 antigen (without cofactor exposure) in a biological sample with the increasing progression of an HIV or HTLV infection in the patient. This assay may be used in conjunction with the therapeutic agents of the present invention (Example 8) to monitor the effectiveness of the agent in reducing/eliminating the gene activating form (a phosphorylated form) of the TRP-185 cellular protein.

While those of skill in the art will be able to practice the present invention with the aid of the disclosure provided here, the following references may facilitate practice or enhanced understanding of certain aspects. Inclusion of a reference in this list is not intended to and does not constitute an admission that the reference constitutes prior art with respect to the present invention.

EXAMPLE 11

CHARACTERIZATION OF COFACTOR FRACTION

The flow-through fractions from the Bio-Rex 70 column were pooled and found to contain 36, 41, 42, 43, 45 and 47 kD molecular weight proteins, while the bound fraction from the Bio-Rex 70 column contained the 53, 55, 58, 60 and 85 kD molecular weight proteins. However, both the flow-through and the bound proteins of the cofactor fraction were found to be necessary to reconstitute TRP-185 binding activity to HIV-RNA (see FIG. 13). Neither the flow-through fractions nor the bound fractions of the cofactor fraction alone was sufficient to elicit binding of the TRP-185 to HIV-TAR RNA (see FIG. 13).

The further purification of the proteins of the flow-through and bound fractions of the cofactor fraction were further fractionated into individual components and found to result in the loss of biological activity, as measured by loss in TRP-185 binding to TAR sequences. In addition, the individual isolated proteins of the cofactor fraction were found to be unstable. FIG. 13 is an RNA gel retardation analysis using TAR RNA with the various eluted and bound fractions obtained with the cofactor fractions. As can be seen in Lane 1 of the gel, the TRP-185 did not bind TAR PaNA in the absence of the cofactor fraction. Lane 2 of the gel demonstrates that TRP-185 did not bind TAR RNA in the presence of the cofactor fractions that eluted from a Bio-Rex 70 column (flow-through fractions). Lane 3 of the gel demonstrates that TRP-185 also did not bind TAR RNA in the presence of the cofactor fraction that bound to the Bio-Rex 70 column. However, as demonstrated in Lane 4 of FIG. 13, the TRP-185 did bind TAR RNA in the presence of both the eluted cofactor fraction and bound cofactor fraction.

The present inventors have therefore determined that the combination of the individually characterized proteins that make up the cofactor fraction were necessary to preserve the biological activity of the cofactor fraction for facilitating TRP-185 binding to HIV TAR RNA.

From these studies, the inventors have determined that the cofactor fraction prepared according to the present invention, is a combination of individual cofactors, and is responsible for enhancing the binding of TRP-185 to TAR HIV RNA.

Purification of Cofactors

A nuclear extract was prepared as described in Digham, et al. 1983. Nuclear extract prepared from 60 liters of HeLa cells was applied to heparin agarose column (2.5×9cm) equilibrated with buffer A (20 mM Tris (pH 7.9), 20% glycerol, 0.2 mM EDTA) containing 0.1M KCL, 0.5 mM DTT and 0.5 mM PMSF. The column was washed in the same buffer and then eluted with buffer A with 0.5M KCL, 0.5 mM DTT and 0.5 mM PMSF. The 0.4M KCL buffer A fractions were pooled and a dialysis versus buffer A with 0.1M KCL, 0.5 mM DTT and 0.5 mM PMSF. This dialyzed fraction was applied to HTP biogel column (2.5×7 cm) in the same buffer and washed. The column was eluted with buffer containing 0.1M potassium phosphate (pH 7.0). The bound fractions were pooled and 70% ammonium sulphate precipitated and centrifuged at 12,000 RPM for 20 minutes. The precipitate was resuspended in 6 ml buffer A with 0.1M KCL, 1 mM DTT and loaded on a Superdex 200 FPLC column equilibrated in the same buffer. The fractions containing cofactors that were able to reconstitute TRP-185 binding activity were pooled and applied to a 5 ml Q-Sepharose column equilibrated in the same buffer.

The flow-through pooled fractions contained cofactors, having molecular weights of 36, 41, 42, 43, 45, 47, 53, 55, 58, 60 and 80 Kd. This flow-through fraction was further fractionated on a 3ml Bio-Rex 70 column. The flow-through pooled fraction contains the cofactors of 36, 41, 42, 43, 45, 47 Kd and the bound fraction contained cofactors with the molecular weight of 53, 55, 58, 60 and 85 Kd. Both the flow-through and the bound fractions were able to reconstitute TRP-185 binding activity, the combination of both gave the best results. The cofactors fractions do not bind HIV TAR RNA, and further purification of these proteins into individual components also inactivate as cofactor. The proteins were unstable individually and reconstitution of these to restore cofactor activity was not successful. The combination of the above proteins were required to be active as cofactors.

EXAMPLE 12

NUCLEIC ACID SEQUENCE AND AMINO ACID SEQUENCE FOR TRP-185 DERIVED PEPTIDE

The present example outlines the protocol which was employed to obtain both the amino acid sequence and the nucleic acid sequence for full length TRP-185, as confirmed by northern blot analysis from a TRP-185 derived peptide. Briefly, TRP-185 protein was purified, and short peptides were isolated and sequenced. Degenerate oligonucleotides were derived using the peptide sequences and used to amplify a DNA that was subcloned in pUC19 and sequenced. The present example describes the best mode known to the inventors for obtaining the amino acid sequence and the nucleic acid sequence of the TRP-185 binding protein of the present invention.

Figure 14:
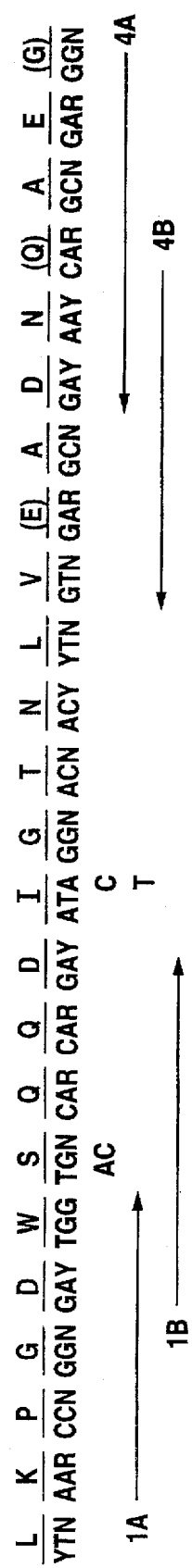

Degenerate oligonucleotides may be selected from any portion of any of the sequences disclosed herein. However, for the cloning of TRP-185, degenerate oligonucleotides were derived that coded for the amino acid sequence that was derived from peptide fragments of TRP-185 as shown in FIG. 14. TRP-185 may be cloned using oligonucleotides derived from the sequence as set forth in SEQ ID NO:1 and to select any continuous portion of the sequence, from about 10 nucleotides in length up to and including the full length sequence. The primers used to clone TRP-185 as disclosed herein are those identified by SEQ ID NOS:6–9 based on the degenerate sequence of SEQ ID NO:5.

The process of selecting and preparing a nucleic acid segment which includes a sequence from within SEQ ID NO:1 may alternatively be described as preparing a nucleic acid fragment. Of course, fragments may also be obtained by other techniques such as, e.g., by mechanical shearing or by restriction enzyme digestion. The inventors prepared small nucleic acid segments or fragments as may be readily prepared by, for example, directly synthesizing the fragment by chemical means, as is commonly practiced using an automated oligonucleotide synthesizer. Fragments were obtained by application of nucleic acid reproduction technology, such as the PCR technology of U.S. Pat. No. 4,683,202 (incorporated herein by reference), by introducing selected sequences into recombinant vectors for recombinant production, and by other recombinant DNA techniques generally known to those of skill in the art of molecular biology and as described hereinbelow.

Isolation of a Full-Length TRP-185 cDNA and Determination of the Nucleotide Sequence To obtain a full-length cDNA of TRP-185, a HeLa cDNA library was screened using the originally isolated TRP-185 PCR fragment that was cloned into pUC19 as a probe. The HeLa cDNA library was prepared by cloning cDNAs into λgt10 using EcoRI linkers. The library was amplified to greater that 108 p.f.u./ml and one million plaques were screening using a $^{32}$P labeled TRP-185 PCR probe and a full length TRP-185 insert isolated.

DNA Sequencing

After restriction mapping of the TRP-185 cDNA clone, the nucleotide sequences was determined for both cDNA strands. Sequencing was performed with the Sequenase version 2.0 sequencing kit (U.S. Biochemical Corp., Cleveland, Ohio).

Computer analyses of the nucleotide and amino acid sequence

The nucleotide (SEQ ID NO:1) and the deduced amino acid (SEQ ID NO:2) sequences derived from the TRP-185 cDNA clone were compared to known sequences in the databases using BLAST network service of the National Center for Biotechnology Information (NCBI).

Northern Blot Analysis

Northern blotting analyses of the gene TRP-185. Total RNA was loaded per lane on an agarose/formaldehyde gel, transferred to a solid support matrix and hybridized with the 32P-labeled TRP-185 cDNA clone.

Figure 15:
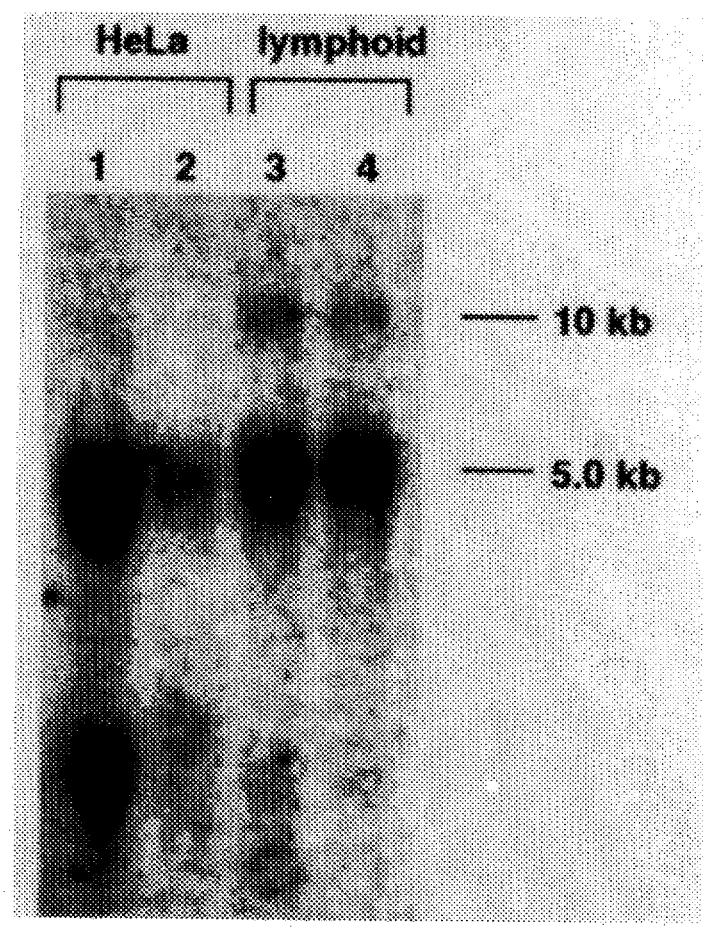

The TRP-185 peptide was purified from HeLa cells according to the protocol in Example 1; 20 μg of the protein was digested with protease lysE, and the peptides generated were subject to amino acid sequence analysis. The peptide, as shown in FIG. 14, was used to derive oligonucleotides which were used to clone the full length TRP-185 message. Furthermore the cDNA was used as a probe for northern analysis (FIG. 15). The TRP-185 probe hybridized to RNA from HeLa and Jurkat cells yielding a 5.0 kb hybridizing mRNA. In addition, a 10 kb mRNA which may reflect a related messenger RNA was also present in Jurkat cells (FIG. 15) indicating that TRP-185 mRNA and protein is present in both HeLa and Jurkat cells and that the cDNA cloned was a full length cDNA.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

1. Rosen, C. A., J. G. Sodroski, and W. A. Haseltine (1985), *Cell*, 41:813–823.
2. Jones, K. A., J. T. Kadonga, P. A. Luciw, and R. Tjian (1986), *Science*, 232:755–759.
3. Garcia, J. A., F. K. Wu, R. Mitsuyasu, and R. B. Gaynor (1987), *EMBO J.*, 6:3761–3770.
4. Nabel, G., and Baltimore (1987), *Nature* (London), 326:711–713.
5. Feng, S., and E. C. Holland (1988), *Nature*, 334:165–167.
6. Jakobovits, A., D. H. Smith, E. B. Jakobovits, and D. J. Capon (1988), *Mol. Cell. Biol.*, 8:2555–2561.
7. Jones, K. A., P. A. Luciw, and N. Duchange (1988), *Genes & Der.*, 2:1101–1114.
8. Wu, F. K., J. A. Garcia, D. Harrich, and R. B. Gaynor (1988), *EMBO J.*, 7:2117–2130.
9. Berkhout, B., and K. T. Jeang (1989), *J. Virol.*, 63:5501–5504.
10. Garcia, J. A., D. Harrich, E. Soultanakis, F. Wu, R. Mitsuyasu, and R. B. Gaynor (1989), *EMBO J.*, 8:765–778.
11. Harrich, D., J. Garcia, F. Wu, R. Mitsuyasu, and R. B. Gaynor (1989), *J. Virol.*, 63:2585–2591.
12. Hauber, J., and B. R. Cullen (1988), *J. Virol.*, 62:673–679.
13. Selby, M. J., E. S. Bain, P. A. Luciw, and B. M. Peterlin (1989), *Genes & Der.*, 3:547–558.
14. Ratnasabapathy, R., M. Sheldon, L. Johal, and N. Hernandez (1990), *Genes & Der.*, 4:2061–2074.
15. Roy, S., N. T. Parkin, C. Rosen, J. Itovitch, and N. Sonenberg (1990a), *J. Virol.*, 64:1402–1406.

16. Roy., S., U. Delling, C. H. Chen, C. A. Rosen, and N. Sonenberg (1990b), *Genes & Der.*, 4:1365–1373.
17. Siekevitz, M., S. F. Josephs, M. Dukovich, N. Peffer, F. Wong-Staal, and W. Greene (1987), *Science*, 238:1575–1578.
18. Crabtree, G. R. (1989), *Science*, 243:355–361.
19. Tong-Starksen, S. E., P. A. Luciw, and B. M. Peterlin (1987), *Proc. Natl. Acad. Sci. USA*, 84:6845–6851.
20. Braddock, M., A. Chambers, W. Wislon, M. P. Esnouf, S. E. Adams, A. J. Kingsman and S. M. Kingsman (1989), *Cell*, 58:269–279.
21. Harrich, D., J. Garcia, R. Mitsuyasu, and R. B. Gaynor (1990), *EMBO J.*, 9:4417–4424.
22. Haseltine (1986), *Cell*, 44:941–947.
23. Fisher, A. G., M. B. Feinberg, S. F. Josephs, M. E. Harper, L. M. Marselle, G. Reyes, M. A. Gonda, A. Aldovini, C. Debouk, R. C. Gallo, and F. Wong-Staal (1986), *Nature*, 320:367–371.
24. Rice, A. P., and M. B. Mathews (1988), *Nature* (London), 332:551–553.
25. Laspia, M. F., A. P. Rice, and M. B. Mathews (1989), *Cell*, 59:283–292.
26. Marciniak, R. A., M. A. Garcia-Blanco. and P. A. Sharp (1990), *Proc. Natl. Acad. Sci.*, 87:3624–3628.
27. Berkhout, B., R. H. Silverman, and K. T. Jeang (1989), *Cell*, 59:273–282.
28. Dingwall, C., I. Ernberg, M. J. Gait, S. M. Green, S. Heaphy, J. Karn, A. D. Lowe, M. Singh, M. A. Skinner (1990), *EMBO J.*, 9:4145–4153.
29. Dingwall, C., I. Ernberg, M. J. Gait, S. M. Green, S. Heaphy, J. Karn, A. D. Lowe, M. Singh, M. A. Skinner, and R. Vallerio (1989), *Proc. Natl. Acad. Sci.*, 86:6925–6929.
30. Weeks, K. M., C. Ampe, S. C. Schultz, T. A. Steitz, and D. M. Crothers (1990), *Science*, 249:1281–1285.
31. Gatignol, A., A. Kumar, A. Rabson, and K. T. Jeang (1989), *Proc. Natl. Acad. Sci.*, 86: 7828–7832.
32. Gaynor, R., E. Soultanakis, M. Kuwabara, J. Garcia, and D. S. Sigman. (1989), *Proc. Natl. Acad. Sci.*, 86:4858–4862.
33. Marciniak, R. A., B. J. Calnan, A. D. Frankel, and P. A. Sharp (1990), *Cell*, 63: 791–802.
34. Goodman and Gilmans, *The Pharmacological Basis of Therapeutics*, 8th Ed. (1990), Gilman, Rall, Niesand, Taylor, editors: pp 1182 –1201.
35. Digham, J. D., R. M. Lebovitz, and E. G. Roeder (1983), *Nucl. Acids. Res.*, 11: 1475–1489.
36. Jakobovits, A., A. Rosenthal, and D. J. Capon (1990), *EMBO J.*, 9:1165–1170.
37. Southgate, C., M. L. Zapp, and M. R. Green (1990), *Nature*, 345:640–642.
38. Bhattacharyya, A., A. I. H. Murchie, and D. M. J. Lilley (1990), *Nature*, 343:484–487.
39. Takagaki, Y., J. L. Manley, C. C. MacDonald, J. Wilusz, and T. Shenk (1990), *Genes & Der.*, 4:2112–2120.
40. Wilusz, J., T. Shenk, Y. Takagaki, and J. L. Manley (1990), *Mol. Cell. Biol.*, 10:1244–1248.
41. Baker, R. E., O. Gabrielsen, and B. D. Hall (1986), *J. Biol. Chem*, 261:5275–5282.
42. Lazinski, D., E. Grzadzielska, and A. Das (1989), *Cell*, 59:207–218.
43. Gorman, C. M., L. F. Moffat, and B. H. Howard, (1982) *Mol Cell. Biol.*, 2: 1044–1051.
44. Selby, M. J., and B. M. Peterlin (1990), *Cell*, 62:769–776.
45. Modesti, N., J. A. Garcia, C. Debouck, B. M. Peterlin, and R. Gaynor (1991), *New Biologist*, 3:759–768.
46. Cullen, B. R. (1986), *Cell*, 46:423–426.
47. Field et al. (1988), *Molecular and Cellular Biology*, 8 (5):2159–2165.
48. Smith and Johnson (1988), *Gene*, 67:31–40.
49. Calnan, B. J., S. Biancalana, D. Hudson, and A. D. Frankel (1991), *Genes and Development* 5:201–210.
50. Gaynor, R. (1991), *Advances in Mol. Biol. and Targeted Treatment for AIDS*, A. Kumar, Ed. Plenum Press, New York. pp 79–90.
51. Harlow, E. and D. Lane. (1988) *Antibodies, a Laboratory Manual*. Cold Spring Harbor Laboratory
52. Fields et al., editors (1985), *Fundamental Virology*; Raven Press, pp. 681–707.
53. AMERSHAM® Catelog, SUPERSCREEN Immunoscreening System (1991)
54. Kimmel, A. R. and Berger, S. L. (1987) *Meth. Enzymol.*, 152:307.
55. Okayama, H. and Berg. P. (1982) *Mol. Cell. Biol.*, 2:161.
56. Gubler, U. and Hoffman, B. J. (1983), *Gene*, 25:283.
57. Smale, S. T. and Baltimore (1989), *Cell*, 57:103–115.
58. Sambrook, J., Fritsch, E. F., Maniatis, T. (1989) in *Molecular Cloning*: A laboratory manual. Cold Spring Harbor Laboratory Press, Cold Spring Harbor, N.Y.

---

What is claimed is:

1. An isolated nucleic acid encoding the amino acid sequence set forth in SEQ ID NO:2 or degenerate variants thereof.

2. The isolated nucleic acid of claim 1 having a sequence of SEQ ID NO:1 or a nucleotide residue sequence fully complementary thereto.

3. The isolated nucleic acid of claim 1, substantially free of nucleic acid sequence not encoding SEQ ID NO:1.

4. The isolated nucleic acid of claim 1, further defined as a DNA molecule.

5. The isolated nucleic acid of claim 1, further defined as including a detectable label.

6. A recombinant vector containing the nucleic acid of claim 1.

7. The recombinant vector of claim 6, further defined as an expression vector comprising a promoter operatively linked to said nucleic acid.

8. A recombinant host cell comprising the recombinant vector of claim 6.

9. The recombinant host cell of claim 8, wherein the host cell is a prokaryotic cell.

10. The recombinant host cell of claim 8, wherein the host cell is a eukaryotic cell.

11. The recombinant host of claim 8, further defined as a *Saccharomyces cerevisiae*, or *Escherichia coli* cell.

12. The recombinant vector of claim 6, further defined as a *Baculovirus* or *Vaccinia* virus vector.

13. A transformed host cell that contains the vector of claim 6.

14. The isolated nucleic acid of claim 1, prepared by a process comprising the steps of:

obtaining a volume of animal cells susceptible to infection by HIV;

preparing a nuclear extract from the animal cells;

chromatographing the nuclear extract on heparin agarose;

eluting the chromatographed nuclear extract with an eluting buffer to obtain fractions having TAR binding activity;

preparing a dialysate of the fractions having TAR binding activity;

chromatographing the dialysate on an anionic separation gel;

precipitating TAR active binding fractions from the anionic separation gel with a precipitating buffer;

applying the TAR active binding fractions to a molecular weight separation column;

collecting TAR active binding fractions and applying a dialysate thereof to a molecular weight separation column;

collecting TAR active binding fractions and applying a dialysate thereof to an anionic separation column;

collecting TAR active binding fractions and applying a dialysate of selected washed fractions to a continuous sucrose gradient;

isolating a cellular protein TRP-185 having a molecular weight of between 175 kD–190 kD as determined by the continuous sucrose gradient;

preparing peptide fragments of said TRP-185 protein;

isolating said peptide fragments;

sequencing said peptide fragments;

designing oligonucleotides that encode a sequence derived from said peptide fragments;

screening a DNA library with said oligonucleotides; and obtaining the isolated nucleic acid of claim 1.

15. A method of preparing recombinant TRP-185 protein encoded by the purified nucleic acid molecule of claim 1, comprising:

preparing a recombinant host bearing a nucleic acid sequence encoding a cellular TRP-185 protein capable of binding a TAR RNA and capable of expressing the protein;

culturing the recombinant host to produce TRP-185; and separating the TRP-185 encoded by the nucleic acid of claim 1 from the recombinant host.

16. The method of claim 15 wherein the recombinant TRP-185 protein is encoded by a nucleic acid having a sequence of SEQ ID NO:1.

17. A method of preparing TRP-185 protein encoded by the purified nucleic acid of claim 1, comprising:

preparing a recombinant host bearing a recombinant DNA segment encoding a cellular TRP-185 protein capable of binding a TAR RNA and capable of expressing the protein;

culturing the recombinant host to produce TRP-185; and separating the TRP-185 encoded by the nucleic acid molecule of claim 1 from the recombinant host.

18. An isolated nucleic acid free of genomic DNA having at least 50 nucleotides corresponding to the coding region of the nucleic acid sequence as set forth in SEQ ID NO:1.

19. The nucleic acid of claim 18, further defined as having at least 100 nucleotides.

20. The nucleic acid of claim 19, further defined as having at least 200 nucleotides.

21. The nucleic acid of claim 20, further defined as having at least 500 nucleotides.

22. The nucleic acid of claim 21, further defined as having at least 1,000 nucleotides.

23. The nucleic acid of claim 22, further defined as having at least 3000 nucleotides.

24. The nucleic acid of claim 21, further defined as having a nucleic acid sequence encoding the coding region of the amino acid sequence of SEQ ID NO:1.

25. The nucleic acid of claim 24, further defined as having a nucleic acid sequence encoding the coding region of the nucleic acid sequence of SEQ ID NO:1.

26. The nucleic acid of claim 25, further defined as having a nucleic acid sequence of SEQ ID NO:1.

27. The nucleic acid of claim 25, further defined as comprising a sequence of SEQ ID NO.5, SEQ ID NO:6, SEQ ID NO:7, SEQ ID NO:8, or SEQ ID NO:9.

28. A nucleic acid having a sequence encoding an amino acid sequence of SEQ ID NO:2, said nucleic acid obtained by a process of:

isolating a cellular protein TRP-185 from animal cells susceptible to infection by HIV, said protein having a molecular weight of between 175 kD–190 kD and having binding activity for TAR as determined by continuous sucrose gradient;

determining amino acid sequences of peptide fragments of said TRP-185 protein;

preparing oligonucleotides that encode a sequence of said peptide fragments;

screening an animal cell DNA library with said oligonucleotides; and obtaining a nucleic acid having a sequence encoding the amino acid sequence of SEQ. ID NO:2.

29. The nucleic acid of claim 25 wherein the animal cells are HeLa, Jurkat, COS, VERO, W138, 293 or a CEM cell line.

30. The nucleic acid of claim 28 wherein the process provides a yield of cellular protein TRP-185 of between 10–15%.

31. The nucleic acid of claim 28 wherein the cellular protein TRP-185 has a molecular weight of about 185 kD.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 5173 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..4863

( x i ) SEQUENCE DESCRIPTION: SEQ ID NO:1:

```
ATG GAG TGG GTG CTC GCG GAA GCG CTG CTC TCG CAG AGC CGG GAC CCC      48
Met Glu Trp Val Leu Ala Glu Ala Leu Leu Ser Gln Ser Arg Asp Pro
 1               5                  10                  15

CGG GCC CTG CTT GGG GCG CTG TGC CAA GGG GAG GCA TCC GCG GAG CGC      96
Arg Ala Leu Leu Gly Ala Leu Cys Gln Gly Glu Ala Ser Ala Glu Arg
             20                  25                  30

GTG GAG ACG CTG CGC TTC CTT CTG CAG CGG CTC GAG GAC GAG GAG GCG     144
Val Glu Thr Leu Arg Phe Leu Leu Gln Arg Leu Glu Asp Glu Glu Ala
         35                  40                  45

CGC GGC AGC GGG GGC GCA GGC GCG CTC CCG GAG GCG GCG CGC GAG GTG     192
Arg Gly Ser Gly Gly Ala Gly Ala Leu Pro Glu Ala Ala Arg Glu Val
     50                  55                  60

GCT GCA GGG TAC CTC GTG CCA CTG CTC CGG AGC CTG CGC GGA CGC CCC     240
Ala Ala Gly Tyr Leu Val Pro Leu Leu Arg Ser Leu Arg Gly Arg Pro
 65                  70                  75                  80

GCG GGC GGC CCG GAC CCC AGT CTG CAG CCT CGC CAC CGC GGC GCG GTG     288
Ala Gly Gly Pro Asp Pro Ser Leu Gln Pro Arg His Arg Arg Arg Val
                 85                  90                  95

CTG AGG GCG GCG GGC GCG GCC CTG CGC TCG TGC GTC CGC CTG GCC GGG     336
Leu Arg Ala Ala Gly Ala Ala Leu Arg Ser Cys Val Arg Leu Ala Gly
             100                 105                 110

CGT CCG CAG CTG GCG GCC GCG CTG GCT GAG GAG GCG CTG CGC GAT CTG     384
Arg Pro Gln Leu Ala Ala Ala Leu Ala Glu Glu Ala Leu Arg Asp Leu
         115                 120                 125

CTC GCC GGG TGG CGC GCG CCT GGC GCC GAG GCT GCC GTG GAA GTG CTA     432
Leu Ala Gly Trp Arg Ala Pro Gly Ala Glu Ala Ala Val Glu Val Leu
     130                 135                 140

GCA GCC GTC GGG CCA TGT TTG CGG CCC CGC GAG GAC GGG CCG CTA CTG     480
Ala Ala Val Gly Pro Cys Leu Arg Pro Arg Glu Asp Gly Pro Leu Leu
145                 150                 155                 160

GAG CGG GTG GCG GGG ACC GCC GTC GCC CTG GCG CTG GGC GGG GGC GGG     528
Glu Arg Val Ala Gly Thr Ala Val Ala Leu Ala Leu Gly Gly Gly Gly
                165                 170                 175

GAC GGG GAT GAG GCC GGG CCT GCC GAG GAC GCG GCG GCG CTG GTG GCC     576
Asp Gly Asp Glu Ala Gly Pro Ala Glu Asp Ala Ala Ala Leu Val Ala
             180                 185                 190

GGG CGA CTG CTG CCA GTG CTG GTC CAA TGT GGC GGG GCG GCG CTG CGG     624
Gly Arg Leu Leu Pro Val Leu Val Gln Cys Gly Gly Ala Ala Leu Arg
         195                 200                 205

GCC GTG TGG GGC GGG CTG GCC GCG CCT GGG GCG TCC CTG GGG TCC GGC     672
Ala Val Trp Gly Gly Leu Ala Ala Pro Gly Ala Ser Leu Gly Ser Gly
     210                 215                 220

CGC GTA GAG GAG AAG CTG CTG GTC CTG AGC GCC CTG GCC GAG AAG CTG     720
Arg Val Glu Glu Lys Leu Leu Val Leu Ser Ala Leu Ala Glu Lys Leu
225                 230                 235                 240

TTG CCC GAG CCC GGC GGC GAC CGC GCC CGC GGC GCG CGC GAG GCG GGC     768
Leu Pro Glu Pro Gly Gly Asp Arg Ala Arg Gly Ala Arg Glu Ala Gly
                245                 250                 255

CCG GAC GCC CGG CGC TGC TGG CGC TTC TGG AGG ACG GTG CAG GCG GGG     816
Pro Asp Ala Arg Arg Cys Trp Arg Phe Trp Arg Thr Val Gln Ala Gly
             260                 265                 270

CTG GGC CAG GCG GAC GCC CTG ACG CGC AAG CGA GCG CGC TAC CTG CTG     864
Leu Gly Gln Ala Asp Ala Leu Thr Arg Lys Arg Ala Arg Tyr Leu Leu
         275                 280                 285

CAG AGG GCG GTG GAG GTG TCG GCG GAG CTG GGG GCC GAC TGC ACC TGC     912
Gln Arg Ala Val Glu Val Ser Ala Glu Leu Gly Ala Asp Cys Thr Cys
     290                 295                 300

GGG CCC CAG GAA GGA AAC GGC CCA AGT CTG TTT TGG TGG TCT GAG AGG     960
Gly Pro Gln Glu Gly Asn Gly Pro Ser Leu Phe Trp Trp Ser Glu Arg
305                 310                 315                 320
```

```
AAA AAA GAT GAG CTT CTA AAG TTT TGG GAA AAT TAT ATT TTA ATT ATG    1008
Lys Lys Asp Glu Leu Leu Lys Phe Trp Glu Asn Tyr Ile Leu Ile Met
            325                 330                 335

GAG ACT TTA GAA GGA AAT CAG ATA CAT GTT ATA AAG CCA GTT TTA CCA    1056
Glu Thr Leu Glu Gly Asn Gln Ile His Val Ile Lys Pro Val Leu Pro
        340                 345                 350

AAG CTA AAC AAT CTG TTT GAA TAT GCG GTG TCA GAG GAA AAT GGA TGT    1104
Lys Leu Asn Asn Leu Phe Glu Tyr Ala Val Ser Glu Glu Asn Gly Cys
            355                 360                 365

TGG CTC TTT CAC CCA TCC TGG CAT ATG TGT ATT TAT AAA AGA ATG TTT    1152
Trp Leu Phe His Pro Ser Trp His Met Cys Ile Tyr Lys Arg Met Phe
        370                 375                 380

GAA AGT GAA AAC AAA ATC CTG TCC AAA GAA GGT GTT ATC CAT TTT TTG    1200
Glu Ser Glu Asn Lys Ile Leu Ser Lys Glu Gly Val Ile His Phe Leu
385                 390                 395                 400

GAG CTG TAT GAA ACA AAG ATT CTT CCA TTT TCA CCA GAA TTT TCT GAG    1248
Glu Leu Tyr Glu Thr Lys Ile Leu Pro Phe Ser Pro Glu Phe Ser Glu
        405                 410                 415

TTT ATT ATT GGA CCA TTA ATG GAT GCG CTT TCA GAG AGC TCT CTG TAT    1296
Phe Ile Ile Gly Pro Leu Met Asp Ala Leu Ser Glu Ser Ser Leu Tyr
            420                 425                 430

AGC AGG TCC CCA GGC CAG CCA ATA GGA AGC TGT TCT CCA TTG GGA CTG    1344
Ser Arg Ser Pro Gly Gln Pro Ile Gly Ser Cys Ser Pro Leu Gly Leu
        435                 440                 445

AAA TTA CAG AAG TTT TTA GTC ACT TAT ATT TCT CTT CTT CCA GAA GAA    1392
Lys Leu Gln Lys Phe Leu Val Thr Tyr Ile Ser Leu Leu Pro Glu Glu
    450                 455                 460

ATA AAG AGT AGC TTC CTA TTG AAG TTT ATT CGG AAG ATG ACA AGT AGG    1440
Ile Lys Ser Ser Phe Leu Leu Lys Phe Ile Arg Lys Met Thr Ser Arg
465                 470                 475                 480

CAT TGG TGT GCT GTT CCC ATT TTG TTT CTA TCT AAG GCT TTG GCA AAT    1488
His Trp Cys Ala Val Pro Ile Leu Phe Leu Ser Lys Ala Leu Ala Asn
            485                 490                 495

GTC CCA AGA CAT AAG GCC CTG GGT ATA GAT GGG CTT CTT GCT CTC AGG    1536
Val Pro Arg His Lys Ala Leu Gly Ile Asp Gly Leu Leu Ala Leu Arg
        500                 505                 510

GAT GTT ATT CAT TGC ACT ATG ATC ACA CAT CAG ATT CTC CTG AGA GGG    1584
Asp Val Ile His Cys Thr Met Ile Thr His Gln Ile Leu Leu Arg Gly
            515                 520                 525

GCA GCC CAA TGC TAC CTT CTT CAA ACA GCT ATG AAT TTG CTA GAT GTG    1632
Ala Ala Gln Cys Tyr Leu Leu Gln Thr Ala Met Asn Leu Leu Asp Val
        530                 535                 540

GAG AAA GTG TCA CTT TCT GAT GTC TCA ACT TTT CTC ATG TCT CTG AGA    1680
Glu Lys Val Ser Leu Ser Asp Val Ser Thr Phe Leu Met Ser Leu Arg
545                 550                 555                 560

CAA GAG GAA TCC TTA GGA CGA GGA ACT TCA TTG TGG ACA GAG CTG TGT    1728
Gln Glu Glu Ser Leu Gly Arg Gly Thr Ser Leu Trp Thr Glu Leu Cys
            565                 570                 575

GAC TGG CTA CGT GTT AAT GAA AGC TAT TTT AAG CCA TCC CCT ACG TGT    1776
Asp Trp Leu Arg Val Asn Glu Ser Tyr Phe Lys Pro Ser Pro Thr Cys
        580                 585                 590

AGC TCC ATT GGA CTT CAC AAG ACA TCT TTA AAT GCT TAT GTA AAG AGC    1824
Ser Ser Ile Gly Leu His Lys Thr Ser Leu Asn Ala Tyr Val Lys Ser
            595                 600                 605

ATT GTT CAA GAG TAT GTT AAG TCA TCT GCT TGG GAA ACA GGA GAA AAC    1872
Ile Val Gln Glu Tyr Val Lys Ser Ser Ala Trp Glu Thr Gly Glu Asn
        610                 615                 620

TGC TTT ATG CCT GAT TGG TTT GAA GCC AAG CTT GTT TCT CTG ATG GTC    1920
Cys Phe Met Pro Asp Trp Phe Glu Ala Lys Leu Val Ser Leu Met Val
625                 630                 635                 640
```

-continued

| | | | | | | | | | | | | | | | | |
|---|---|---|---|---|---|---|---|---|---|---|---|---|---|---|---|---|
| TTG | CTG | GCT | GTG | GAT | GTG | GAA | GGA | ATG | AAG | ACT | CAG | TAT | AGC | GGA | AAG | 1968 |
| Leu | Leu | Ala | Val | Asp | Val | Glu | Gly | Met | Lys | Thr | Gln | Tyr | Ser | Gly | Lys | |
| | | | | 645 | | | | 650 | | | | | | | 655 | |
| CAG | AGA | ACA | GAG | AAT | GTA | TTG | CGG | ATA | TTC | TTA | GAC | CCT | CTT | CTG | GAT | 2016 |
| Gln | Arg | Thr | Glu | Asn | Val | Leu | Arg | Ile | Phe | Leu | Asp | Pro | Leu | Leu | Asp | |
| | | | 660 | | | | | 665 | | | | | | 670 | | |
| GTG | CTT | ATG | AAG | TTT | AGT | ACC | AAT | GCC | TAC | ATG | CCC | TTG | CTG | AAG | ACT | 2064 |
| Val | Leu | Met | Lys | Phe | Ser | Thr | Asn | Ala | Tyr | Met | Pro | Leu | Leu | Lys | Thr | |
| | | 675 | | | | | 680 | | | | | 685 | | | | |
| GAC | AGA | TGC | CTC | CAG | CTG | CTG | TTG | AAG | CTG | TTG | AAC | ACA | TGC | AGG | TTG | 2112 |
| Asp | Arg | Cys | Leu | Gln | Leu | Leu | Leu | Lys | Leu | Leu | Asn | Thr | Cys | Arg | Leu | |
| | 690 | | | | | 695 | | | | | 700 | | | | | |
| AAA | GGT | TCC | AGT | GCC | CAA | GAT | GAT | GAG | GTG | TCT | ACT | GTT | CTT | CAG | AAC | 2160 |
| Lys | Gly | Ser | Ser | Ala | Gln | Asp | Asp | Glu | Val | Ser | Thr | Val | Leu | Gln | Asn | |
| 705 | | | | | 710 | | | | | 715 | | | | | 720 | |
| TTT | TTC | ATG | TCT | ACT | ACA | GAG | AGC | ATT | TCT | GAA | TTT | ATT | CTC | AGA | AGA | 2208 |
| Phe | Phe | Met | Ser | Thr | Thr | Glu | Ser | Ile | Ser | Glu | Phe | Ile | Leu | Arg | Arg | |
| | | | | 725 | | | | | 730 | | | | | 735 | | |
| CTT | ACT | ATG | AAT | GAG | CTA | AAT | AGT | GTT | TCA | GAT | CTG | GAT | CGT | TGC | CAT | 2256 |
| Leu | Thr | Met | Asn | Glu | Leu | Asn | Ser | Val | Ser | Asp | Leu | Asp | Arg | Cys | His | |
| | | | | 740 | | | | | 745 | | | | | 750 | | |
| TTA | TAC | CTG | ATG | GTG | TTA | ACT | GAG | CTT | ATA | AAT | CTG | CAT | TTG | AAG | GTT | 2304 |
| Leu | Tyr | Leu | Met | Val | Leu | Thr | Glu | Leu | Ile | Asn | Leu | His | Leu | Lys | Val | |
| | | 755 | | | | | 760 | | | | | 765 | | | | |
| GGG | TGG | AAA | AGG | GGT | AAC | CCT | ATC | TGG | AGA | GTT | ATT | TCT | CTT | TTG | AAA | 2352 |
| Gly | Trp | Lys | Arg | Gly | Asn | Pro | Ile | Trp | Arg | Val | Ile | Ser | Leu | Leu | Lys | |
| | 770 | | | | | 775 | | | | | 780 | | | | | |
| AAT | GCA | TCC | ATT | CAG | CAT | CTT | CAA | GAG | ATG | GAC | AGT | GGA | CAG | GAG | CCA | 2400 |
| Asn | Ala | Ser | Ile | Gln | His | Leu | Gln | Glu | Met | Asp | Ser | Gly | Gln | Glu | Pro | |
| 785 | | | | | 790 | | | | | 795 | | | | | 800 | |
| ACA | GTT | GGA | AGT | CAG | ATT | CAG | AGA | GTA | GTG | AGC | ATG | GCT | GCC | TTG | GCC | 2448 |
| Thr | Val | Gly | Ser | Gln | Ile | Gln | Arg | Val | Val | Ser | Met | Ala | Ala | Leu | Ala | |
| | | | | 805 | | | | | 810 | | | | | 815 | | |
| ATG | GTG | TGT | GAG | GCC | ATA | GAC | CAG | AAG | CCT | GAG | CTG | CAG | CTG | GAC | TCT | 2496 |
| Met | Val | Cys | Glu | Ala | Ile | Asp | Gln | Lys | Pro | Glu | Leu | Gln | Leu | Asp | Ser | |
| | | | 820 | | | | | 825 | | | | | 830 | | | |
| CTC | CAT | GCT | GGG | CCC | CTG | GAA | AGC | TTC | CTT | TCC | TCT | CTT | CAG | CTC | AAT | 2544 |
| Leu | His | Ala | Gly | Pro | Leu | Glu | Ser | Phe | Leu | Ser | Ser | Leu | Gln | Leu | Asn | |
| | | 835 | | | | | 840 | | | | | 845 | | | | |
| CAG | ACG | CTG | CAG | AAG | CCC | CAC | GCA | GAG | GAG | CAG | AGC | AGT | TAT | GCT | CAC | 2592 |
| Gln | Thr | Leu | Gln | Lys | Pro | His | Ala | Glu | Glu | Gln | Ser | Ser | Tyr | Ala | His | |
| | 850 | | | | | 855 | | | | | 860 | | | | | |
| CCC | TTG | GAG | TGC | AGC | AGT | GTT | TTG | GAA | GAA | TCG | TCA | TCT | TCC | CAA | GGA | 2640 |
| Pro | Leu | Glu | Cys | Ser | Ser | Val | Leu | Glu | Glu | Ser | Ser | Ser | Ser | Gln | Gly | |
| 865 | | | | | 870 | | | | | 875 | | | | | 880 | |
| TGG | GGA | AAA | ATA | GTT | GCA | CAA | TAT | ATT | CAT | GAT | CAA | TGG | GTG | TGC | CTC | 2688 |
| Trp | Gly | Lys | Ile | Val | Ala | Gln | Tyr | Ile | His | Asp | Gln | Trp | Val | Cys | Leu | |
| | | | | 885 | | | | | 890 | | | | | 895 | | |
| TCT | TTC | CTG | TTG | AAA | AAA | TAT | CAC | ACC | CTT | ATA | CCA | ACC | ACA | GGG | AGT | 2736 |
| Ser | Phe | Leu | Leu | Lys | Lys | Tyr | His | Thr | Leu | Ile | Pro | Thr | Thr | Gly | Ser | |
| | | | 900 | | | | | 905 | | | | | 910 | | | |
| GAA | ATT | CTG | GAA | CCG | TTT | CTA | CCT | GCC | GTT | CAG | ATG | CCA | ATA | AGG | ACT | 2784 |
| Glu | Ile | Leu | Glu | Pro | Phe | Leu | Pro | Ala | Val | Gln | Met | Pro | Ile | Arg | Thr | |
| | | 915 | | | | | 920 | | | | | 925 | | | | |
| TTG | CAG | TCT | GCA | CTA | GAA | GCC | CTC | ACA | GTT | CTT | TCT | TCT | GAT | CAA | GTT | 2832 |
| Leu | Gln | Ser | Ala | Leu | Glu | Ala | Leu | Thr | Val | Leu | Ser | Ser | Asp | Gln | Val | |
| | 930 | | | | | 935 | | | | | 940 | | | | | |
| TTA | CCA | GTG | TTC | CAT | TGC | TTG | AAA | GTG | TTG | GTT | CCC | AAG | CTT | CTG | ACT | 2880 |
| Leu | Pro | Val | Phe | His | Cys | Leu | Lys | Val | Leu | Val | Pro | Lys | Leu | Leu | Thr | |
| 945 | | | | | 950 | | | | | 955 | | | | | 960 | |

-continued

| | | | | | | | | | | | | | | | | |
|---|---|---|---|---|---|---|---|---|---|---|---|---|---|---|---|---|
| TCC | TCT | GAA | TCA | CTC | TGC | ATA | GAG | TCT | TTT | GAC | ATG | GCG | TGG | AAA | ATT | 2928 |
| Ser | Ser | Glu | Ser | Leu | Cys | Ile | Glu | Ser | Phe | Asp | Met | Ala | Trp | Lys | Ile | |
| | | | | 965 | | | | 970 | | | | | 975 | | | |
| ATA | TCT | TCT | TTA | AGC | AAC | ACT | CAG | CTG | ATA | TTC | TGG | GCT | AAT | TTA | AAA | 2976 |
| Ile | Ser | Ser | Leu | Ser | Asn | Thr | Gln | Leu | Ile | Phe | Trp | Ala | Asn | Leu | Lys | |
| | | | 980 | | | | | 985 | | | | | 990 | | | |
| GCT | TTT | GTT | CAG | TTT | GTT | TTT | GAT | AAC | AAA | GTT | CTT | ACC | ATT | GCT | GCC | 3024 |
| Ala | Phe | Val | Gln | Phe | Val | Phe | Asp | Asn | Lys | Val | Leu | Thr | Ile | Ala | Ala | |
| | | 995 | | | | | 1000 | | | | | 1005 | | | | |
| AAA | ATC | AAG | GGC | CAG | GCA | TAT | TTC | AAA | ATA | AAA | GAG | ATT | ATG | TAC | AAG | 3072 |
| Lys | Ile | Lys | Gly | Gln | Ala | Tyr | Phe | Lys | Ile | Lys | Glu | Ile | Met | Tyr | Lys | |
| | | 1010 | | | | | 1015 | | | | | 1020 | | | | |
| ATA | ATT | GAA | ATG | TCT | GCT | ATA | AAG | ACT | GGA | GTC | TTC | AAT | ACA | CTG | ATA | 3120 |
| Ile | Ile | Glu | Met | Ser | Ala | Ile | Lys | Thr | Gly | Val | Phe | Asn | Thr | Leu | Ile | |
| 1025 | | | | 1030 | | | | | 1035 | | | | | 1040 | | |
| AGT | TAC | TGC | TGT | CAG | TCT | TGG | ATA | GTG | TCT | GCT | TCA | AAT | GTG | TCC | CAA | 3168 |
| Ser | Tyr | Cys | Cys | Gln | Ser | Trp | Ile | Val | Ser | Ala | Ser | Asn | Val | Ser | Gln | |
| | | | 1045 | | | | | 1050 | | | | | 1055 | | | |
| GGA | TCT | TTA | TCA | AGT | GCT | AAA | AAT | TAT | AGC | GAA | CTT | ATC | CTT | GAG | GCT | 3216 |
| Gly | Ser | Leu | Ser | Ser | Ala | Lys | Asn | Tyr | Ser | Glu | Leu | Ile | Leu | Glu | Ala | |
| | | | 1060 | | | | | 1065 | | | | | 1070 | | | |
| TGT | ATA | TTT | GGA | ACT | GTG | TTT | AGG | CGT | GAT | CAA | AGA | CTT | GTT | CAG | GAT | 3264 |
| Cys | Ile | Phe | Gly | Thr | Val | Phe | Arg | Arg | Asp | Gln | Arg | Leu | Val | Gln | Asp | |
| | | | 1075 | | | | | 1080 | | | | | 1085 | | | |
| GTA | CAG | ACC | TTC | ATA | GAA | AAC | TTG | GGA | CAT | GAC | TGT | GCG | GCA | AAT | ATT | 3312 |
| Val | Gln | Thr | Phe | Ile | Glu | Asn | Leu | Gly | His | Asp | Cys | Ala | Ala | Asn | Ile | |
| | | 1090 | | | | | 1095 | | | | | 1100 | | | | |
| GTT | ATG | GAA | AAT | ACT | AAG | AGA | GAA | GAC | CAT | TAT | GTG | AGA | ATT | TGT | GCT | 3360 |
| Val | Met | Glu | Asn | Thr | Lys | Arg | Glu | Asp | His | Tyr | Val | Arg | Ile | Cys | Ala | |
| 1105 | | | | 1110 | | | | | 1115 | | | | | 1120 | | |
| GTC | AAA | TTC | CTG | TGT | TTA | TTA | GAT | GGC | TCC | AAT | ATG | TCC | CAC | AAG | TTG | 3408 |
| Val | Lys | Phe | Leu | Cys | Leu | Leu | Asp | Gly | Ser | Asn | Met | Ser | His | Lys | Leu | |
| | | | 1125 | | | | | 1130 | | | | | 1135 | | | |
| TTT | ATT | GAG | GAT | CTT | GCA | ATC | AAG | CTA | TTA | GAT | AAA | GAT | GAA | TTA | GTG | 3456 |
| Phe | Ile | Glu | Asp | Leu | Ala | Ile | Lys | Leu | Leu | Asp | Lys | Asp | Glu | Leu | Val | |
| | | | | 1140 | | | | 1145 | | | | | 1150 | | | |
| TCC | AAG | TCC | AAA | AAA | CGC | TAC | TAT | GTG | AAT | TCT | CTA | CAG | CAC | AGA | GTG | 3504 |
| Ser | Lys | Ser | Lys | Lys | Arg | Tyr | Tyr | Val | Asn | Ser | Leu | Gln | His | Arg | Val | |
| | | | 1155 | | | | | 1160 | | | | | 1165 | | | |
| AAA | AAC | CGA | GTC | TGG | CAG | ACT | CTG | CTG | GTA | CTT | TTC | CCT | AGA | CTT | GAC | 3552 |
| Lys | Asn | Arg | Val | Trp | Gln | Thr | Leu | Leu | Val | Leu | Phe | Pro | Arg | Leu | Asp | |
| | 1170 | | | | | 1175 | | | | | 1180 | | | | | |
| CAG | AAT | TTC | TTG | AAT | GGA | ATT | ATT | GAC | AGG | ATT | TTC | CAG | GCT | GGT | TTC | 3600 |
| Gln | Asn | Phe | Leu | Asn | Gly | Ile | Ile | Asp | Arg | Ile | Phe | Gln | Ala | Gly | Phe | |
| 1185 | | | | 1190 | | | | | 1195 | | | | | 1200 | | |
| ACC | AAC | AAT | CAA | GCA | TCC | ATA | AAA | TAT | TTT | ATA | GAA | TGG | ATT | ATT | ATA | 3648 |
| Thr | Asn | Asn | Gln | Ala | Ser | Ile | Lys | Tyr | Phe | Ile | Glu | Trp | Ile | Ile | Ile | |
| | | | | 1205 | | | | 1210 | | | | | 1215 | | | |
| TTG | ATT | CTT | CAT | AAA | TTC | CCT | CAA | TTT | CTT | CCA | AAG | TTC | TGG | GAT | TGT | 3696 |
| Leu | Ile | Leu | His | Lys | Phe | Pro | Gln | Phe | Leu | Pro | Lys | Phe | Trp | Asp | Cys | |
| | | | 1220 | | | | 1225 | | | | | 1230 | | | | |
| TTT | TCT | TAT | GGT | GAA | GAA | AAT | CTT | AAA | ACA | AGC | ATT | TGT | ACA | TTT | TTA | 3744 |
| Phe | Ser | Tyr | Gly | Glu | Glu | Asn | Leu | Lys | Thr | Ser | Ile | Cys | Thr | Phe | Leu | |
| | | | 1235 | | | | | 1240 | | | | | 1245 | | | |
| GCA | GTT | TTA | TCA | CAT | TTA | GAC | ATT | ATT | ACT | CAA | AAT | ATT | CCA | GAA | AAG | 3792 |
| Ala | Val | Leu | Ser | His | Leu | Asp | Ile | Ile | Thr | Gln | Asn | Ile | Pro | Glu | Lys | |
| | | 1250 | | | | | 1255 | | | | | 1260 | | | | |
| AAA | CTA | ATT | CTG | AAG | CAA | GCC | CTT | ATA | GTT | GTG | CTG | CAG | TGG | TGT | TTC | 3840 |
| Lys | Leu | Ile | Leu | Lys | Gln | Ala | Leu | Ile | Val | Val | Leu | Gln | Trp | Cys | Phe | |
| 1265 | | | | 1270 | | | | | 1275 | | | | | 1280 | | |

| | | | | | | | | | | | | | | | | |
|---|---|---|---|---|---|---|---|---|---|---|---|---|---|---|---|---|
| AAT | CAC | AAT | TTT | AGT | GTT | CGA | CTG | TAT | GCT | TTA | GTT | GCT | CTT | AAG | AAA | 3888 |
| Asn | His | Asn | Phe | Ser | Val | Arg | Leu | Tyr | Ala | Leu | Val | Ala | Leu | Lys | Lys | |
| | | | | 1285 | | | | | 1290 | | | | | 1295 | | |
| CTC | TGG | ACT | GTG | TGT | AAA | GTG | TTA | AGT | GTT | GAA | GAA | TTT | GAT | GCC | CTG | 3936 |
| Leu | Trp | Thr | Val | Cys | Lys | Val | Leu | Ser | Val | Glu | Glu | Phe | Asp | Ala | Leu | |
| | | | 1300 | | | | | 1305 | | | | | 1310 | | | |
| ACT | CCT | GTG | ATT | GAA | TCC | AGC | CTC | CAT | CAA | GTG | GAA | AGC | ATG | CAC | GGA | 3984 |
| Thr | Pro | Val | Ile | Glu | Ser | Ser | Leu | His | Gln | Val | Glu | Ser | Met | His | Gly | |
| | | | 1315 | | | | | 1320 | | | | | 1325 | | | |
| GCA | GGG | AAT | GCC | AAG | AAG | AAT | TGG | CAA | CGC | ATT | CAG | GAG | CAT | TTC | TTT | 4032 |
| Ala | Gly | Asn | Ala | Lys | Lys | Asn | Trp | Gln | Arg | Ile | Gln | Glu | His | Phe | Phe | |
| | | | 1330 | | | | | 1335 | | | | | 1340 | | | |
| TTT | GCA | ACA | TTT | CAC | CCA | CTC | AAG | GAT | TAT | TGT | CTA | GAG | ACC | ATA | TTT | 4080 |
| Phe | Ala | Thr | Phe | His | Pro | Leu | Lys | Asp | Tyr | Cys | Leu | Glu | Thr | Ile | Phe | |
| 1345 | | | | | 1350 | | | | | 1355 | | | | | 1360 | |
| TAC | ATC | CTT | CCA | CGC | CTT | TCA | GGC | CTT | ATT | GAA | GAT | GAA | TGG | ATC | ACC | 4128 |
| Tyr | Ile | Leu | Pro | Arg | Leu | Ser | Gly | Leu | Ile | Glu | Asp | Glu | Trp | Ile | Thr | |
| | | | | 1365 | | | | | 1370 | | | | | 1375 | | |
| ATT | GAT | AAA | TTT | ACC | AGA | TTC | ACT | GAT | GTT | CCT | TTA | GCT | GCG | GGA | TTT | 4176 |
| Ile | Asp | Lys | Phe | Thr | Arg | Phe | Thr | Asp | Val | Pro | Leu | Ala | Ala | Gly | Phe | |
| | | | 1380 | | | | | 1385 | | | | | 1390 | | | |
| CAG | TGG | TAC | CTT | TCT | CAA | ACT | CAA | CTT | AGT | AAA | CTA | AAA | CCA | GGT | GAC | 4224 |
| Gln | Trp | Tyr | Leu | Ser | Gln | Thr | Gln | Leu | Ser | Lys | Leu | Lys | Pro | Gly | Asp | |
| | | | 1395 | | | | | 1400 | | | | | 1405 | | | |
| TGG | TCT | CAG | CAA | GAC | ATA | GGT | ACT | AAT | TTG | GTT | GAA | GCA | GAT | AAC | CAA | 4272 |
| Trp | Ser | Gln | Gln | Asp | Ile | Gly | Thr | Asn | Leu | Val | Glu | Ala | Asp | Asn | Gln | |
| | | | 1410 | | | | | 1415 | | | | | 1420 | | | |
| GCA | GAG | TGG | ACC | GAC | GTT | CAG | AAG | AAG | ATT | ATC | CCG | TGG | AAC | AGT | CGT | 4320 |
| Ala | Glu | Trp | Thr | Asp | Val | Gln | Lys | Lys | Ile | Ile | Pro | Trp | Asn | Ser | Arg | |
| 1425 | | | | | 1430 | | | | | 1435 | | | | | 1440 | |
| GTT | TCC | GAC | TTA | GAC | CTG | GAG | CTC | CTG | TTT | CAG | GAT | CGT | GCT | GCC | AGA | 4368 |
| Val | Ser | Asp | Leu | Asp | Leu | Glu | Leu | Leu | Phe | Gln | Asp | Arg | Ala | Ala | Arg | |
| | | | | 1445 | | | | | 1450 | | | | | 1455 | | |
| CTT | GGA | AAG | TCA | ATT | AGT | AGA | CTC | ATC | GTT | GTG | GCC | TCG | CTC | ATC | GAC | 4416 |
| Leu | Gly | Lys | Ser | Ile | Ser | Arg | Leu | Ile | Val | Val | Ala | Ser | Leu | Ile | Asp | |
| | | | 1460 | | | | | 1465 | | | | | 1470 | | | |
| AAA | CCG | ACC | AAT | TTA | GGA | GGA | CTG | TGC | AGG | ACC | TGT | GAG | GTA | TTT | GGG | 4464 |
| Lys | Pro | Thr | Asn | Leu | Gly | Gly | Leu | Cys | Arg | Thr | Cys | Glu | Val | Phe | Gly | |
| Lys | Pro | Thr | Asn | Leu | Gly | Gly | Leu | Cys | Arg | Thr | Cys | Glu | Val | Phe | Gly | |
| | | | 1475 | | | | | 1480 | | | | | 1485 | | | |
| GCT | TCA | GTG | CTC | GTT | GTT | GGC | AGC | CTT | CAG | TGT | ATC | AGC | GAC | AAA | CAG | 4512 |
| Ala | Ser | Val | Leu | Val | Val | Gly | Ser | Leu | Gln | Cys | Ile | Ser | Asp | Lys | Gln | |
| | | | 1490 | | | | | 1495 | | | | | 1500 | | | |
| TTT | CAG | CAC | CTC | AGT | GTC | TCT | GCA | GAA | CAG | TGG | CTT | CCT | CTA | GTG | GAG | 4560 |
| Phe | Gln | His | Leu | Ser | Val | Ser | Ala | Glu | Gln | Trp | Leu | Pro | Leu | Val | Glu | |
| 1505 | | | | | 1510 | | | | | 1515 | | | | | 1520 | |
| GTA | AAA | CCA | CCT | CAG | CTA | ATT | GAT | TAT | CTG | CAG | CAG | AAG | AAA | ACA | GAA | 4608 |
| Val | Lys | Pro | Pro | Gln | Leu | Ile | Asp | Tyr | Leu | Gln | Gln | Lys | Lys | Thr | Glu | |
| | | | | 1525 | | | | | 1530 | | | | | 1535 | | |
| GGT | TAT | ACC | ATC | ATT | GGA | GTG | GAA | CAA | ACT | GCC | AAA | AGT | TTA | GAC | CTA | 4656 |
| Gly | Tyr | Thr | Ile | Ile | Gly | Val | Glu | Gln | Thr | Ala | Lys | Ser | Leu | Asp | Leu | |
| | | | | 1540 | | | | | 1545 | | | | | 1550 | | |
| ACC | CAA | TAT | TGC | TTT | CCT | GAG | AAA | TCT | CTG | CTC | TTG | TTG | GGA | AAT | GAA | 4704 |
| Thr | Gln | Tyr | Cys | Phe | Pro | Glu | Lys | Ser | Leu | Leu | Leu | Leu | Gly | Asn | Glu | |
| | | | | 1555 | | | | | 1560 | | | | | 1565 | | |
| CGT | GAG | GGA | ATT | CCA | GCA | AAT | CTG | ATC | CAA | CAG | TTG | GAC | GTT | TGT | GTG | 4752 |
| Arg | Glu | Gly | Ile | Pro | Ala | Asn | Leu | Ile | Gln | Gln | Leu | Asp | Val | Cys | Val | |
| | | | 1570 | | | | | 1575 | | | | | 1580 | | | |
| GAA | ATT | CCT | CAA | CAG | GGC | ATT | ATC | CGC | TCC | CTG | AAT | GTC | CAT | GTG | AGT | 4800 |
| Glu | Ile | Pro | Gln | Gln | Gly | Ile | Ile | Arg | Ser | Leu | Asn | Val | His | Val | Ser | |
| 1585 | | | | | 1590 | | | | | 1595 | | | | | 1600 | |

```
GGA GCC CTG CTG ATC TGG GAG TAC ACC AGG CAG CAG CTG CTC TCG CAC      4848
Gly Ala Leu Leu Ile Trp Glu Tyr Thr Arg Gln Gln Leu Leu Ser His
              1605                    1610                    1615

GGA GAT ACC AAG CCA TGATGTGCCT TCCTTAGTGA ACTGCTGCTG CTGTTCAGAC       4903
Gly Asp Thr Lys Pro
              1620

TTTTTTAAAA AAAACTATTT GGACTAAAGA AACAGATTCT GAAATTTATT GTGATAATTT     4963

GTATTTCTTT TTTCTTGCAA TTTAATGCCA AAAGTTTGCC ATGTGCCTTA AACATATTAC     5023

TATATATTTT CCCCTTTAAT AAACACTTTT TGTTAAATTG TATTCTTCCT TTAATAAAAT     5083

ATTTTAAGCA ATTGTCCAAT AAAAAAAAAA AAAAAAAAAA AAAAAAAAAA AAAAAAAAA      5143

AAAAAAAAAA AAAAAAAAAA AAAAAAAAA                                       5173
```

( 2 ) INFORMATION FOR SEQ ID NO:2:

( i ) SEQUENCE CHARACTERISTICS:
        ( A ) LENGTH: 1621 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Glu Trp Val Leu Ala Glu Ala Leu Leu Ser Gln Ser Arg Asp Pro
 1               5                  10                  15

Arg Ala Leu Leu Gly Ala Leu Cys Gln Gly Glu Ala Ser Ala Glu Arg
                20                  25                  30

Val Glu Thr Leu Arg Phe Leu Leu Gln Arg Leu Glu Asp Glu Glu Ala
            35                  40                  45

Arg Gly Ser Gly Gly Ala Gly Ala Leu Pro Glu Ala Ala Arg Glu Val
        50                  55                  60

Ala Ala Gly Tyr Leu Val Pro Leu Leu Arg Ser Leu Arg Gly Arg Pro
 65                  70                  75                  80

Ala Gly Gly Pro Asp Pro Ser Leu Gln Pro Arg His Arg Arg Arg Val
                85                  90                  95

Leu Arg Ala Ala Gly Ala Ala Leu Arg Ser Cys Val Arg Leu Ala Gly
                100                 105                 110

Arg Pro Gln Leu Ala Ala Ala Leu Ala Glu Glu Ala Leu Arg Asp Leu
            115                 120                 125

Leu Ala Gly Trp Arg Ala Pro Gly Ala Glu Ala Ala Val Glu Val Leu
        130                 135                 140

Ala Ala Val Gly Pro Cys Leu Arg Pro Arg Glu Asp Gly Pro Leu Leu
145                 150                 155                 160

Glu Arg Val Ala Gly Thr Ala Val Ala Leu Ala Leu Gly Gly Gly Gly
                165                 170                 175

Asp Gly Asp Glu Ala Gly Pro Ala Glu Asp Ala Ala Ala Leu Val Ala
                180                 185                 190

Gly Arg Leu Leu Pro Val Leu Val Gln Cys Gly Gly Ala Ala Leu Arg
            195                 200                 205

Ala Val Trp Gly Gly Leu Ala Ala Pro Gly Ala Ser Leu Gly Ser Gly
        210                 215                 220

Arg Val Glu Glu Lys Leu Leu Val Leu Ser Ala Leu Ala Glu Lys Leu
225                 230                 235                 240

Leu Pro Glu Pro Gly Gly Asp Arg Ala Arg Gly Ala Arg Glu Ala Gly
                245                 250                 255

Pro Asp Ala Arg Arg Cys Trp Arg Phe Trp Arg Thr Val Gln Ala Gly
```

```
              260                         265                         270
Leu  Gly  Gln  Ala  Asp  Ala  Leu  Thr  Arg  Lys  Arg  Ala  Arg  Tyr  Leu  Leu
          275                         280                         285

Gln  Arg  Ala  Val  Glu  Val  Ser  Ala  Glu  Leu  Gly  Ala  Asp  Cys  Thr  Cys
290                          295                         300

Gly  Pro  Gln  Glu  Gly  Asn  Gly  Pro  Ser  Leu  Phe  Trp  Trp  Ser  Glu  Arg
305                          310                         315                         320

Lys  Lys  Asp  Glu  Leu  Leu  Lys  Phe  Trp  Glu  Asn  Tyr  Ile  Leu  Ile  Met
               325                         330                         335

Glu  Thr  Leu  Glu  Gly  Asn  Gln  Ile  His  Val  Ile  Lys  Pro  Val  Leu  Pro
               340                         345                         350

Lys  Leu  Asn  Asn  Leu  Phe  Glu  Tyr  Ala  Val  Ser  Glu  Glu  Asn  Gly  Cys
               355                         360                         365

Trp  Leu  Phe  His  Pro  Ser  Trp  His  Met  Cys  Ile  Tyr  Lys  Arg  Met  Phe
     370                         375                         380

Glu  Ser  Glu  Asn  Lys  Ile  Leu  Ser  Lys  Glu  Gly  Val  Ile  His  Phe  Leu
385                          390                         395                         400

Glu  Leu  Tyr  Glu  Thr  Lys  Ile  Leu  Pro  Phe  Ser  Pro  Glu  Phe  Ser  Glu
                    405                         410                         415

Phe  Ile  Ile  Gly  Pro  Leu  Met  Asp  Ala  Leu  Ser  Glu  Ser  Ser  Leu  Tyr
               420                         425                         430

Ser  Arg  Ser  Pro  Gly  Gln  Pro  Ile  Gly  Ser  Cys  Ser  Pro  Leu  Gly  Leu
          435                         440                         445

Lys  Leu  Gln  Lys  Phe  Leu  Val  Thr  Tyr  Ile  Ser  Leu  Leu  Pro  Glu  Glu
     450                         455                         460

Ile  Lys  Ser  Ser  Phe  Leu  Leu  Lys  Phe  Ile  Arg  Lys  Met  Thr  Ser  Arg
465                          470                         475                         480

His  Trp  Cys  Ala  Val  Pro  Ile  Leu  Phe  Leu  Ser  Lys  Ala  Leu  Ala  Asn
               485                         490                         495

Val  Pro  Arg  His  Lys  Ala  Leu  Gly  Ile  Asp  Gly  Leu  Leu  Ala  Leu  Arg
               500                         505                         510

Asp  Val  Ile  His  Cys  Thr  Met  Ile  Thr  His  Gln  Ile  Leu  Arg  Gly
          515                         520                         525

Ala  Ala  Gln  Cys  Tyr  Leu  Leu  Gln  Thr  Ala  Met  Asn  Leu  Leu  Asp  Val
530                          535                         540

Glu  Lys  Val  Ser  Leu  Ser  Asp  Val  Ser  Thr  Phe  Leu  Met  Ser  Leu  Arg
545                          550                         555                         560

Gln  Glu  Glu  Ser  Leu  Gly  Arg  Gly  Thr  Ser  Leu  Trp  Thr  Glu  Leu  Cys
               565                         570                         575

Asp  Trp  Leu  Arg  Val  Asn  Glu  Ser  Tyr  Phe  Lys  Pro  Ser  Pro  Thr  Cys
          580                         585                         590

Ser  Ser  Ile  Gly  Leu  His  Lys  Thr  Ser  Leu  Asn  Ala  Tyr  Val  Lys  Ser
          595                         600                         605

Ile  Val  Gln  Glu  Tyr  Val  Lys  Ser  Ser  Ala  Trp  Glu  Thr  Gly  Glu  Asn
     610                         615                         620

Cys  Phe  Met  Pro  Asp  Trp  Phe  Glu  Ala  Lys  Leu  Val  Ser  Leu  Met  Val
625                          630                         635                         640

Leu  Leu  Ala  Val  Asp  Val  Glu  Gly  Met  Lys  Thr  Gln  Tyr  Ser  Gly  Lys
               645                         650                         655

Gln  Arg  Thr  Glu  Asn  Val  Leu  Arg  Ile  Phe  Leu  Asp  Pro  Leu  Leu  Asp
               660                         665                         670

Val  Leu  Met  Lys  Phe  Ser  Thr  Asn  Ala  Tyr  Met  Pro  Leu  Leu  Lys  Thr
          675                         680                         685
```

```
Asp Arg Cys Leu Gln Leu Leu Leu Lys Leu Leu Asn Thr Cys Arg Leu
690                     695                 700

Lys Gly Ser Ser Ala Gln Asp Asp Glu Val Ser Thr Val Leu Gln Asn
705                 710                 715                 720

Phe Phe Met Ser Thr Thr Glu Ser Ile Ser Glu Phe Ile Leu Arg Arg
                725                 730                 735

Leu Thr Met Asn Glu Leu Asn Ser Val Ser Asp Leu Asp Arg Cys His
            740                 745                 750

Leu Tyr Leu Met Val Leu Thr Glu Leu Ile Asn Leu His Leu Lys Val
        755                 760                 765

Gly Trp Lys Arg Gly Asn Pro Ile Trp Arg Val Ile Ser Leu Leu Lys
    770                 775                 780

Asn Ala Ser Ile Gln His Leu Gln Glu Met Asp Ser Gly Gln Glu Pro
785                 790                 795                 800

Thr Val Gly Ser Gln Ile Gln Arg Val Val Ser Met Ala Ala Leu Ala
                805                 810                 815

Met Val Cys Glu Ala Ile Asp Gln Lys Pro Glu Leu Gln Leu Asp Ser
            820                 825                 830

Leu His Ala Gly Pro Leu Glu Ser Phe Leu Ser Ser Leu Gln Leu Asn
        835                 840                 845

Gln Thr Leu Gln Lys Pro His Ala Glu Glu Gln Ser Ser Tyr Ala His
    850                 855                 860

Pro Leu Glu Cys Ser Ser Val Leu Glu Glu Ser Ser Ser Gln Gly
865                 870                 875                 880

Trp Gly Lys Ile Val Ala Gln Tyr Ile His Asp Gln Trp Val Cys Leu
                885                 890                 895

Ser Phe Leu Leu Lys Lys Tyr His Thr Leu Ile Pro Thr Thr Gly Ser
            900                 905                 910

Glu Ile Leu Glu Pro Phe Leu Pro Ala Val Gln Met Pro Ile Arg Thr
        915                 920                 925

Leu Gln Ser Ala Leu Glu Ala Leu Thr Val Leu Ser Ser Asp Gln Val
    930                 935                 940

Leu Pro Val Phe His Cys Leu Lys Val Leu Val Pro Lys Leu Leu Thr
945                 950                 955                 960

Ser Ser Glu Ser Leu Cys Ile Glu Ser Phe Asp Met Ala Trp Lys Ile
                965                 970                 975

Ile Ser Ser Leu Ser Asn Thr Gln Leu Ile Phe Trp Ala Asn Leu Lys
            980                 985                 990

Ala Phe Val Gln Phe Val Phe Asp Asn Lys Val Leu Thr Ile Ala Ala
        995                 1000                1005

Lys Ile Lys Gly Gln Ala Tyr Phe Lys Ile Lys Glu Ile Met Tyr Lys
    1010                1015                1020

Ile Ile Glu Met Ser Ala Ile Lys Thr Gly Val Phe Asn Thr Leu Ile
1025                1030                1035                1040

Ser Tyr Cys Cys Gln Ser Trp Ile Val Ser Ala Ser Asn Val Ser Gln
                1045                1050                1055

Gly Ser Leu Ser Ser Ala Lys Asn Tyr Ser Glu Leu Ile Leu Glu Ala
            1060                1065                1070

Cys Ile Phe Gly Thr Val Phe Arg Arg Asp Gln Arg Leu Val Gln Asp
        1075                1080                1085

Val Gln Thr Phe Ile Glu Asn Leu Gly His Asp Cys Ala Ala Asn Ile
    1090                1095                1100

Val Met Glu Asn Thr Lys Arg Glu Asp His Tyr Val Arg Ile Cys Ala
1105                1110                1115                1120
```

```
Val  Lys  Phe  Leu  Cys  Leu  Leu  Asp  Gly  Ser  Asn  Met  Ser  His  Lys  Leu
                    1125                1130                     1135

Phe  Ile  Glu  Asp  Leu  Ala  Ile  Lys  Leu  Leu  Asp  Lys  Asp  Glu  Leu  Val
               1140                1145                     1150

Ser  Lys  Ser  Lys  Lys  Arg  Tyr  Tyr  Val  Asn  Ser  Leu  Gln  His  Arg  Val
          1155                1160                     1165

Lys  Asn  Arg  Val  Trp  Gln  Thr  Leu  Val  Leu  Phe  Pro  Arg  Leu  Asp
     1170                1175                     1180

Gln  Asn  Phe  Leu  Asn  Gly  Ile  Ile  Asp  Arg  Ile  Phe  Gln  Ala  Gly  Phe
1185                1190                1195                          1200

Thr  Asn  Asn  Gln  Ala  Ser  Ile  Lys  Tyr  Phe  Ile  Glu  Trp  Ile  Ile  Ile
                    1205                1210                     1215

Leu  Ile  Leu  His  Lys  Phe  Pro  Gln  Phe  Leu  Pro  Lys  Phe  Trp  Asp  Cys
                    1220                1225                     1230

Phe  Ser  Tyr  Gly  Glu  Glu  Asn  Leu  Lys  Thr  Ser  Ile  Cys  Thr  Phe  Leu
                    1235                1240                     1245

Ala  Val  Leu  Ser  His  Leu  Asp  Ile  Ile  Thr  Gln  Asn  Ile  Pro  Glu  Lys
               1250                1255                     1260

Lys  Leu  Ile  Leu  Lys  Gln  Ala  Leu  Ile  Val  Val  Leu  Gln  Trp  Cys  Phe
1265                1270                1275                          1280

Asn  His  Asn  Phe  Ser  Val  Arg  Leu  Tyr  Ala  Leu  Val  Ala  Leu  Lys  Lys
                    1285                1290                     1295

Leu  Trp  Thr  Val  Cys  Lys  Val  Leu  Ser  Val  Glu  Glu  Phe  Asp  Ala  Leu
               1300                1305                     1310

Thr  Pro  Val  Ile  Glu  Ser  Ser  Leu  His  Gln  Val  Glu  Ser  Met  His  Gly
               1315                1320                     1325

Ala  Gly  Asn  Ala  Lys  Lys  Asn  Trp  Gln  Arg  Ile  Gln  Glu  His  Phe  Phe
               1330                1335                     1340

Phe  Ala  Thr  Phe  His  Pro  Leu  Lys  Asp  Tyr  Cys  Leu  Glu  Thr  Ile  Phe
1345                1350                1355                          1360

Tyr  Ile  Leu  Pro  Arg  Leu  Ser  Gly  Leu  Ile  Glu  Asp  Glu  Trp  Ile  Thr
                    1365                1370                     1375

Ile  Asp  Lys  Phe  Thr  Arg  Phe  Thr  Asp  Val  Pro  Leu  Ala  Ala  Gly  Phe
               1380                1385                     1390

Gln  Trp  Tyr  Leu  Ser  Gln  Thr  Gln  Leu  Ser  Lys  Leu  Lys  Pro  Gly  Asp
               1395                1400                     1405

Trp  Ser  Gln  Gln  Asp  Ile  Gly  Thr  Asn  Leu  Val  Glu  Ala  Asp  Asn  Gln
     1410                1415                1420

Ala  Glu  Trp  Thr  Asp  Val  Gln  Lys  Lys  Ile  Ile  Pro  Trp  Asn  Ser  Arg
1425                1430                1435                          1440

Val  Ser  Asp  Leu  Asp  Leu  Glu  Leu  Leu  Phe  Gln  Asp  Arg  Ala  Ala  Arg
                    1445                1450                     1455

Leu  Gly  Lys  Ser  Ile  Ser  Arg  Leu  Ile  Val  Val  Ala  Ser  Leu  Ile  Asp
               1460                1465                     1470

Lys  Pro  Thr  Asn  Leu  Gly  Gly  Leu  Cys  Arg  Thr  Cys  Glu  Val  Phe  Gly
          1475                1480                     1485

Ala  Ser  Val  Leu  Val  Val  Gly  Ser  Leu  Gln  Cys  Ile  Ser  Asp  Lys  Gln
     1490                1495                     1500

Phe  Gln  His  Leu  Ser  Val  Ser  Ala  Glu  Gln  Trp  Leu  Pro  Leu  Val  Glu
1505                1510                1515                          1520

Val  Lys  Pro  Pro  Gln  Leu  Ile  Asp  Tyr  Leu  Gln  Gln  Lys  Lys  Thr  Glu
                    1525                1530                     1535

Gly  Tyr  Thr  Ile  Ile  Gly  Val  Glu  Gln  Thr  Ala  Lys  Ser  Leu  Asp  Leu
```

```
                        1540                    1545                        1550
Thr Gln Tyr Cys Phe Pro Glu Lys Ser Leu Leu Leu Leu Gly Asn Glu
        1555                    1560                1565

Arg Glu Gly Ile Pro Ala Asn Leu Ile Gln Gln Leu Asp Val Cys Val
    1570            1575                1580

Glu Ile Pro Gln Gln Gly Ile Ile Arg Ser Leu Asn Val His Val Ser
1585                1590                1595            1600

Gly Ala Leu Leu Ile Trp Glu Tyr Thr Arg Gln Gln Leu Leu Ser His
                1605                1610            1615

Gly Asp Thr Lys Pro
            1620
```

( 2 ) INFORMATION FOR SEQ ID NO:3:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

```
Gly Gly Ala Gly Gly Gly
1               5
```

( 2 ) INFORMATION FOR SEQ ID NO:4:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
Arg Arg Gln Arg Arg Arg
1               5
```

( 2 ) INFORMATION FOR SEQ ID NO:5:

( i ) SEQUENCE CHARACTERISTICS:
        ( A ) LENGTH: 72 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:5:

```
YTNAARCCNG GNGAYTGGTG NCARCARGAY ATAGGNACNA CYYTNGTNGA RGCNGAYAAY        60
CARGCNGARG GN                                                           72
```

( 2 ) INFORMATION FOR SEQ ID NO:6:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:6:

```
AARCCNGGNG AYTGG                                                        15
```

(2) INFORMATION FOR SEQ ID NO:7:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:7:

GAYTGGWSNC ARCARGA 17

(2) INFORMATION FOR SEQ ID NO:8:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:8:

GGRAGNCGRA CYAAYAG 17

(2) INFORMATION FOR SEQ ID NO:9:

(i) SEQUENCE CHARACTERISTICS:
      (A) LENGTH: 17 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:9:

ACYAAYAGNC GRAGNTG 17